US009046683B2

(12) United States Patent
Caldeira et al.

(10) Patent No.: US 9,046,683 B2
(45) Date of Patent: Jun. 2, 2015

(54) ADJUSTABLE OPTICS FOR ONGOING VIEWING CORRECTION

(75) Inventors: Kenneth G. Caldeira, Redwood City, CA (US); Peter L. Hagelstein, Carlisle, MA (US); Roderick A. Hyde, Seattle, WA (US); Edward K. Y. Jung, Bellevue, WA (US); Jordin T. Kare, Seattle, WA (US); Nathan P. Myhrvold, Bellevue, WA (US); John Brian Pendry, Cobham (GB); David Schurig, Raleigh, NC (US); Clarence T. Tegreene, Bellevue, WA (US); Charles Whitmer, North Bend, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 112 days.

(21) Appl. No.: 13/374,520

(22) Filed: Dec. 29, 2011

(65) Prior Publication Data

US 2013/0170022 A1    Jul. 4, 2013

Related U.S. Application Data

(63) Continuation-in-part of application No. 13/374,533, filed on Dec. 29, 2011, and a continuation-in-part of application No. 13/374,517, filed on Dec. 29, 2011.

(51) Int. Cl.
*G02B 7/36* (2006.01)
*G02B 7/28* (2006.01)
(Continued)

(52) U.S. Cl.
CPC ........ *G02B 27/0093* (2013.01); *G02B 27/0025* (2013.01); *G02B 26/06* (2013.01);
(Continued)

(58) Field of Classification Search
CPC ............. G02B 7/365; G02B 7/28; G02B 7/36
USPC .......................................... 351/159.39, 159.4
See application file for complete search history.

(56) References Cited

U.S. PATENT DOCUMENTS 4,105,302 A    8/1978    Tate, Jr.
4,418,990 A    12/1983    Gerber
(Continued)

FOREIGN PATENT DOCUMENTS

WO    WO 90/05926    5/1990
OTHER PUBLICATIONS

Abramowitz, Mortimer et al.; "Eyepieces (Oculars)"; 2010; pp. 1-9; Olympus America Inc. located at http://www.olympusmicro.com/primer/anatomy/oculars.html.
(Continued)

*Primary Examiner* — Thomas K Pham
*Assistant Examiner* — Marin Pichler

(57) ABSTRACT

Exemplary methods, systems and components enable an enhanced direct-viewing optical device to make customized adjustments that accommodate various optical aberrations of a current user. In some instances a real-time adjustment of the transformable optical elements is based on known corrective optical parameters associated with a current user. In some implementations a control module may process currently updated wavefront measurements as a basis for determining appropriate real-time adjustment of the transformable optical elements to produce a specified change in optical wavefront at an exit pupil of the direct-viewing device. Possible transformable optical elements may have refractive and/or reflective and/or diffractive and/or transmissive characteristics that are adjusted based on current performance viewing factors for a given field of view of the direct-viewing device. Some embodiments enable dynamic repositioning and/or transformation of corrective optical elements based on a detected shift of a tracked gaze direction of a current user of the direct-viewing device.

47 Claims, 38 Drawing Sheets

(51) Int. Cl.

| | | |
|---|---|---|
| *G02B 27/02* | (2006.01) | |
| *G02B 27/00* | (2006.01) | |
| *G02B 26/06* | (2006.01) | |
| *A61B 3/14* | (2006.01) | |
| *A61B 3/15* | (2006.01) | |
| *G02B 23/12* | (2006.01) | |
| *G02B 21/24* | (2006.01) | |
| *A61B 3/10* | (2006.01) | |
| *A61B 3/113* | (2006.01) | |

(52) U.S. Cl.
CPC ............ *G02C2202/22* (2013.01); *A61B 3/1015* (2013.01); *A61B 3/113* (2013.01); *A61B 3/14* (2013.01); *A61B 3/152* (2013.01)

(56) References Cited

U.S. PATENT DOCUMENTS

| | | | |
|---|---|---|---|
| 4,724,454 A | 2/1988 | Misawa | |
| 4,936,667 A | 6/1990 | Röhr et al. | |
| 4,955,702 A | 9/1990 | Nakamura | |
| 5,090,796 A | 2/1992 | Feinbloom | |
| 5,182,585 A | 1/1993 | Stoner | |
| 5,483,301 A | 1/1996 | Clarke | |
| 5,835,289 A | 11/1998 | Berry | |
| 6,058,090 A | 5/2000 | Wang et al. | |
| 6,478,425 B2 | 11/2002 | Trajkovic et al. | |
| 6,480,339 B2 | 11/2002 | Clark | |
| 6,511,180 B2 | 1/2003 | Guirao et al. | |
| 6,568,809 B2 | 5/2003 | Trajkovic et al. | |
| 6,709,108 B2 | 3/2004 | Levine et al. | |
| 6,761,454 B2 | 7/2004 | Lai et al. | |
| 6,786,602 B2 | 9/2004 | Abitbol | |
| 7,009,161 B2 | 3/2006 | Hoffmann | |
| 7,021,764 B2 | 4/2006 | Dreher | |
| 7,086,928 B2 | 8/2006 | Siders et al. | |
| 7,246,906 B2 | 7/2007 | Mihashi et al. | |
| 7,268,890 B2 | 9/2007 | Emer | |
| 7,303,281 B2 | 12/2007 | Wakil et al. | |
| 7,334,894 B2 | 2/2008 | Hillis et al. | |
| 7,365,738 B2 | 4/2008 | Molander et al. | |
| 7,371,041 B2 | 5/2008 | Pfeiffer et al. | |
| 7,384,146 B2 | 6/2008 | Covannon et al. | |
| 7,387,387 B2 | 6/2008 | Dai | |
| 7,412,711 B2 | 8/2008 | Jernstrom et al. | |
| 7,490,936 B2* | 2/2009 | Blum et al. | 351/159.39 |
| 7,500,750 B2 | 3/2009 | Sabeta | |
| 7,568,799 B2 | 8/2009 | Dreher et al. | |
| 7,599,122 B2 | 10/2009 | Liao | |
| 7,697,212 B2 | 4/2010 | Jethmalani et al. | |
| 7,699,471 B2 | 4/2010 | Lai | |
| 7,708,401 B2 | 5/2010 | Sabeta | |
| 7,708,405 B2 | 5/2010 | Chernyak | |
| 7,724,454 B2 | 5/2010 | Lin | |
| 7,726,811 B2 | 6/2010 | Lai | |
| 7,736,000 B2 | 6/2010 | Enriquez et al. | |
| 7,815,310 B2 | 10/2010 | Su et al. | |
| 7,824,033 B2 | 11/2010 | Lai | |
| 7,832,863 B2 | 11/2010 | Dreher et al. | |
| 8,047,651 B2 | 11/2011 | Blum et al. | |
| 8,246,609 B2 | 8/2012 | Zickler et al. | |
| 2002/0071095 A1 | 6/2002 | Roffman et al. | |
| 2002/0104961 A1 | 8/2002 | Hoffman | |
| 2002/0113943 A1 | 8/2002 | Trajkovic et al. | |
| 2002/0196412 A1* | 12/2002 | Abitbol | 351/246 |
| 2003/0053028 A1 | 3/2003 | Wirth | |
| 2004/0057014 A1 | 3/2004 | Altmann | |
| 2004/0165284 A1* | 8/2004 | Holler | 359/805 |
| 2005/0174535 A1 | 8/2005 | Lai et al. | |
| 2006/0274261 A1 | 12/2006 | Andino et al. | |
| 2007/0229756 A1 | 10/2007 | Mandler et al. | |
| 2008/0024594 A1* | 1/2008 | Ritchey | 348/36 |
| 2008/0080846 A1 | 4/2008 | Grip | |
| 2008/0086207 A1 | 4/2008 | Sandstedt et al. | |
| 2008/0151175 A1* | 6/2008 | Gross | 351/45 |
| 2008/0158502 A1 | 7/2008 | Becker et al. | |
| 2008/0174732 A1* | 7/2008 | Blum et al. | 351/168 |
| 2008/0278808 A1 | 11/2008 | Redert | |
| 2009/0122265 A1 | 5/2009 | Dai et al. | |
| 2009/0251663 A1 | 10/2009 | Warden et al. | |
| 2010/0065625 A1 | 3/2010 | Sabeta | |
| 2010/0265463 A1 | 10/2010 | Lai | |
| 2010/0281021 A1 | 11/2010 | Weeber et al. | |
| 2011/0001930 A1 | 1/2011 | Levecq | |
| 2011/0157547 A1 | 6/2011 | Dillon et al. | |
| 2011/0221656 A1 | 9/2011 | Haddick et al. | |
| 2011/0221657 A1 | 9/2011 | Haddick et al. | |
| 2011/0228226 A1 | 9/2011 | Pixton et al. | |
| 2011/0250823 A1 | 10/2011 | Paillet et al. | |
| 2011/0299034 A1 | 12/2011 | Walsh et al. | |
| 2012/0218498 A1* | 8/2012 | Bonora et al. | 349/113 |

OTHER PUBLICATIONS

"Active Focus Control for Deformable Mirrors"; Bridger Photonics; Nov. 21, 2011; pp. 1-3; located at http://www.bridgerphotonics.com/technology.php?product_id=36.

"Astigmatism"; A.D.A.M. Medical Encyclopedia; Jul. 28, 2011; 2 pages; A.D.A.M., Inc.

"Binoculars from the specialist"; Monk Optics; Nov. 7, 2011; pp. 1-4; located at http://www.monkoptics.co.uk/General/binocularterms.html.

Bush, Keith et al.; "Electrostatic Membrane Deformable Mirror Characterization and Applications"; Proc. SPIE; 2005; pp. 1-15; SPIE.

Coe, Steve; "A Guide to Eyepieces"; printed on Dec. 14, 2011; pp. 1-3; located at http://www.saguaroastro.org/content/print-friendly/print-EYEPIECE.htm.

Cornelissen, S.A. et al.; "MEMS Deformable Mirrors for Astronomical Adaptive Optics"; Proc. of SPIE; 2010; pp. 77362D-1-77362D-10; vol. 7736, 77362D.

De Fez, Ma Dolores et al.; "Enhancement of Contrast Sensitivity and Losses of Chromatic Discrimination with Tinted Lenses"; Optometry and Vision Science; Sep. 2002; 8 pages; vol. 79, No. 9; American Academy of Optometry.

"Fundamentals of Remote Sensing—A Canada Centre for Remote Sensing Remote Sensing Tutorial"; Canada Centre for Remote Sensing; Oct. 27, 2011; pp. 39-42 and cover page; located at http://www.uprm.edu/biology/profs/chinea/gis/g06/NRC2_3_2_6.pdf.

Hawks, Chuck; "Binocular Basics"; 2010; pp. 1-7; located at http://www.chuckhawks.com/binocular_basics.htm.

Heiting, Gary; High-Definition Eyeglass Lenses; Aug. 2011; pp. 1-4; located at http://www.allaboutvision.com/lenses/wavefront-lenses.htm.

Kalloniatis, Michael et al.; "Visual Acuity"; Jun. 5, 2007; pp. 1-19; located at http://webvision.med.utah.edu/book/part-viii-gabac-receptors/visual-acuity/.

Kersten, Daniel et al.; "Convergence accommodation"; J. Opt. Soc. Am.; Mar. 1983; pp. 332-338; vol. 73, No. 3; Optical Society of America.

"Lightzone v3 Imaging—Imaging Introduction"; Sep. 6, 2011; pp. 1-5; located at http://www.photozone.de/lightzone-v205.

Love, Gordon D.; "Adaptive Optical Components Using Liquid Crystal Devices"; Journal of the Communications Research Laboratory; Nov. 1999; pp. 427-430; vol. 46, No. 3.

Meng, Fan-Yi et al.; Controllable Metamaterial-Loaded Waveguides Supporting Backward and Forward Waves; IEEE Transactions on Antennas and Propagation; Sep. 2011; pp. 3400-3411; vol. 59, No. 9; IEEE.

Millodot: Dictionary of Optometry and Visual Science, 7th Edition; "Convergence"; 2009; pp. 1-3; Butterworth-Heinemann; located at http://medical-dictionary.thefreedictionary.com/convergence.

Minin, I. V. et al.; "Subwavelength Diffractive Photonic Crystal Lens"; Progress in Electromagnetics Research B; 2008; pp. 257-264, vol. 7.

"Ophthonix Introduces Customizable High-Resolution iZon(R) eFocusTM Computer Lens"; Ophthonix, Inc.; Mar. 22, 2011; 1 page.

"Optical Design"; celestron.com; Nov. 8, 2011; pp. 1-4; located at http://www.celestron.com/c2/popup spec.php?ID=1.

(56) References Cited

OTHER PUBLICATIONS

"Stops and Apertures"; Nov. 8, 2011; pp. 1-10; located at http://electron9.phys.utk.edu/optics421/modules/m3/Stops.htm.

"Tech Talk Riflescopes"; Bushnell; 2011; pp. 1-5; located at http://www.bushnell.com/products/scopes/riflescopes/tech-talk/.

"The Compound Microscope"; microscopehelp.com; Nov. 8, 2011; pp. 1-3; located at http://www.microscopehelp.com/thecompoundmicroscope.html.

Wikipedia; "File:Hexagon-Figure.jpg"; Aug. 16, 2010; 2 pages; located at http://en.wikipedia.org/wiki/File:HEXAGON-Figure.jpg.

Wyant, James C. et al.; "Chapter 1: Basic Wavefront Aberration Theory for Optical Metrology"; 1992; pp. 1, 28-39; Academic Press, Inc.

"Z•View™ Aberrometer—The only lens made to the patient's unique optical fingerprint or iPrint™"; 2008; pp. 1-8; Informoptic Ch-1272 Genolier/VD Switzerland.

Cannistra, P. et al.; "Micro-transfer molding of SU-8 micro-optics"; Advanced Fabrication Technologies for Micro/Nano Optics and Photonics, Proc. of SPIE; 2008; pp. 68830C-1-68830C-9; vol. 6883.

"CD Player Operation"; Basic Car Audio Electronics; printed on Feb. 28, 2012; 8 pages; located at http://www.bcael.com/cdplayer.htm.

Dyer, David et al.; "Sequential shrink photolithography for plastic microlens arrays"; Applied Physics Letters; 2011; p. 034102-1-034102-3; vol. 99; American Institute of Physics.

Fu, Yong-Qi et al.; "Microfabrication of microlens array by focused ion beam technology"; Microelectronic Engineering; 2000; pp. 211-221; vol. 54; Elsevier Science B.V.

Krueger, Ronald R. et al.; Wavefront Customized Visual Correction—The Quest for Super Vision II; 2004; Chapter 33, cover and $1^{st}$ page, and pp. 279-284; SLACK Incorporated.

"Lens Polishing Pressure Measurement & Analysis"; Tekscan, Inc.; 2007; pp. 1-5; located at http://www.tekscan.com/lens-polishing-pressure-distribution.

"Motorized Filter Flipper"; Thorlabs; Feb. 1, 2012; pp. 1-2; located at http://www.thorlabs.com/NewGroupPage9.cfm?ObjectGroup_ID=3962.

Thibos, Larry N. et al.; "Standards for Reporting the Optical Aberrations of Eyes"; Journal of Refractive Surgery; Sep./Oct. 2002; pp. S652-S660; vol. 18.

Tuteleers, P. et al.; "Investigation of the replication quality of plastic micro-optical interconnection components"; Proc. $6^{th}$ An. Symp. IEEE/LEOS Benelux Chapter; 2001; pp. 73-77.

Tuteleers, P. et al.; "Replication of Refractive Micro Opto-mechanical Components Made with Deep Lithography with Protons"; Proceedings Symposium IEEE/LEOS Benelux Chapter; 2000; pp. 211-214.

Yao, Jun et al.; "Refractive micro lens array made of dichromate gelatin with gray-tone photolithography"; Microelectronic Engineering; 2001; pp. 729-735; vol. 57-58; Elsevier Science B.V.

\* cited by examiner

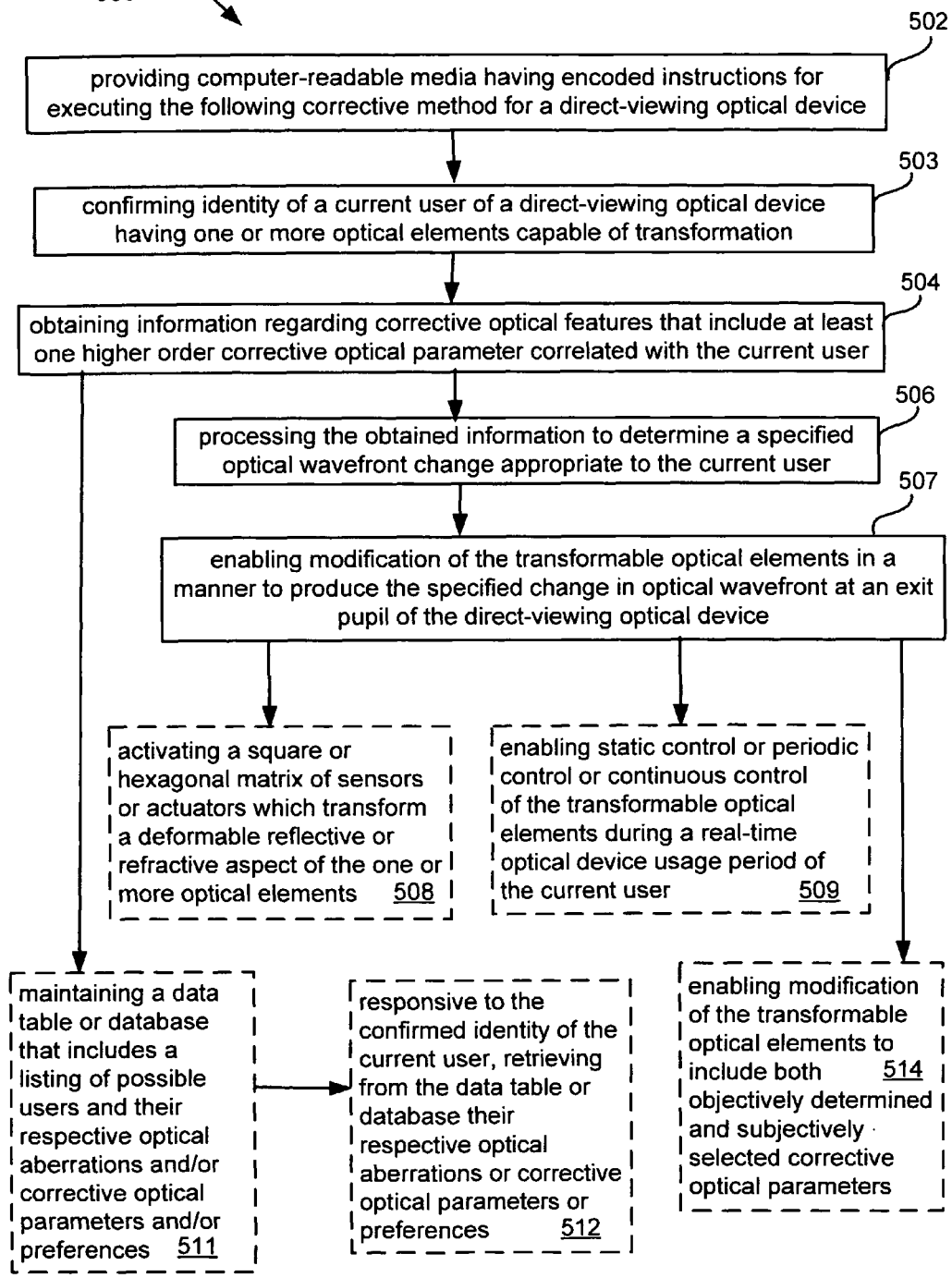

FIG. 16

DATA TABLE RECORDS 600

| PERFORMANCE VIEWING FACTOR 610 | DEVICE XX USER BILL 615 | DEVICE YY USER BILL 620 | DEVICE XX USER ANN 625 | DEVICE YY USER EVA 630 | DEVICE ZZ USER EVA 635 |
|---|---|---|---|---|---|
| FIELD OF VIEW 612 | | | | | N/A 646 |
| BRIGHTNESS 614 | | | | | |
| IDENTIFIED TARGET OBJECT 616 | N/A 642 | | N/A 644 | | |
| SCENE CONTRAST 618 | | | | | |
| SPATIAL FREQUENCY CONTENT 622 | | | | | |
| SPECTRAL ATTRIBUTES 624 | | | | | N/A 647 |
| FOCAL LENGTH OF OPTICAL DEVICE 626 | | | | | |
| APERTURE STOP 628 | | | | | |
| USER'S PUPIL DIAMETER 632 | | N/A 648 | | N/A 649 | |
| GENERIC DEFAULT 634 | | | | | |

ADJUSTABLE OPTICS FOR ONGOING VIEWING CORRECTION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/374,533, entitled OPTICAL DEVICE WITH ACTIVE USER-BASED ABERRATION CORRECTION, naming Kenneth G. Caldeira, Peter L. Hagelstein, Roderick A. Hyde, Edward K. Y. Jung, Jordin T. Kare, Nathan P. Myhrvold, John Brian Pendry, David Schurig, Clarence T. Tegreene, Charles Whitmer, Lowell L. Wood, Jr. as inventors, filed 29 Dec. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,517, entitled CORRECTIVE ALIGNMENT OPTICS FOR OPTICAL DEVICE, naming Kenneth G. Caldeira, Peter L. Hagelstein, Roderick A. Hyde, Edward K. Y. Jung, Jordin T. Kare, Nathan P. Myhrvold, John Brian Pendry, David Schurig, Clarence T. Tegreene, Charles Whitmer, Lowell L. Wood, Jr. as inventors, filed 29 Dec. 2011, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

BACKGROUND

The present application relates to methods, devices, apparatus and systems regarding corrective optical components adapted for use with a direct-viewing optical device.

SUMMARY

In one aspect, an exemplary method for optical adjustment of a direct-viewing optical device may include selecting a direct-viewing device having one or more transformable optical elements incorporated as a component; periodically detecting one or more real-time performance viewing factors regarding an operating condition or image property or viewing environment for a given field of view of the direct-viewing optical device; processing information regarding low-order and/or high-order aberrations correlated with a current user of the direct-viewing optical device; and responsive to the detected performance viewing factors and based on the processed aberration information, adjusting the transformable optical elements in a manner to produce a specified change in optical wavefront at an exit pupil of the direct-viewing optical device.

In one or more various aspects, related systems and apparatus include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In another aspect, an exemplary system includes but is not limited to computerized components regarding corrective optical elements and/or direct-viewing optical devices, which system has the capability to implement the various process features disclosed herein. Examples of various system and apparatus aspects are described in the claims, drawings, and text forming a part of the present disclosure.

Some exemplary adjustable systems for a direct-viewing optical device may include one or more optical elements adapted for mounting on the direct-viewing optical device, wherein the optical elements are capable of transformation to achieve enhanced acuity during a period of usage by a current user; and a control module operably coupled to the one or more transformable optical elements in a manner to activate or modify or bypass certain optical features based on performance viewing factors to produce a specified change in optical wavefront at an exit pupil of the direct-viewing optical device, wherein the specified change includes at least one higher-order corrective feature respectively correlated with an aberrational characteristic of the current user. A related exemplary system aspect may include at least one sensor component operatively coupled to the control module and configured to monitor or measure one or more real-time performance viewing factors regarding an operating condition or image property or viewing environment for a given field of view of the direct-viewing optical device.

In a further aspect, a computer program product may include computer-readable media having encoded instructions for executing an optical adjustment method for a direct-viewing optical device, wherein the method includes periodically detecting one or more real-time performance viewing factors regarding an operating condition or image property or viewing environment for a given field of view of the direct-viewing optical device that includes one or more transformable optical elements; processing information regarding low-order and/or high-order aberrations correlated with a current user of the direct-viewing optical device; and responsive to the detected performance viewing factors and based on the processed aberration information, adjusting the transformable optical elements in a manner to produce a specified change in optical wavefront at an exit pupil of the direct-viewing optical device.

In addition to the foregoing, various other method and/or system and/or program product aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 15 is a diagrammatic flow chart for exemplary computer-readable media embodiment features.

FIG. 16 shows a representative data table regarding adjustable corrective aspects for given performance viewing factors.

DETAILED DESCRIPTION

Figure 1:
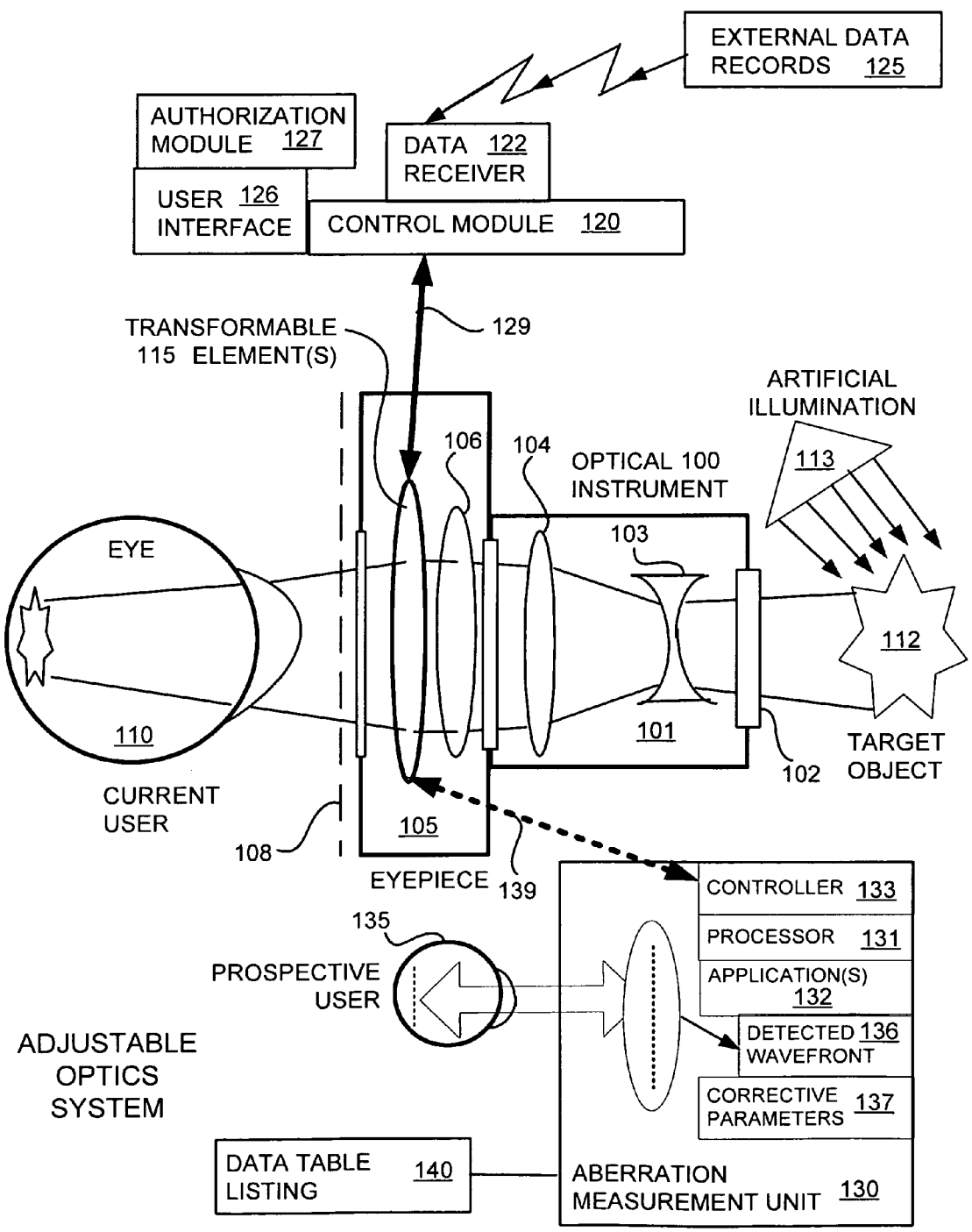
FIG. 1 is a schematic block diagram illustrating exemplary embodiment features for adjustable optics incorporated in a direct-viewing optical device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences.

In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

FIG. 1 is a schematic block diagram illustrating a direct-viewing optical device such as optical instrument 100 having a customized eyepiece 105 configured with one or more transformable optical elements 115 to enhance viewing acuity for an eye 110 of a current user. Other optical elements may also be incorporated with the optical instrument 100 to achieve a desired clear field of view of a target object 112 under various lighting conditions such as artificial illumination 113. Examples of such other optical elements are shown symbolically in the eyepiece 105 (e.g., see refractive lens 106) and also in an optical instrument body 101 (e.g., see aperture 102, diffractive lens 103, refractive lens 104) to provide operative visual coupling with the transformable optical elements 115. In some instances the transformable optical elements 115 may include an element having variable chromatic aberration properties, and/or other aberration properties.

A control module 120 may be connected via a communication link (e.g., see electrical link 129) to the transformable optical elements 115 and provides customized adjustment in accordance with optical corrective parameters associated with the current user. In that regard such optical corrective parameters and/or their respective user aberrations may be accessible via a data receiver 122 from external data records 125 for processing by the control module 120 in a manner to achieve an optimum optical wavefront at an exit pupil (see representation of approximate exit plane 108) of the optical instrument 100.

A user interface 126 together with authorization module 127 are adapted to recognize identity of the current user. The control module 120 includes circuitry and/or software that is configured to cause the transformable optical elements 115 to be adjusted based on appropriate optical corrective parameters associated with the current user.

In some system embodiments an aberration measurement unit 130 may be available for monitoring an eye 135 of a prospective user in order to obtain a new or updated data record regarding a detected wavefront 136. The aberration measurement unit 130 may include processor 131, one or more applications 132, as well as controller 133 and light source (not shown) to obtain and process the newly acquired wavefront data as well as in some instances determine appropriate corrective parameters 137 for the prospective user. An optional communication link 139 may provide a direct connection between controller 133 and the transformable optical elements 115 for enabling customized adjustment during a time of usage of the optical instrument 100 by the prospective user. Some implementations may include a data table listing 140 linked with the aberration measurement unit for maintaining user preferences, previously determined wavefront data, and default corrective parameters related to different specific optical instruments or types of optical instruments.

It will be understood that the particular additional optical elements disclosed herein are for purposes of illustration only, and are intended to represent various combinations of optical elements that can be chosen and situated in a direct-viewing optical device in a manner to provide operative visual coupling with the transformable optical elements shown in FIGS. 1-5.

Figure 2:
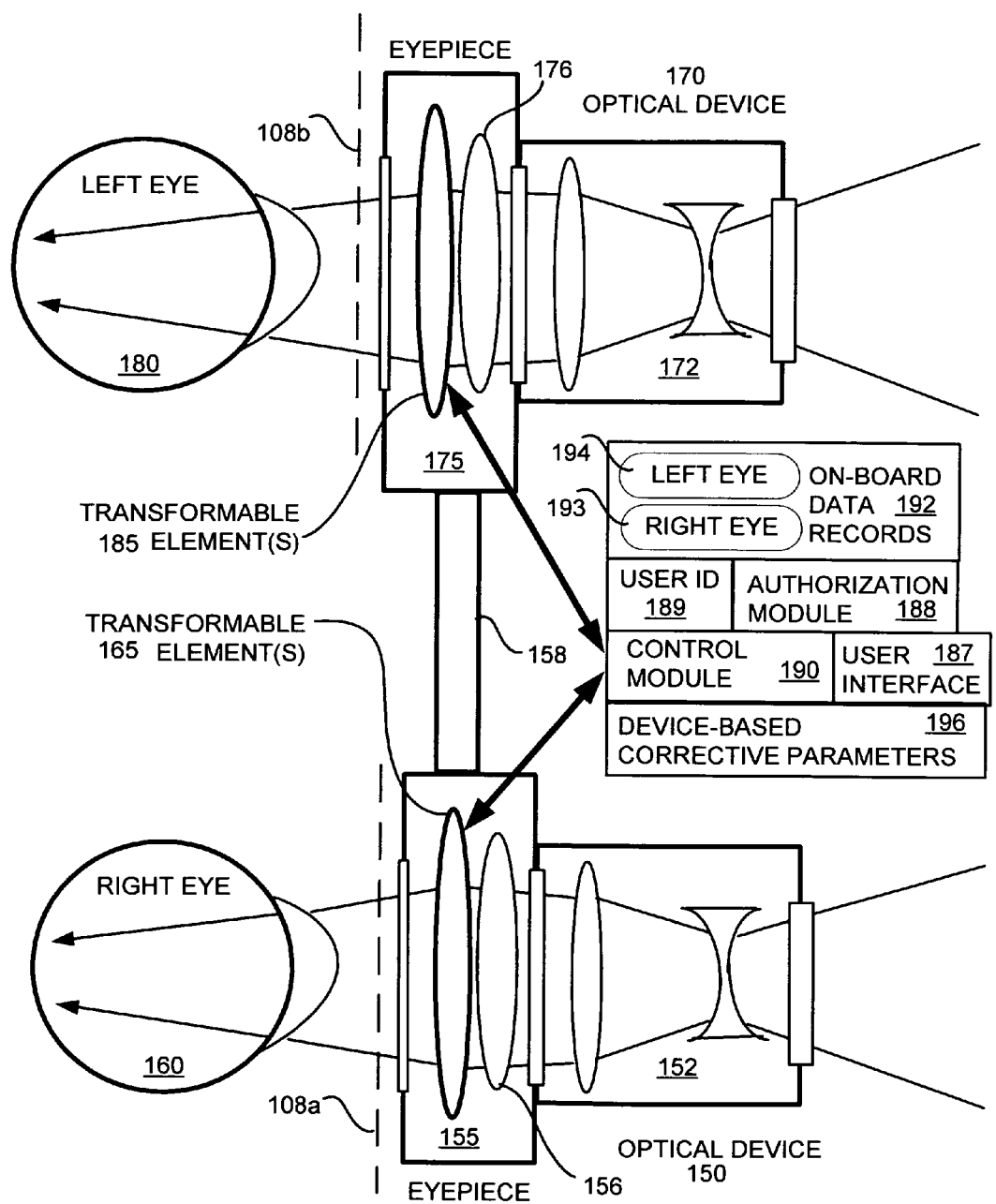
FIG. 2 is a schematic block diagram illustrating exemplary features for another adjustable optics embodiment.

FIG. 2 is schematic block diagram illustrating a composite direct-viewing optical device that includes two optical device portions 150, 170. Optical device portion 150 includes a customized eyepiece 160 configured with one or more transformable optical elements 165 to enhance viewing acuity for a right eye 160 of a current user. Additional optical elements may also be incorporated with the customized eyepiece 160 (e.g., see refractive element 156) and may be included as part of an optical body portion 152 (e.g., reflective, refractive, diffractive, transmissive elements) to achieve a desired clear field of view of under various viewing conditions.

Optical device portion 170 includes a customized eyepiece 175 configured with one or more transformable optical elements 185 to enhance viewing acuity for a left eye 180 of a current user. It will be understood that some aberrations and related corrective parameters may be respectively different for a right eye 160 and for a left eye 180 of an identified user (see on-board data records 192). In other instances the same corrective parameters may be correlated with both eyes of a current user, depending on the circumstances.

Additional optical elements may also be incorporated with the optical device portion 170 to achieve a desired clear field of view under various viewing conditions. Examples of such other optical elements are shown symbolically in the customized eyepiece 175 (e.g., see refractive lens 176) and may be included in an optical instrument body 172 (e.g., reflective, refractive, diffractive, transmissive elements), and are configured in a manner to provide operative visual coupling with the transformable optical elements 185.

An exemplary system embodiment shown in FIG. 2 may include control module 190 having user interface 187, and on-board data records 192 that include right eye 193 and left eye 194 wavefront aberrations, user preferences, and other user-related information. The control module 190 is operatively linked to both sets of transformable elements 165, 185 in order to make dynamic adjustment applicable to each eye of a current optical device user who is recognized by authorization module 188 and matched with their user ID 189. Additional records may include device-based corrective parameters 196 that ameliorate optical defects of a specific direct-viewing optical device. It will be understood that control module 190 includes circuitry and/or software configured in a manner to achieve an optimum optical wavefront for a particular user at an exit pupil (see representation of approximate exit planes 108a, 108b) of the composite direct-viewing device depicted in FIG. 2.

Figure 3:
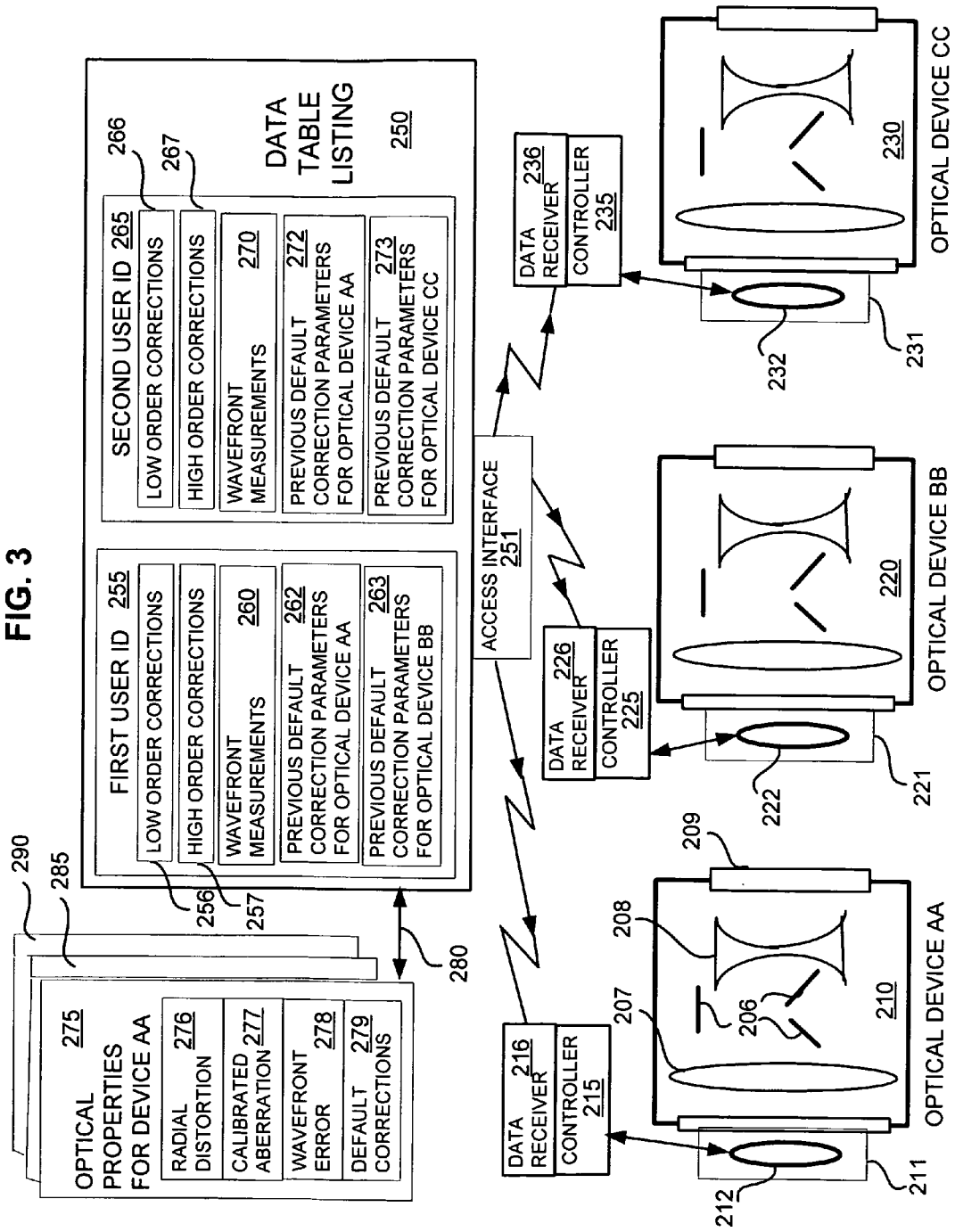
FIG. 3 is a schematic block diagram illustrating corrective optical data records that are accessible to several direct-viewing optical devices.

Referring to the schematic block diagram of FIG. 3, a possible system embodiment may include a data table listing 250 maintained for multiple approved users indicated by a first user identity 255, and a second user identity 265, inter alia. In some instances the data table listing may also provide user-related optical preferences respectively applicable to different direct-viewing optical devices 210, 220, 230.

For example, known informational data correlated with first user ID 255 may include low order corrections 256, high order corrections 257, wavefront measurements 260, and previous default corrective parameters 262 respectively for optical device AA (see 210), and previous default parameters 263 respectively for optical device BB (see 220). As another example, known informational data correlated with the second user ID 265 may include low order corrections 266, high order corrections 267, wavefront measurements 170, previous default corrective parameters 272 respectively for optical device AA (see 210), and previous default corrective parameters 273 respectively for optical device CC (see 230).

An additional data table record may be maintained regarding known optical properties for device AA (see 275), a further data table regarding known optical properties for device BB (see 285), and another data table regarding known optical properties for device CC (see 290). Such data table records may respectively indicate for each optical device AA, BB, CC various pertinent inherent optical properties such as radial distortion 276, calibrated aberration 277, wavefront error 278, and default corrections 279.

It will be understood that the informational data shown in the data tables and data records of FIG. 3 are for purposes of illustration only, and may be expanded or altered in some embodiments and may be shortened or omitted in other embodiments depending on the circumstances.

A communication link 280 may be provided between data table listing 250 and data table records 275, 285, 290 to assure data retrieval and/or data entry via an access interface 251. In that regard an exemplary embodiment includes a wired or wireless operative connection between the access interface 251 and data receiver 216 for optical device 210, and between the access interface 251 and data receiver 226 for optical device 220, and between the access interface 251 and data receiver 236 for optical device 230. It will be understood that different users may be actively engaged with their respectively located and uniquely adjusted direct-viewing devices during a same period of time. Also a single user may use specifically different direct-viewing optical devices during sequential periods of time while enjoying real-time customized optical corrective parameters associated with their previously known or currently updated wavefront aberrations.

A controller 215 may include circuitry and/or software for processing information received by data receiver 216 as a basis for customized real-time optical adjustment of transformable optical element 212 incorporated with eyepiece 211 of optical device 210. Such optical adjustment is correlated with a current user's corrective parameters, and may occur automatically or optionally in accordance with a current user's preference. As previously indicated, a body of the optical device 210 may provide additional optical elements that include reflective 206, refractive 207, diffractive 208, and/or transmissive 209 characteristics to achieve enhanced acuity for a current user.

Similarly a controller 225 may include circuitry and/or software for processing information received by data receiver 226 as a basis for customized real-time optical adjustment of transformable optical element 222 incorporated with eyepiece 221 of optical device 220. Such optical adjustment is correlated with a current user's corrective parameters, and may occur automatically or optionally in accordance with indicated preferences of a current user.

Similarly a controller 235 may include circuitry and/or software for processing information received by data receiver 236 as a basis for customized real-time optical adjustment of transformable optical element 232 incorporated with eyepiece 231 of optical device 230. Such optical adjustment is correlated with a current user's corrective parameters, and may occur automatically or optionally in accordance with indicated preferences of a current user.

Figure 4:
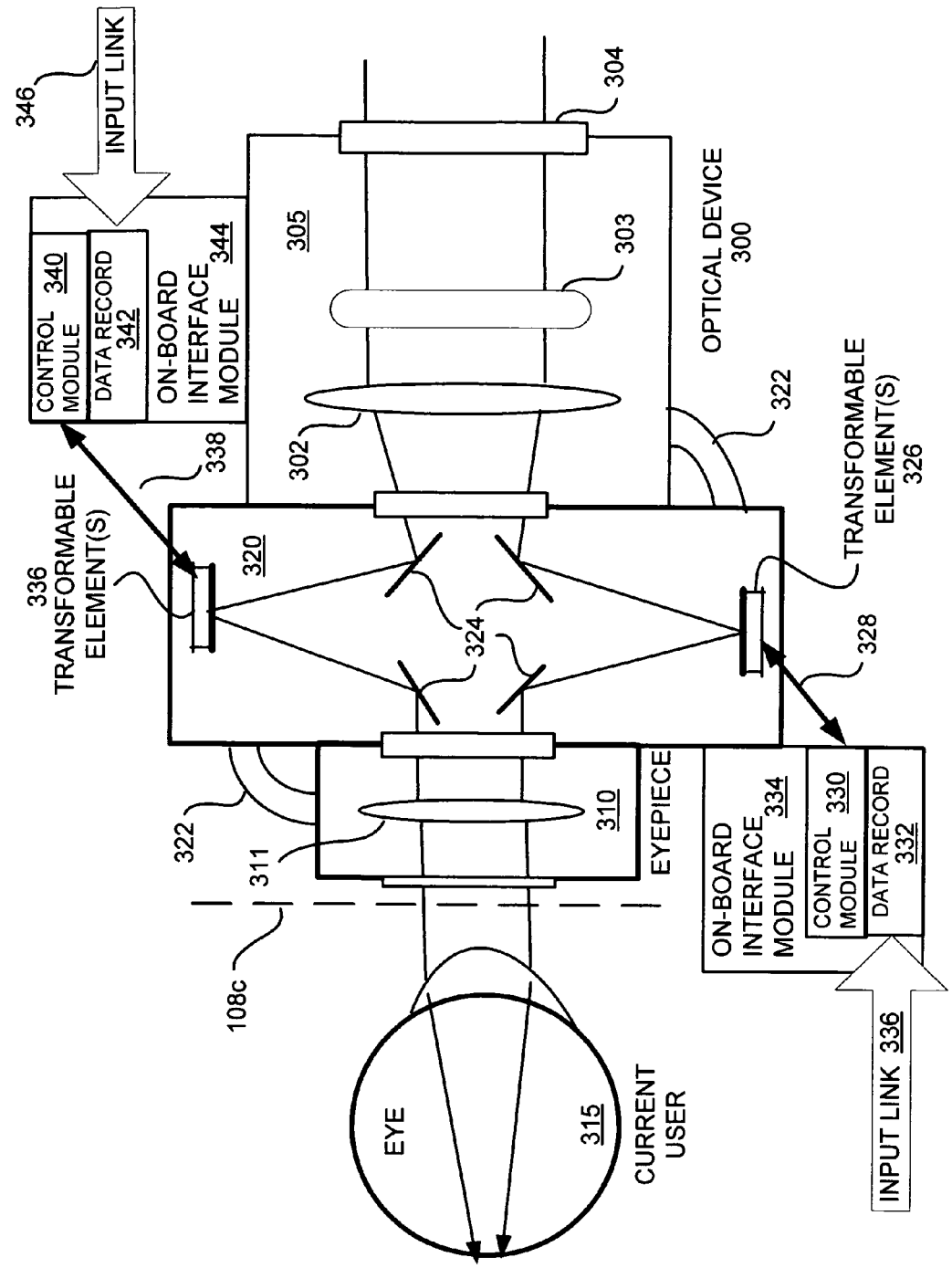
FIGS. 4-5 are schematic block diagrams illustrating additional examples of adjustable optical embodiments.

FIG. 4 is a schematic block diagram illustrating a direct-viewing optical device 300 having an eyepiece 310 and body portion 305, with a customized optical component 320 mounted and secured by brackets 322 as an integral insert between the eyepiece 105 and body portion 305. In this embodiment the customized optical component 320 is configured to include one or more transformable optical elements (e.g., reflective elements 326, 336) to enhance viewing acuity for an eye 315 of a current user. Other optical elements may also be incorporated with the optical device 300 to achieve a desired clear field of view under various viewing conditions. Examples of such other optical elements are shown symbolically in the eyepiece 310 (e.g., see refractive lens 311) and body portion 305 (e.g., see aperture 304, transmissive filter 303, refractive lens 302), and also in the customized optical component 320 (e.g., see reflective elements 324) to provide operative visual coupling with the transformable optical elements 326, 336.

Control modules 330, 340 may be respectively connected via electrical links 328, 338 to the transformable optical elements 326, 336 for customized real-time adjustment based on low-order and/or high-order aberrations associated with the current user. In that regard, a first on-board interface module 334 may include certain optical corrective parameters in data record 332 for processing by control module 330, and a second on-board interface module 344 may include other optical corrective parameters in data record 342 for processing by control module 340, in a manner to achieve an optimum optical wavefront at an exit pupil (see representation of approximate exit plane 108c) of the optical instrument 300. Updated user aberration data as well as user preferences, etc. may be received via input link 336 to data record 322, as well as via input link 346 to data record 342.

Figure 5:
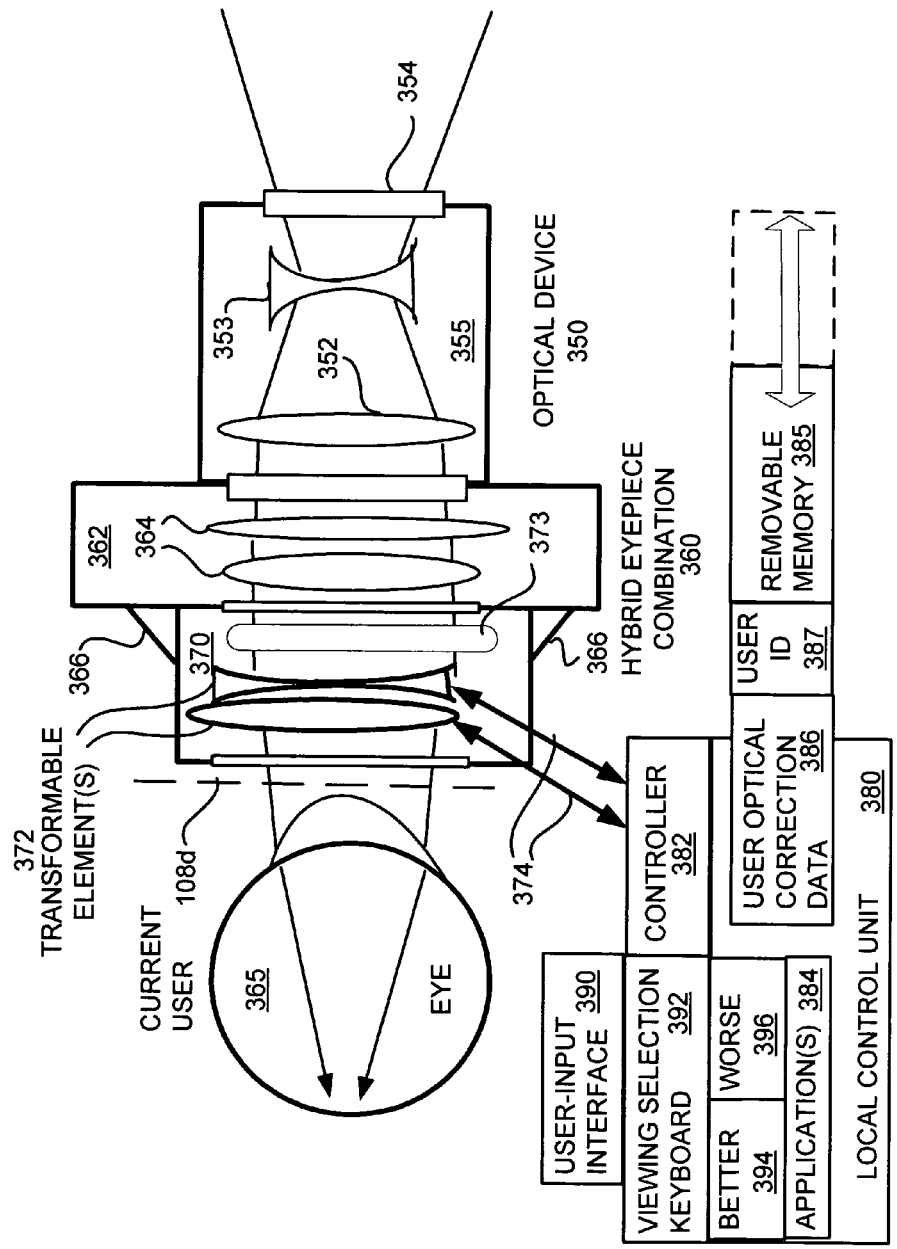

Referring to the schematic block diagram of FIG. 5, an exemplary embodiment may include a direct-viewing optical device 350 having a hybrid eyepiece combination 360 that includes a conventional eyepiece 362 with an auxiliary customized optical component 370 mountable adjacent a current user's eye 365 on adapter ring 366. This enables the auxiliary customized optical component 370 to be manually removable during a period of ordinary generic usage of the optical device 350, or optionally mounted between the conventional eyepiece 362 and a current user's eye 365 to enable dynamic adjustment of transformable elements 372 during a hyperacuity usage period.

In this embodiment the auxiliary customized optical component 370 is configured to include one or more transformable optical elements (e.g., displaceable refractive/diffractive elements 372) to enhance viewing acuity for the eye 365 of a current user. Other optical elements may also be incorporated with the optical device 350 to achieve a desired clear field of view under various viewing conditions. Examples of such other optical elements are shown symbolically in the conventional eyepiece 362 (e.g., see different refractive elements 364) and body portion 355 (e.g., see aperture 354, diffractive lens 353, refractive lens 352), and also in the customized optical component 370 (e.g., see transmissive filter elements 373) to provide operative visual coupling with the transformable optical elements 372. Exemplary types of filter elements may include wide band, narrow band, ultra-violet (UV) blocking, polarizer, chromatic, etc. in order to optimize acuity for a current user of a particular direct-viewing optical device.

An exemplary local control unit 380 includes controller 382 and one or more program applications 384 for processing aberrational corrections correlated with the current user. In that regard, the local control unit 380 may be adapted to receive removable memory records 385 that include user optical correction data 386 along with a verifiable user ID 387. This enables the controller 382 to process such user optical correction data 386 and transmit appropriate control signals via electrical communication links 374 to the transformable elements 372 during a period of usage by the verified current user.

A further exemplary feature of local control unit 380 includes components for enabling subjective determination of optimal adjustment of the transformable elements 372. A user-input interface 390 is linked with a viewing selection keyboard 392 such that the current user can make data entries based on comparison between alternative adjustments of the transformable elements 372 for varied viewing conditions or different fields of view or selected target objects as seen through the hybrid eyepiece combination 385. The user's subjective determinations can be indicated as "better" 394 or "worse" 396 as a basis for real-time implementation by controller 362, and also can be maintained in a data record for future reference.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Figure 6:
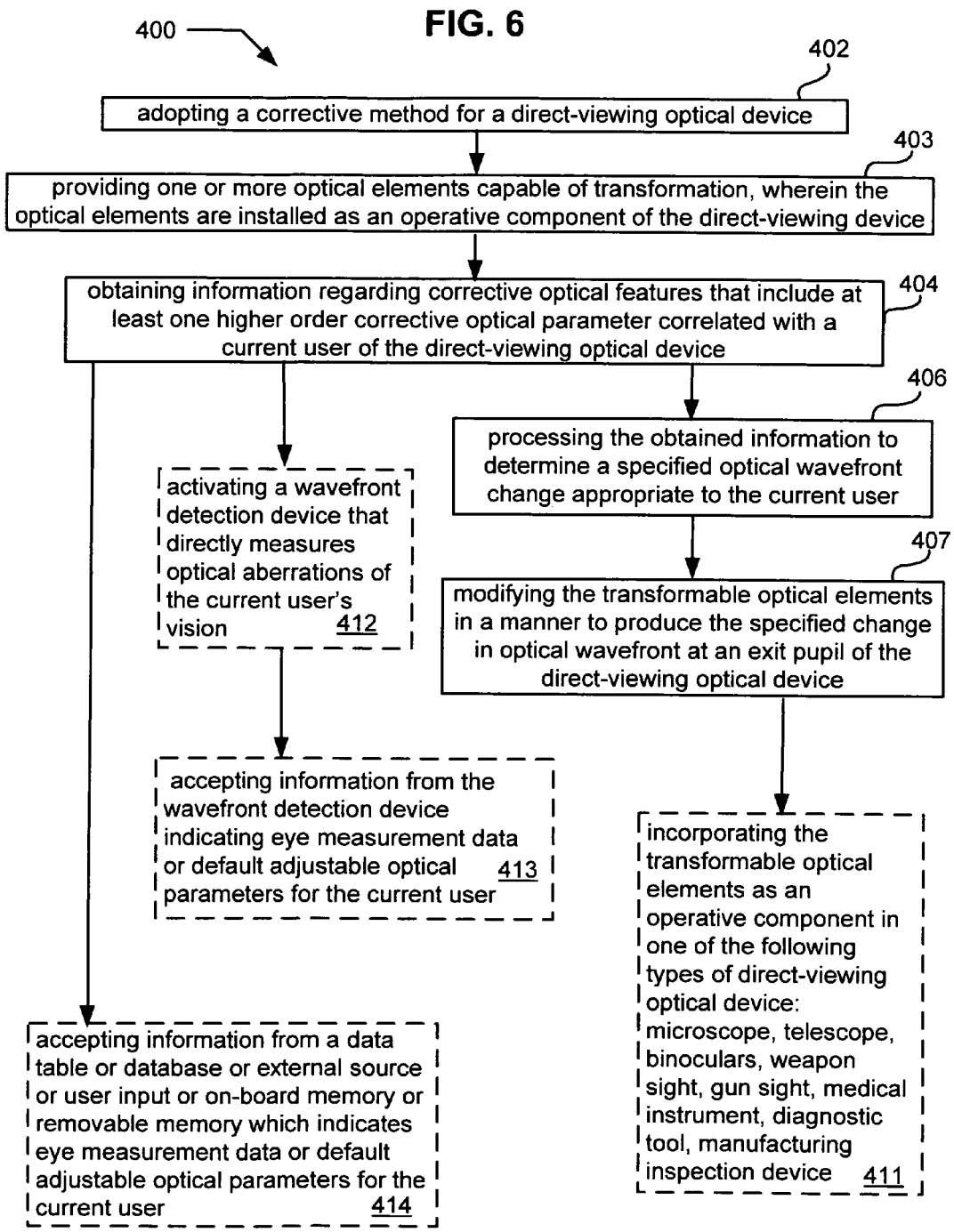
FIG. 6 is a high level flow chart that shows exemplary method aspects for providing enhanced acuity in a direct-viewing optical device.

Referring to embodiment features 400 shown in the high level flow chart of FIG. 6, an adopted corrective method for a direct-viewing optical device (see block 402) may include providing one or more optical elements capable of transformation, wherein the optical elements are installed as an operative component of the direct-viewing device (block 403); and obtaining information regarding corrective optical features that include at least one higher order corrective optical parameter correlated with a current user of the direct-viewing optical device (block 404). Related exemplary aspects include processing the obtained information to determine a specified optical wavefront change appropriate to the current user (block 406), and modifying the transformable optical elements in a manner to produce the specified change in optical wavefront at an exit pupil of the direct-viewing optical device (block 407).

In some instances further process exemplary features include incorporating the transformable optical elements as an operative component in one of the following types of direct-viewing optical device: microscope, telescope, binoculars, weapon sight, gun sight, medical instrument, diagnostic tool, manufacturing inspection device (block 411). Other process examples include activating a wavefront detection device that directly measures optical aberrations of the current user's vision (block 412), and accepting information from the wavefront detection device indicating eye measurement data or default adjustable optical parameters for the current user (block 413).

Further possible aspects shown in FIG. 6 include accepting information from a data table or database or external source or user input or on-board memory or removable memory which indicates eye measurement data or default adjustable optical parameters for the current user (block 414).

Figure 7:
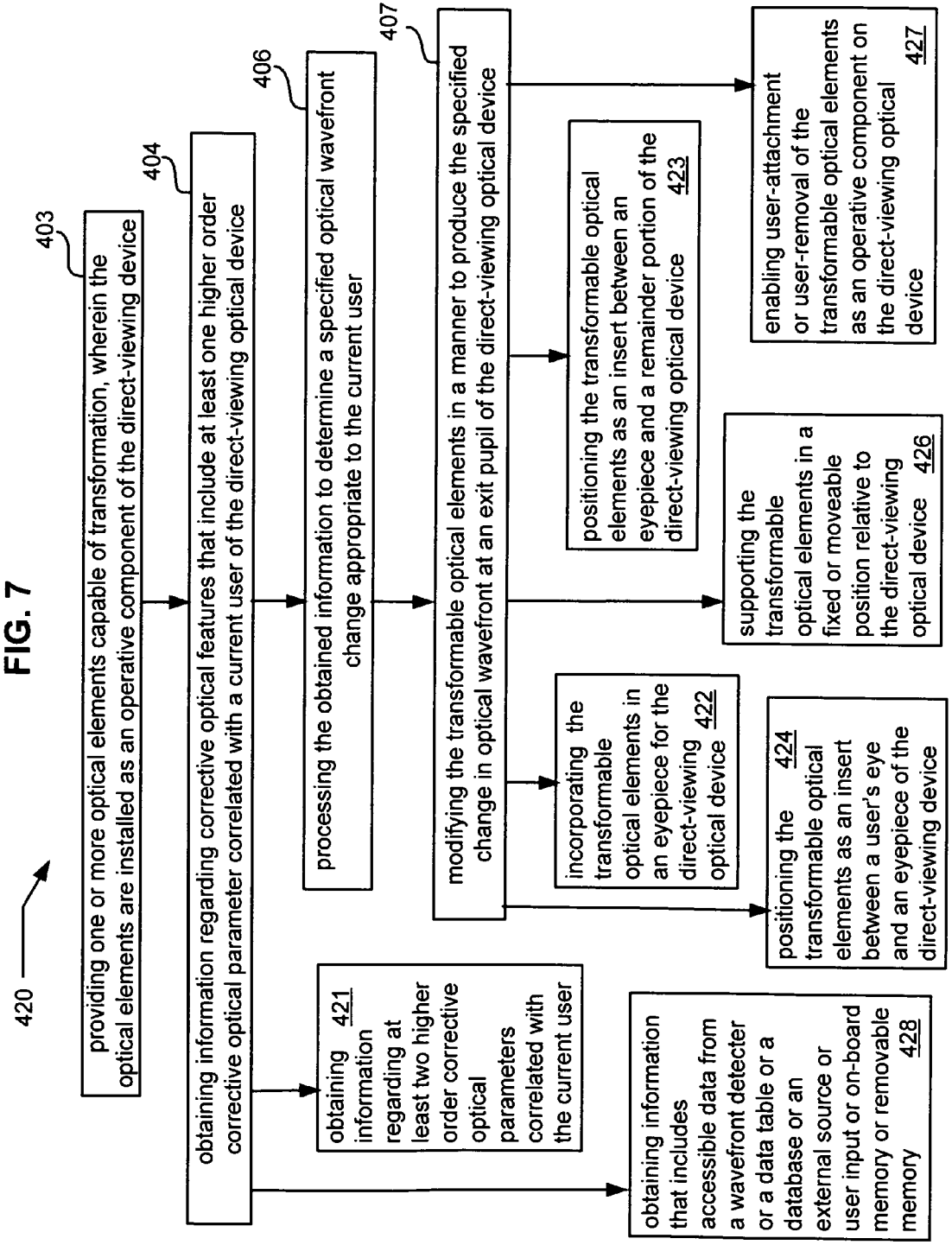
FIGS. 7-14 are detailed flow charts illustrating further exemplary method aspects for adjustable optical embodiments.

The flow chart of FIG. 7 illustrates further process embodiment features 420 that include previously described aspects 403, 404, 406, 407 in combination with obtaining information regarding at least two higher order corrective optical parameters correlated with the current user (block 421). A further process operation may include obtaining information that includes accessible data from a wavefront detector or a data table or a database or an external source or user input or on-board memory or removable memory (block 428).

Other exemplary process aspects include incorporating the transformable optical elements in an eyepiece for the direct-viewing optical device (block 422), and in some instances positioning the transformable optical elements as an insert between an eyepiece and a remainder portion of the direct-viewing optical device (block 423). Other possible process embodiments include positioning the transformable optical elements as an insert between a user's eye and an eyepiece of the direct-viewing device (block 424), as well as supporting the transformable optical elements in a fixed or moveable position relative to the direct-viewing optical device (block 426). Further possibilities include enabling user-attachment or user-removal of the transformable optical elements as an operative component on the direct-viewing optical device (block 427).

Figure 8:
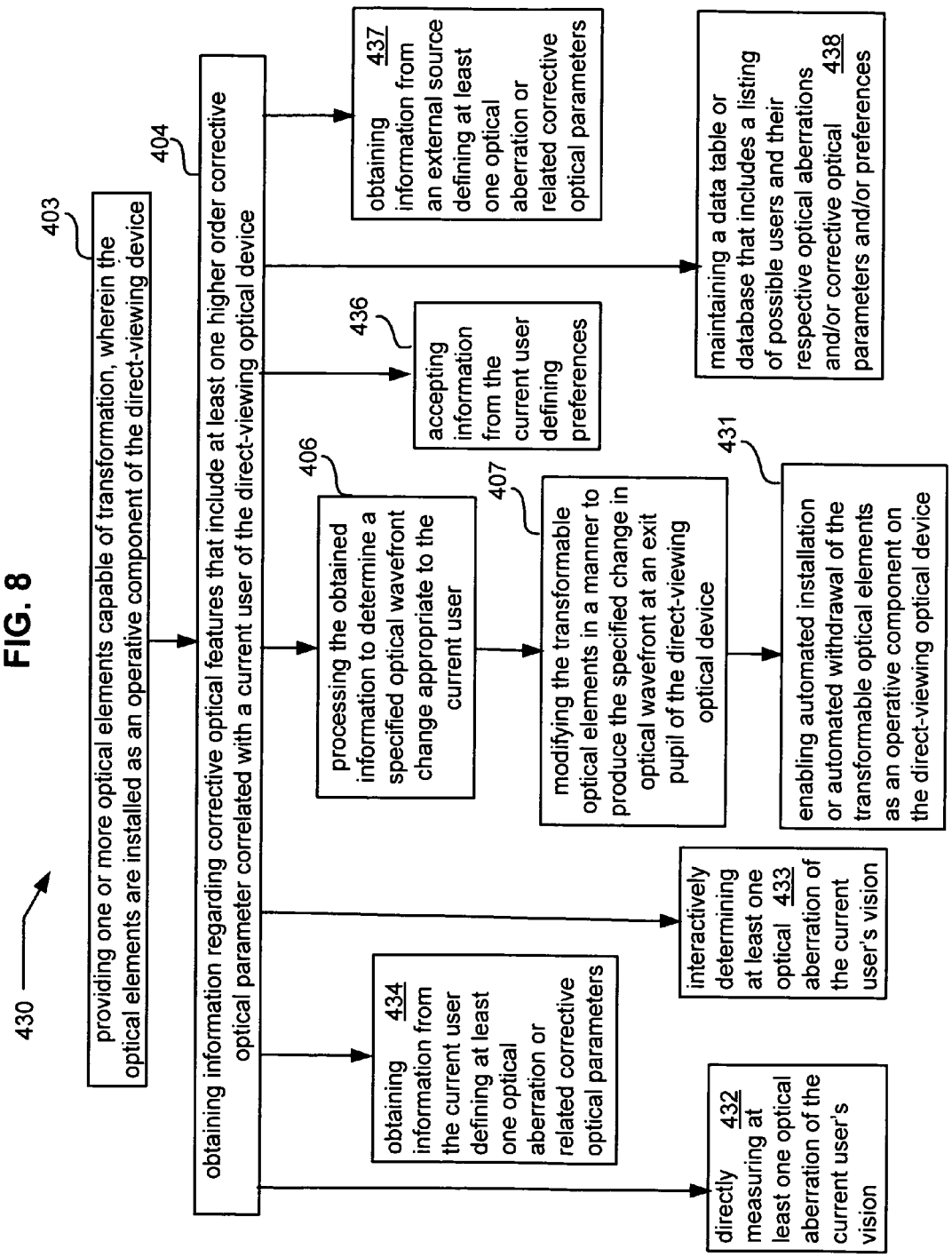

FIG. 8 shows various embodiment features 430 that include previously described aspects 403, 404, 406, 407 as well as enabling automated installation or automated withdrawal of the transformable optical elements as an operative component on the direct-viewing optical device (block 431). In some embodiments a further aspect includes directly measuring at least one optical aberration of the current user's vision (block 432). Other aspects may include interactively determining at least one optical aberration of the current user's vision (block 433), and obtaining information from the current user defining at least one optical aberration or related corrective optical parameters (block 434).

Further process enhancements may include accepting information from the current user defining preferences (block 436), and obtaining information from an external source defining at least one optical aberration or related corrective optical parameters (block 437). Additional exemplary aspects include maintaining a data table or database that includes a listing of possible users and their respective optical aberrations and/or corrective optical parameters and/or preferences (block 438).

Figure 9:
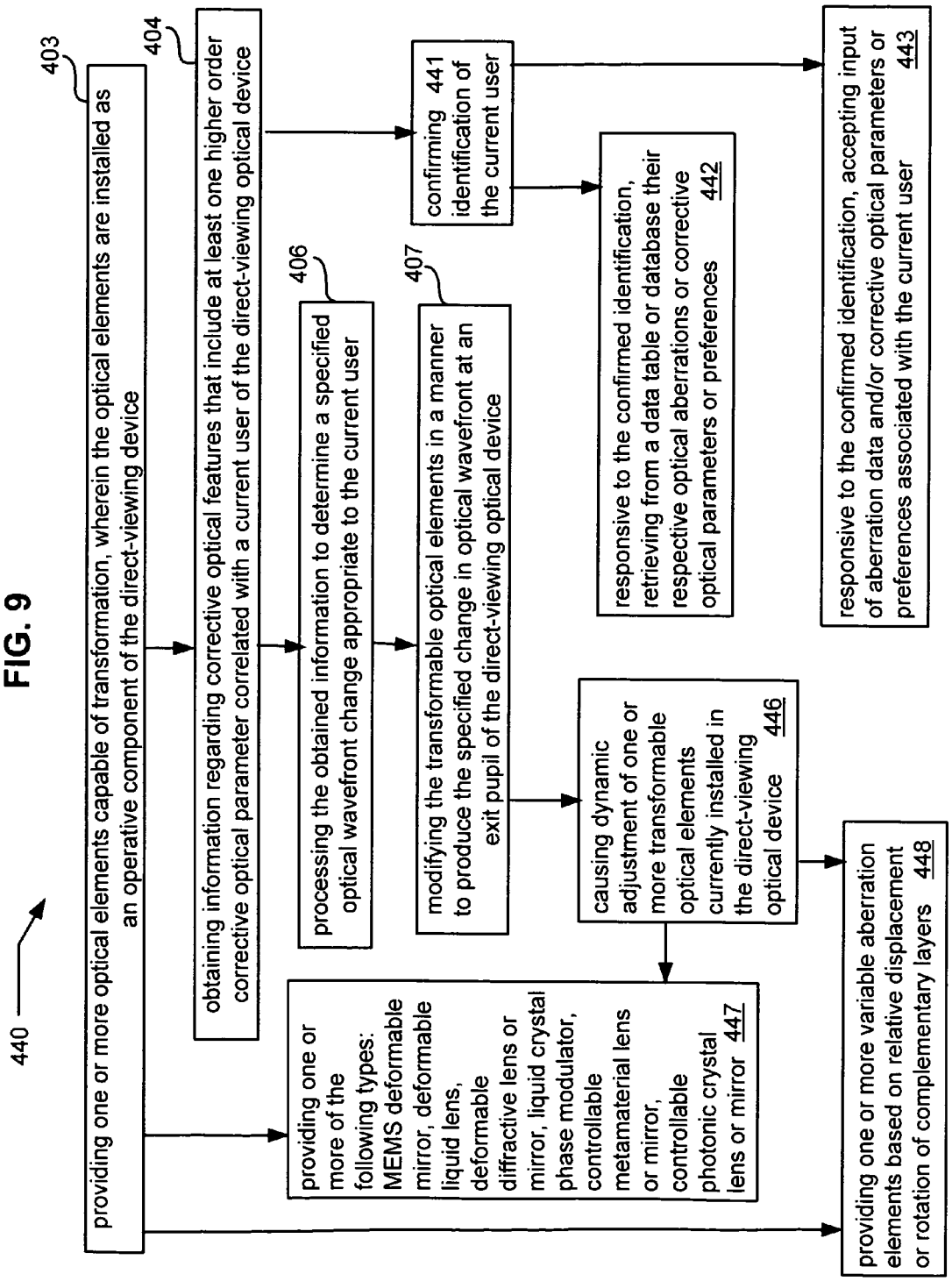

The detailed flow chart of FIG. 9 illustrates embodiment features 440 that include previously described process aspects 403, 404, 406, 407 in combination with confirming identification of the current user (block 441). An additional possible aspect responsive to the confirmed identification of the current user includes retrieving from a data table or database their respective optical aberrations or corrective optical parameters or preferences (block 443). A further possible aspect responsive to the confirmed identification of the current user includes accepting input of aberration data and/or corrective optical parameters or preferences associated with the current user (block 443).

Another illustrated process feature includes causing dynamic adjustment of one or more transformable optical elements currently installed in the direct-viewing optical device (block 446). Related exemplary features regarding the transformable optical elements include providing one or more of the following types: MEMS deformable mirror, deformable liquid lens, deformable diffractive lens or mirror, liquid crystal phase modulator, controllable metamaterial lens or mirror, controllable photonic crystal lens or mirror (block 447). In some instances a further related feature regarding the transformable optical elements includes providing one or more variable aberration elements based on relative displacement or rotation of complementary layers (block 448).

Figure 10:
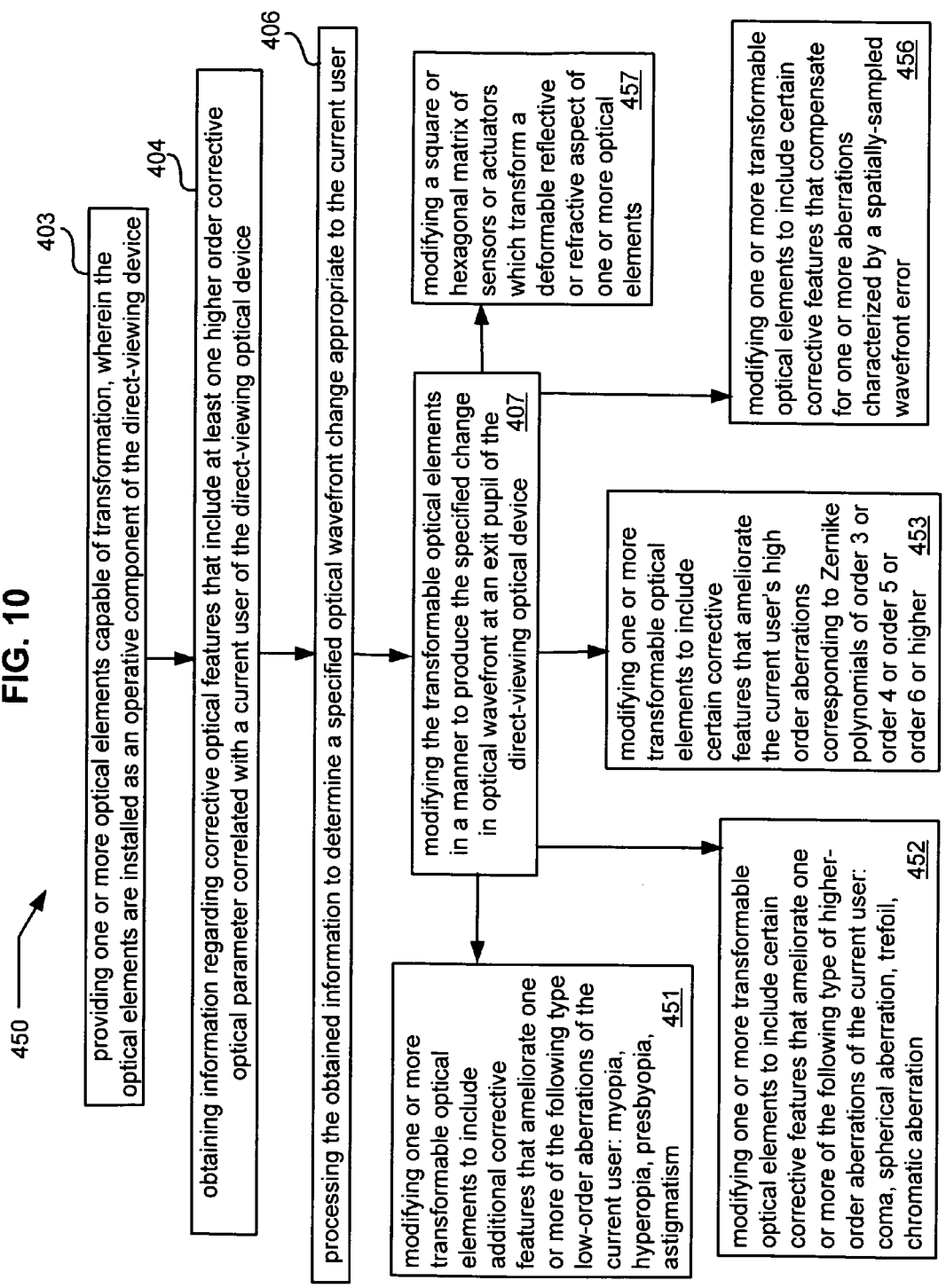

Referring to FIG. 10, additional exemplary process features 450 are shown including previously described features 403, 404, 406, 407 which may be combined with modifying one or more transformable optical elements to include additional corrective features that ameliorate one or more of the following type low-order aberrations of the current user: myopia, hyperopia, presbyopia, astigmatism (block 451). Another possible process feature include modifying one or more transformable optical elements to include certain corrective features that ameliorate one or more of the following type of higher-order aberrations of the current user: coma, spherical aberration, trefoil, chromatic aberration (block 452).

Some embodiments may provide an implementation that includes modifying one or more transformable optical elements to include certain corrective features that ameliorate the current user's high order aberrations corresponding to Zernike polynomials of order 3 or order 4 or order 5 or order 6 or higher (block 453). Other related aspects may include modifying the one or more transformable optical elements to include certain corrective features that compensate for one or more aberrations characterized by a spatially-sampled wavefront error (block 456). Further possible aspects include modifying a square or hexagonal matrix of sensors or actuators which transform a deformable reflective or refractive aspect of one or more optical elements (block 457).

Figure 11:
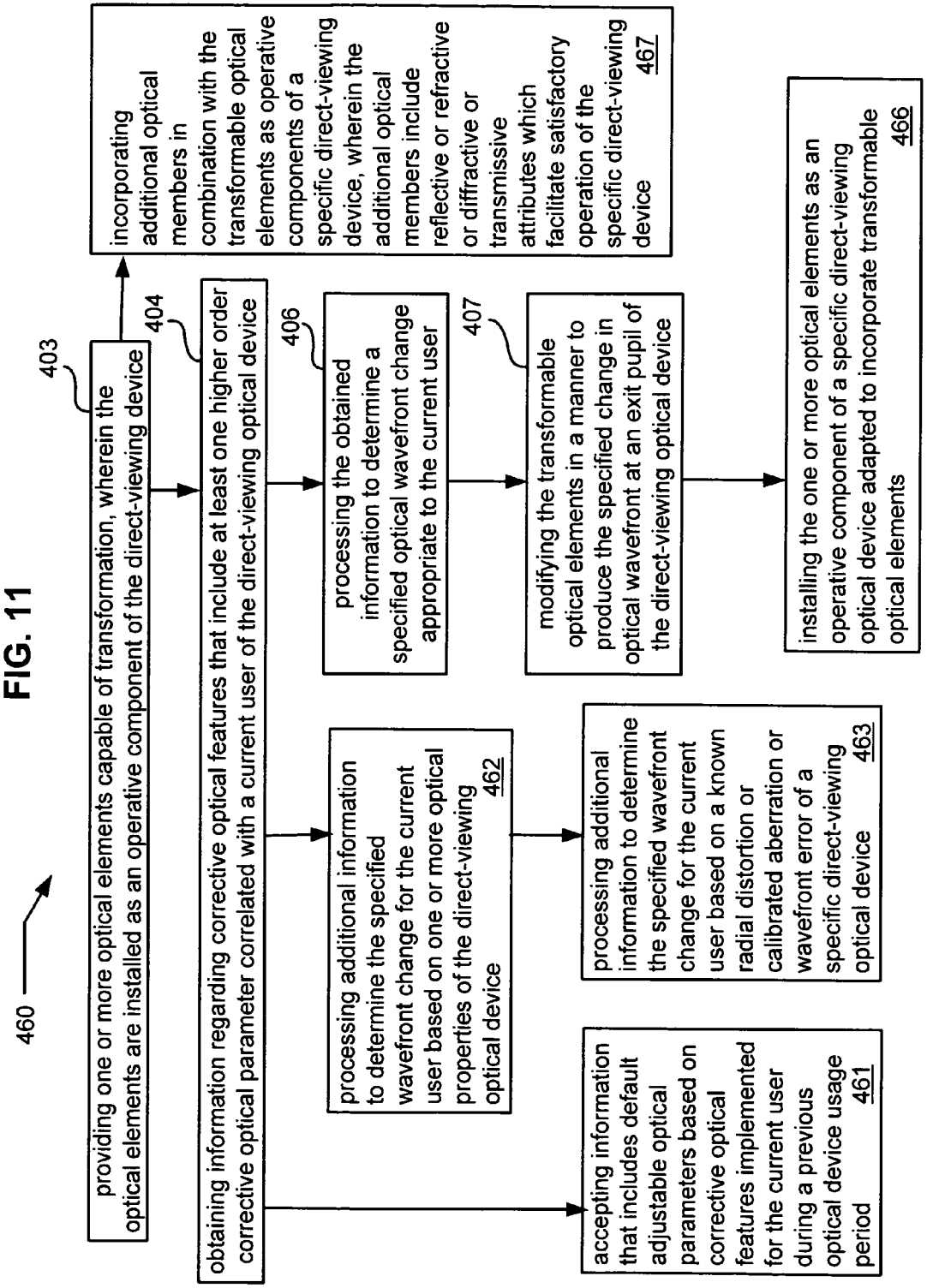

Various process features 460 depicted in the flow chart of FIG. 11 include previously described aspects 403, 404, 406, 407 as well as accepting information that includes default adjustable optical parameters based on corrective optical features implemented for the current user during a previous optical device usage period (block 461). Another possible process feature includes processing additional information to determine the specified wavefront change for the current user based on one or more optical properties of the direct-viewing optical device (block 462). A further illustrated aspect includes processing additional information indicating automatic adjustable optical parameters for the current user based on a known radial distortion or calibrated aberration or wavefront error of a specific-direct-viewing optical device (block 463).

Some process embodiments include installing the one or more optical elements as an operative component of a specific direct-viewing optical device adapted to incorporate transformable optical elements (block 466). A further process aspect may include incorporating additional optical members in combination with the transformable optical elements as operative components of the specific direct-viewing device, wherein the additional optical members include reflective or refractive or diffractive or transmissive attributes which facilitate satisfactory operation of the direct-viewing device (block 467).

Figure 12:
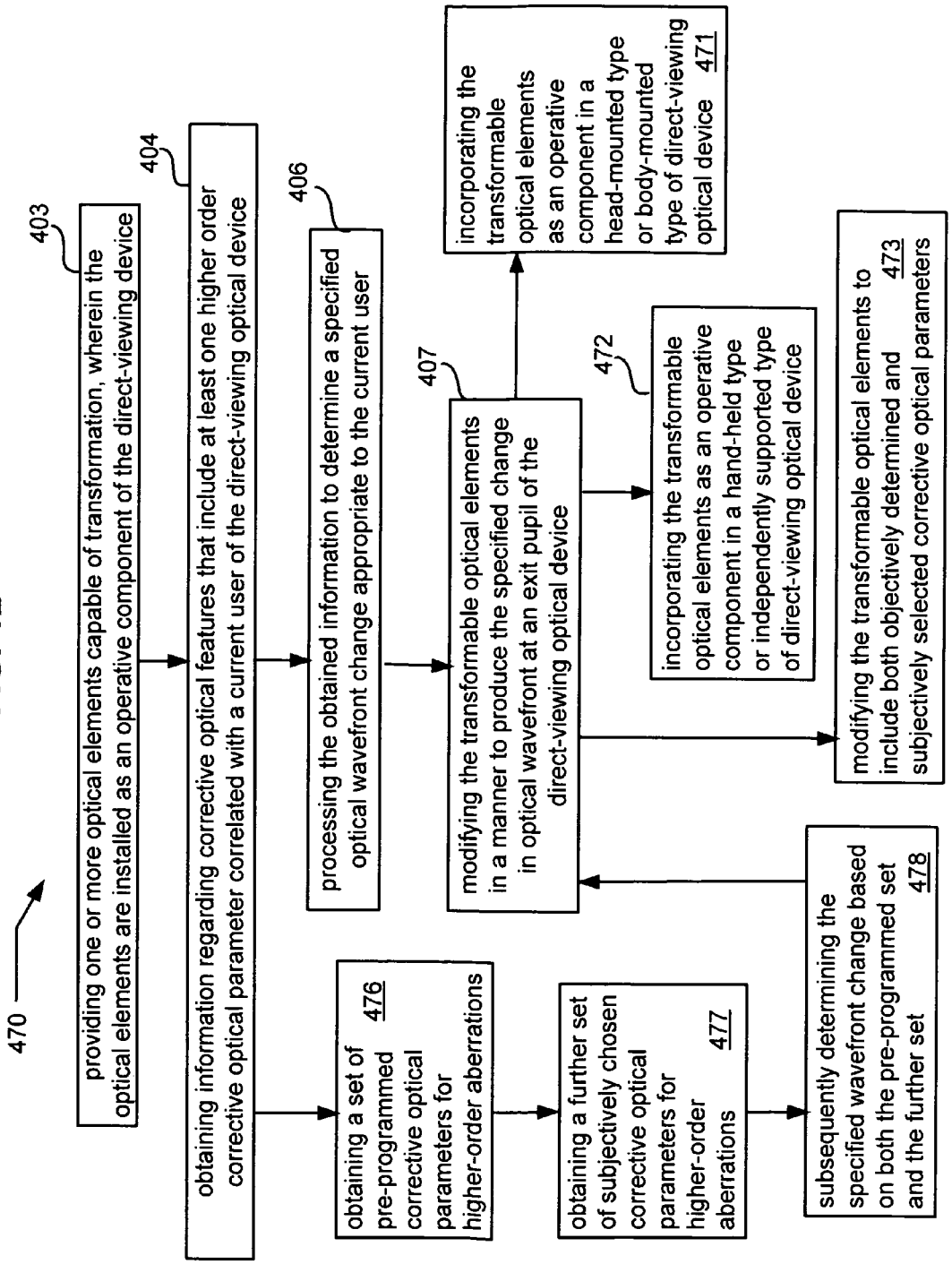

The detailed flow chart of FIG. 12 illustrates other embodiment features 470 including previously described process operations 403, 404, 406, 407 in combination with modifying the transformable optical elements to include both objectively determined and subjectively selected corrective optical parameters (block 473). Some exemplary embodiments may include incorporating the transformable optical elements as an operative component in a head-mounted type or body-mounted type of direct-viewing optical device (block 471). Other embodiments may include incorporating the transformable optical elements as an operative component in a hand-held type or independently supported type of direct-viewing optical device (block 472).

Additional related process aspects may include obtaining a set of pre-programmed corrective optical parameters for higher-order aberrations (block 476), and also obtaining a further set of subjectively chosen corrective optical parameters for higher-order aberrations (block 477), and subsequently determining the specified wavefront change based on both the pre-programmed set and the further set (block 478).

Figure 13:
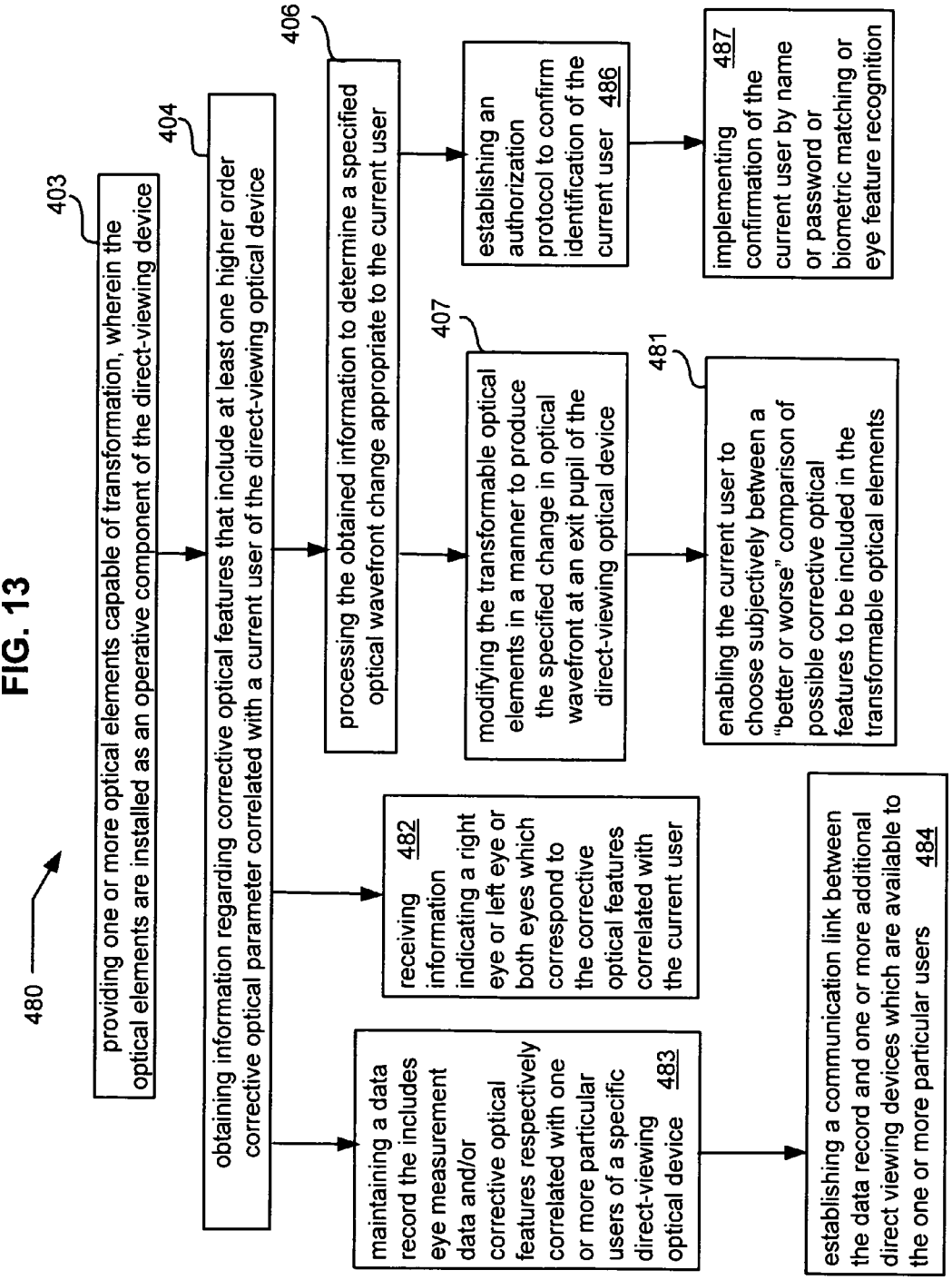

As illustrated in FIG. 13, various process features 480 may include previously described aspects 403, 404, 406, 407 as well as enabling the current user to choose subjectively between a "better or worse" comparison of possible corrective optical features to be included in the transformable optical elements (block 481). Another process aspect may include receiving information indicating a right eye or left eye or both eyes which correspond to the corrective optical features correlated with the current user (block 482).

Additional possible enhancements include maintaining a data record the includes eye measurement data and/or corrective optical features respectively correlated with one or more particular users of a specific direct-viewing optical device (block 483). A related exemplary feature includes establishing a communication link between the data record and one or more additional direct viewing devices which are available to the one or more particular users (block 484).

Also depicted in FIG. 13 are further process examples including establishing an authorization protocol to confirm identification of the current user (block 486), and implementing confirmation of the current user by name or password or biometric matching or eye feature recognition (block 487).

Figure 14:
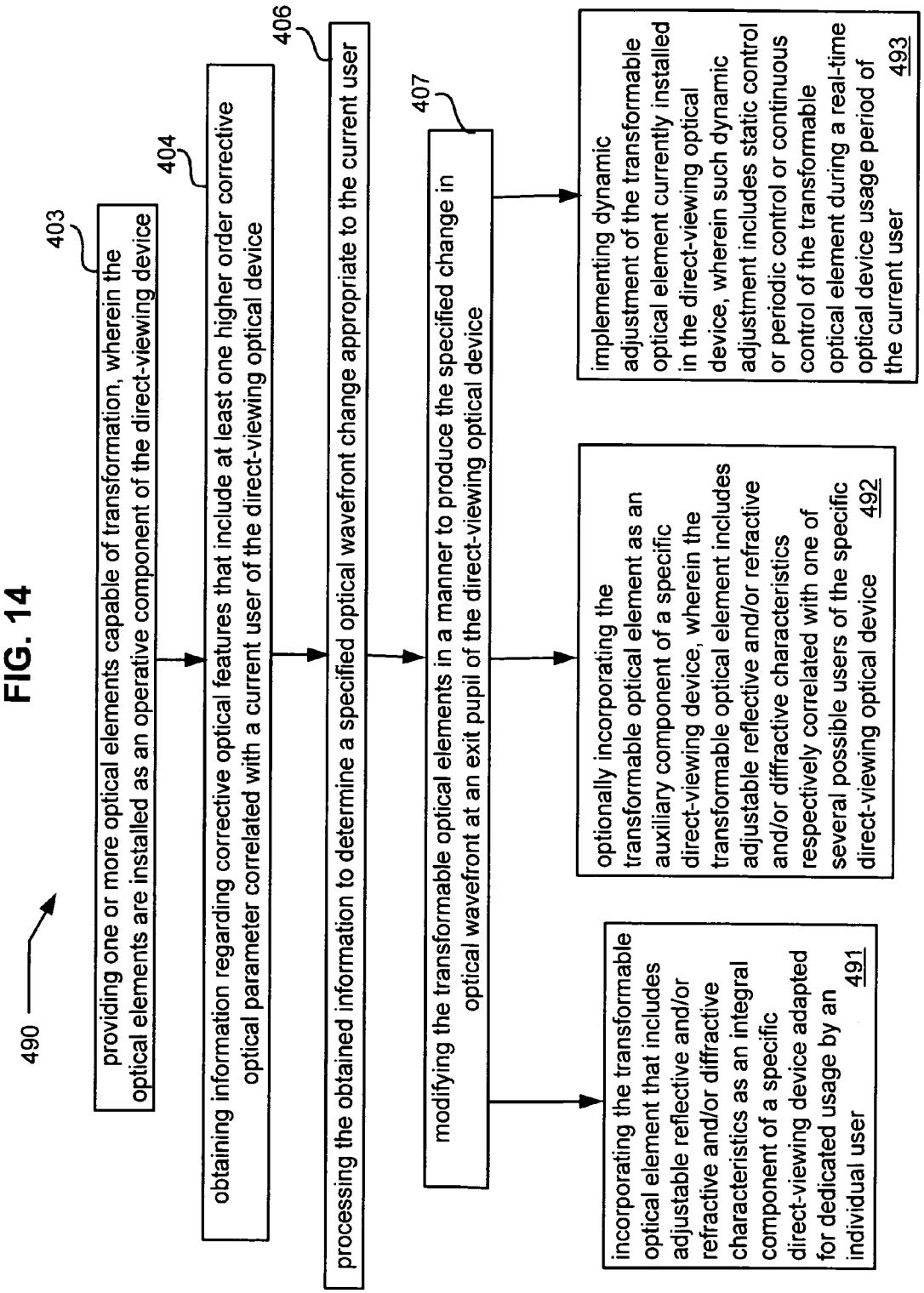

Referring to the detailed flow chart of FIG. 14, various exemplary process aspects 490 include previously described operations 403, 404, 406, 407 as well as incorporating the transformable optical element that includes adjustable reflective and/or refractive and/or diffractive characteristics as an integral component of a specific direct-viewing device adapted for dedicated usage by an individual user (block 491). Other process aspects may include optionally incorporating the transformable optical element as an auxiliary component of a specific direct-viewing device, wherein the transformable optical element includes adjustable reflective and/or refractive and/or diffractive characteristics respectively correlated with one of several possible users of the specific direct-viewing optical device (block 492).

Other process enhancements may include implementing dynamic adjustment of the transformable optical element currently installed in the direct-viewing optical device, wherein such dynamic adjustment includes static control or periodic control or continuous control of the transformable optical element during a real-time optical device usage period of the current user (block 493).

It will be understood from the exemplary embodiments disclosed herein that numerous individual method operations depicted in the flow charts of FIGS. 6-14 can be incorporated as encoded instructions in computer readable media in order to obtain enhanced benefits and advantages.

As another embodiment example, FIG. 15 shows a diagrammatic flow chart depicting an article of manufacture which provides computer readable media having encoded instructions for executing a corrective method for a direct-viewing optical device, wherein the method includes confirming identity of a current user of a direct-viewing optical device having one or more optical elements capable of transformation (block 503), obtaining information regarding corrective optical features that include at least one higher order corrective optical parameter correlated with the current user (block 504), and processing the obtained information to determine a specified optical wavefront change appropriate to the current user (block 506). Additional programmed aspects may include enabling modification of the transformable optical elements in a manner to produce the specified change in optical wavefront at an exit pupil of the direct-viewing optical device (block 507).

Another programmed method aspect may include activating a square or hexagonal matrix of sensors or actuators which transform a deformable reflective or refractive aspect of the one or more optical elements (block 508). Additional programmed method aspects may include enabling static control or periodic control or continuous control of the transformable optical elements during a real-time optical device usage period of the current user (block 509). In some instances a static control may provide a one-time setting per user (e.g., mechanically moved optical elements). In another instance a periodic control may refresh at intervals (e.g., liquid crystal phase modulator). In a further instance a continuous control must drive continuously (e.g., piezo-electric deformable mirror).

Further possible programmed aspects may include maintaining a data table or database that includes a listing of possible users and their respective optical aberrations and/or corrective optical parameters and/or preferences (block 511). As a further aspect responsive to the confirmed identity of the current user, a programmed method may include retrieving from the data table or database their respective optical aberrations or corrective optical parameters or preferences (block 512). Some programmed embodiments may include enabling modification of the transformable optical elements to include both objectively determined and subjectively selected corrective optical parameters (block 514).

Referring to the representative set of data table records 600 illustrated in FIG. 16, various categories of performance viewing factors 610 are listed, as for example, field of view 612, brightness 614, and scene contrast 618. Ongoing variations of such factors may require adjustment of corrective optical parameters to achieve better visual acuity for a particular current user of a direct-viewing optical device. Other categories of pertinent performance viewing factors that may require adjustment of corrective optical parameters 610 may include spatial frequency content 622 and spectral attributes 624, as well as a focal length of the optical device 626 and a current aperture stop 628. In some instances a variation of the diameter of a current user's pupil 632 may cause an adverse effect that diminishes visual acuity. In the absence of an indicated corrective preference by a current user that would be applicable to a particular monitored viewing factor, a generic default correction 632 may be automatically implemented.

Some data entries regarding corrective optical parameters may be respectively maintained for multiple prospective users of a device. For example, a separate corrective parameter listing is applicable to a user ID "Bill" during his usage of optical device XX (see 615), and another separate (and possibly different) corrective parameter listing is applicable during his usage of optical device YY (see 620). Another example shows a separate corrective parameter listing applicable to a user ID "Ann" during her usage of optical device XX (see 625). A further example shows a separate corrective parameter listing applicable to a user ID "Eva" during her usage of optical device YY (see 630), and another separate (and possible different) corrective parameter listing that is applicable to her usage of optical device ZZ (see 635).

Some performance viewing factors 610 may be ignored with respect to particular devices and/or for particular user IDs, depending on individual user preferences. For example, usage of device XX by user ID "Bill" and also by user ID "Ann" does not require any correlated corrective parameter with respect to any identified target object (see 642, 644). As another example, usage of device ZZ by user ID "Eva" does not require any correlated corrective parameter with respect to any particular field of view (see 646), or with respect to variable spectral attributes (see 647). As a further example, usage of device YY by user ID "Bill" and also by user ID "Eva" does not require any correlated corrective parameters with respect to monitoring a user's pupil diameters (see 648, 649).

It will be understood that the categories and informational entries shown in the data table records of FIG. 16 are for purposes of illustration only, and may be expanded or altered in some embodiments and may be shortened or omitted in other embodiments depending on the circumstances.

Figure 17:
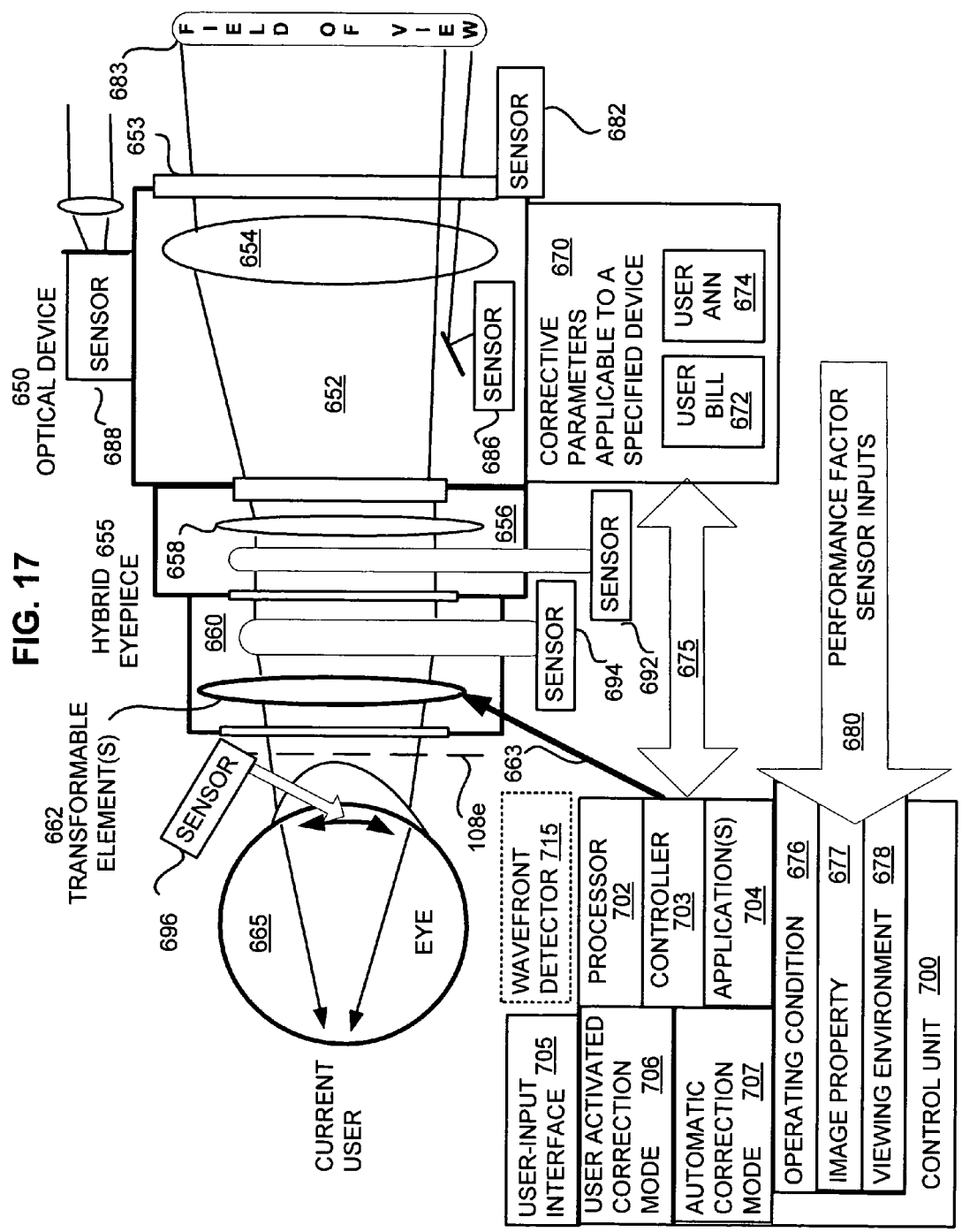
FIG. 17 is a schematic block diagram illustrating various aspects of obtaining and processing different types of optical device viewing parameters.

The schematic block diagram of FIG. 17 illustrates an embodiment for optical device 650 having a body portion 652 that includes aperture 653, other optical elements (e.g., refractive element 654) for viewing a particular field of view 683. The exemplary optical device 650 also includes a hybrid eyepiece 655 having a first eyepiece portion 656 with various optical elements (e.g., see refractive element 658), and a second eyepiece portion 660 with one or more transformable elements (e.g., see 662).

Also associated with optical device 650 is an exemplary data record 670 for corrective parameters applicable to a specified device. A separate listing of such corrective parameters may be respectively maintained for individual users of the specified optical device 650 (e.g., see user Bill 672, user Ann 674). The data record 670 is available for both "read" and "write" access through connecting link 675 to control unit 700 to enable processing of known and/or updated information that is necessary for adjusting the transformable elements 662 during a period of usage by an identified current user. An operatively coupled communication channel (e.g., see line 663) provides the static control or periodic control or continuous control of the transformable elements 662 in accordance with automatic and/or optional customized adjustment parameters initiated by the control unit 700.

The exemplary control unit 700 includes processor 702, controller 703, one or more applications 704, user-input interface 705, and in some instances may include a wavefront detector 715. It will be understood that real-time optical adjustments may be implemented pursuant to circuitry and/or software programming for an automatic correction mode 707 or a user activated correction mode 706 regarding transformable elements 662. It is therefore possible to provide a specified real-time change in optical wavefront at an exit pupil (e.g., see approximate exit pupil plane 108e) based on both objective implementation and/or subjective selection of corrective optical parameters to ameliorate low-order and/or high-order aberrations of a current user of the optical device 650.

Various sensors are symbolically shown (see 682, 686, 688, 692, 694) for monitoring and obtaining required measurements etc. that are indicative of the ongoing performance viewing factors during a current usage period of the optical device 650. An additional sensor 696 may be configured to determine a pupil diameter of a current user's eye 665 during the usage period. The various performance factor sensor outputs (e.g., see 680) are transmitted to the control unit 700 for real-time processing in order to achieve dynamic adjustment of the transformable elements 662. As indicated on the data table records 600 of FIG. 16, it may be helpful to provide different adjustment guidelines depending on the viewing parameter topics. In that regard sensor input data may be segregated for appropriated processing into different categories such as operating condition data 676, image properties 677, and viewing environment data 678.

Figure 18:
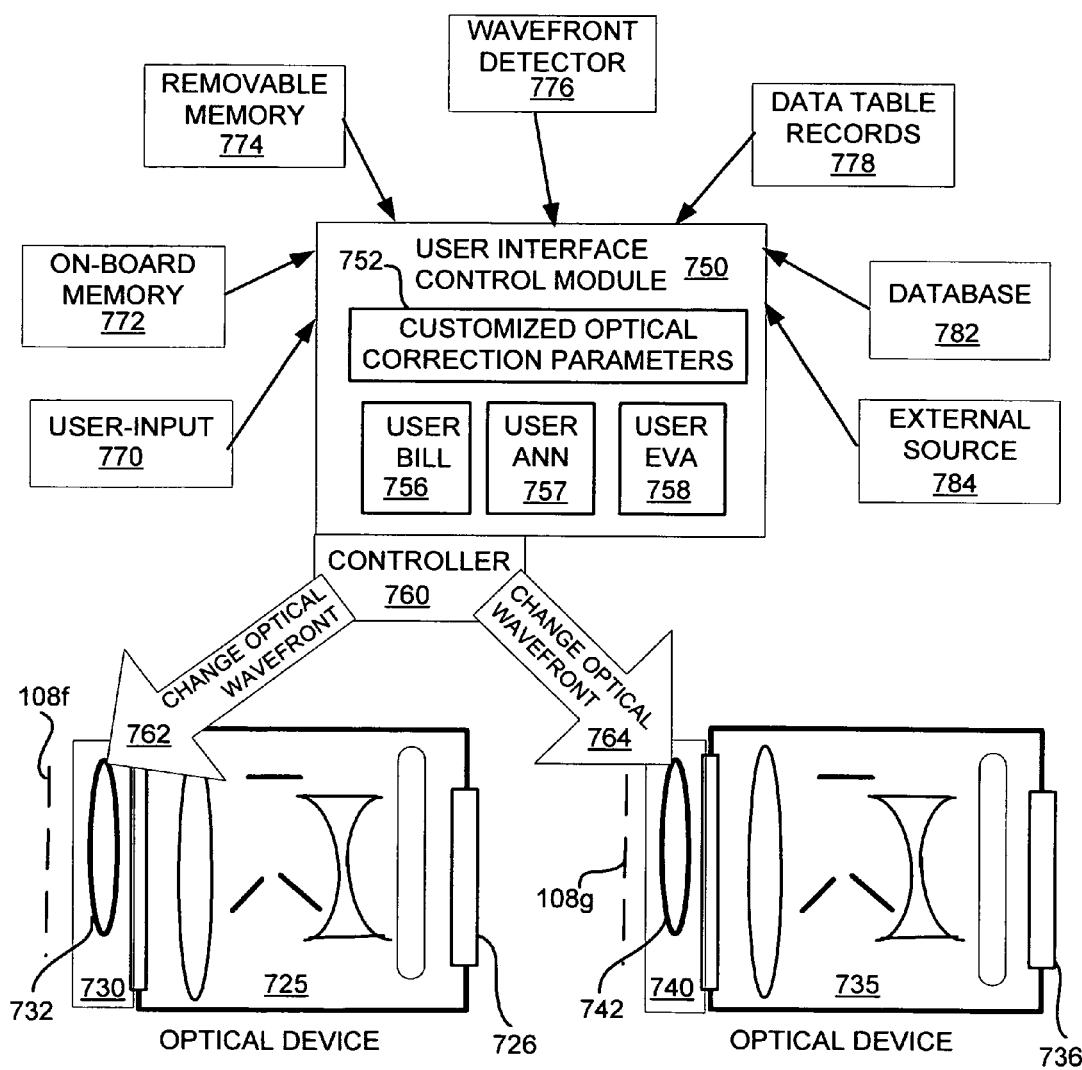
FIG. 18 is a schematic block diagram showing examples of data processing techniques for adjusting transformable optical elements in different optical devices.

Referring to the schematic block diagram of FIG. 18, various possible data processing techniques may be implemented with a user interface control module 750 with regard to customized optical correction parameters 752 related to user Bill 756, user Ann 757, and user Eva 758. Informational data regarding eye measurements and/or low/high order aberrations and/or corrective optical parameters for a prospective or current device user may be accessible to the user interface control module 750. For example, known data may be obtained from an external source 784, or a database 782, or data table records 778. Additional availability of such informational data may be obtained from user-input 770, on-board memory 772, or removable memory 774. In some instances newly updated information data may be obtained from a wavefront detector 776 directly associated with the optical direct-viewing device.

It will be understood that the illustrated interface control module 750 includes controller 760 that generates a first control signal 762 for changing an optical wavefront at an exit pupil (e.g., see approximate exit pupil plane 108f) pursuant to a real-time adjustment of transformable optical element(s) 732. Such a real-time customized adjustment provides enhanced acuity for a current user's view through aperture 726 of direct-viewing optical device 725. Similarly the illustrated controller 760 generates a second control signal 764 for changing an optical wavefront at an exit pupil (e.g., see approximate exit pupil plane 108g) pursuant to a real-time adjustment of transformable optical element(s) 742. Such a real-time customized adjustment provides enhanced acuity for another current user's view through aperture 736 of direct-viewing optical device 735.

Figure 19:
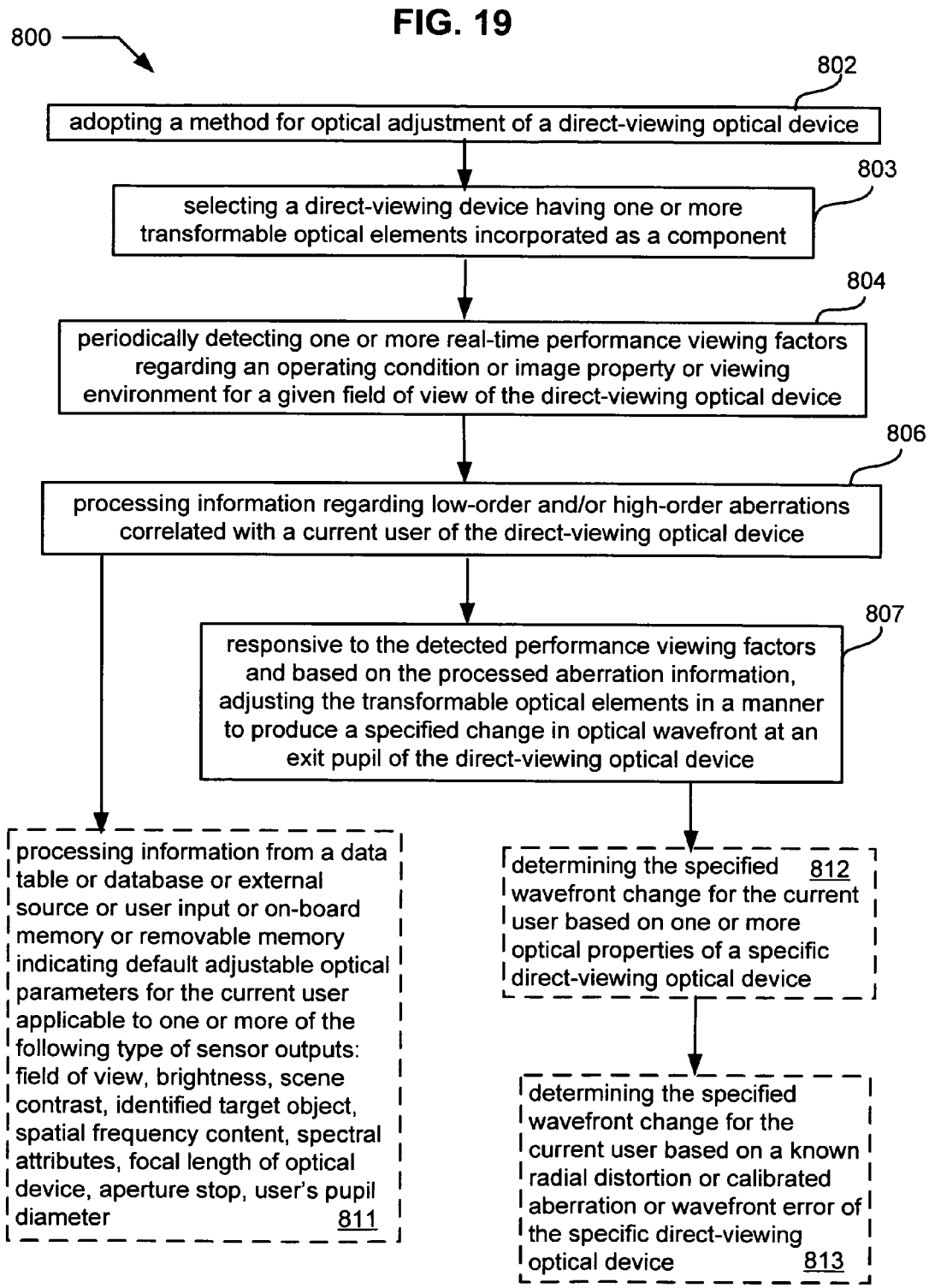
FIG. 19 is a high level flow chart showing exemplary method aspects regarding optical corrections based on optical device viewing parameters.

The high level flow chart of FIG. 19 illustrates exemplary embodiment features 800 regarding adoption of an optical adjustment method for a direct-viewing optical device (see block 802), including selecting a direct-viewing device having one or more transformable optical elements incorporated as a component (block 803), periodically detecting one or more real-time performance viewing factors regarding an operating condition or image property or viewing environment for a given field of view of the direct-viewing optical device (block 804), and processing information regarding low-order and/or high-order aberrations correlated with a current user of the direct-viewing optical device (block 806). Related process features that are responsive to the detected performance viewing factors and are based on the processed aberration information include adjusting the transformable optical elements in a manner to produce a specified change in optical wavefront at an exit pupil of the direct-viewing optical device (block 807).

Additional process aspects may include processing information from a data table or database or external source or user input or on-board memory or removable memory indicating default adjustable optical parameters for the current user applicable to one or more of the following type of sensor outputs: field of view, brightness, scene contrast, identified target object, spatial frequency content, spectral attributes, focal length of optical device, aperture stop, user's pupil diameter (block 811). Other examples include determining the specified wavefront change for the current user based on one or more optical properties of a specific direct-viewing optical device (block 812), and in some instances determining the specified wavefront change for the current user based on a known radial distortion or calibrated aberration or wavefront error of the specific direct-viewing optical device (block 813).

Figure 20:
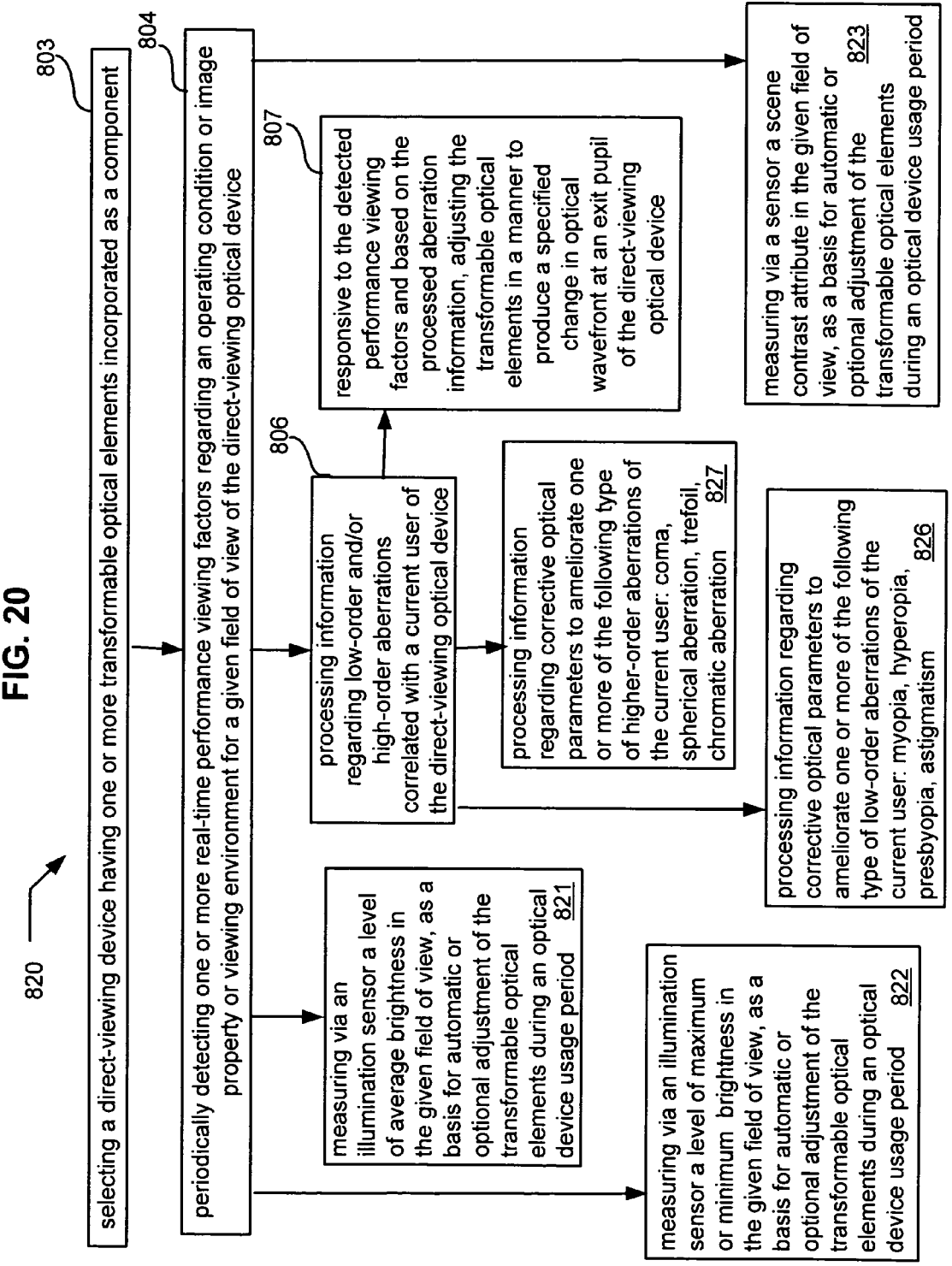
FIGS. 20-28 are detailed flow charts illustrating additional exemplary method aspects applicable to optical device viewing parameters.

Referring to the illustrated process examples 820 depicted in the flow chart of FIG. 20, an embodiment may include previously described aspects 803, 804, 806, 807 along with processing information regarding corrective optical parameters to ameliorate one or more of the following type of low-order aberrations of the current user: myopia, hyperopia, presbyopia, astigmatism (block 826). Another process example includes processing information regarding corrective optical parameters to ameliorate one or more of the following type of higher-order aberrations of the current user: coma, spherical aberration, trefoil, chromatic aberration (block 827).

Further possibilities include measuring via an illumination sensor a level of average brightness in the given field of view, as a basis for automatic or optional adjustment of the transformable optical elements during an optical device usage period (block 821). Another possible aspect includes measuring via an illumination sensor a level of maximum or minimum brightness in the given field of view, as a basis for automatic or optional adjustment of the transformable optical elements during an optical device usage period (block 822). A further process example includes measuring via a sensor a scene contrast attribute in the given field of view, as a basis for automatic or optional adjustment of the transformable optical elements during an optical device usage period (block 823).

Figure 21:
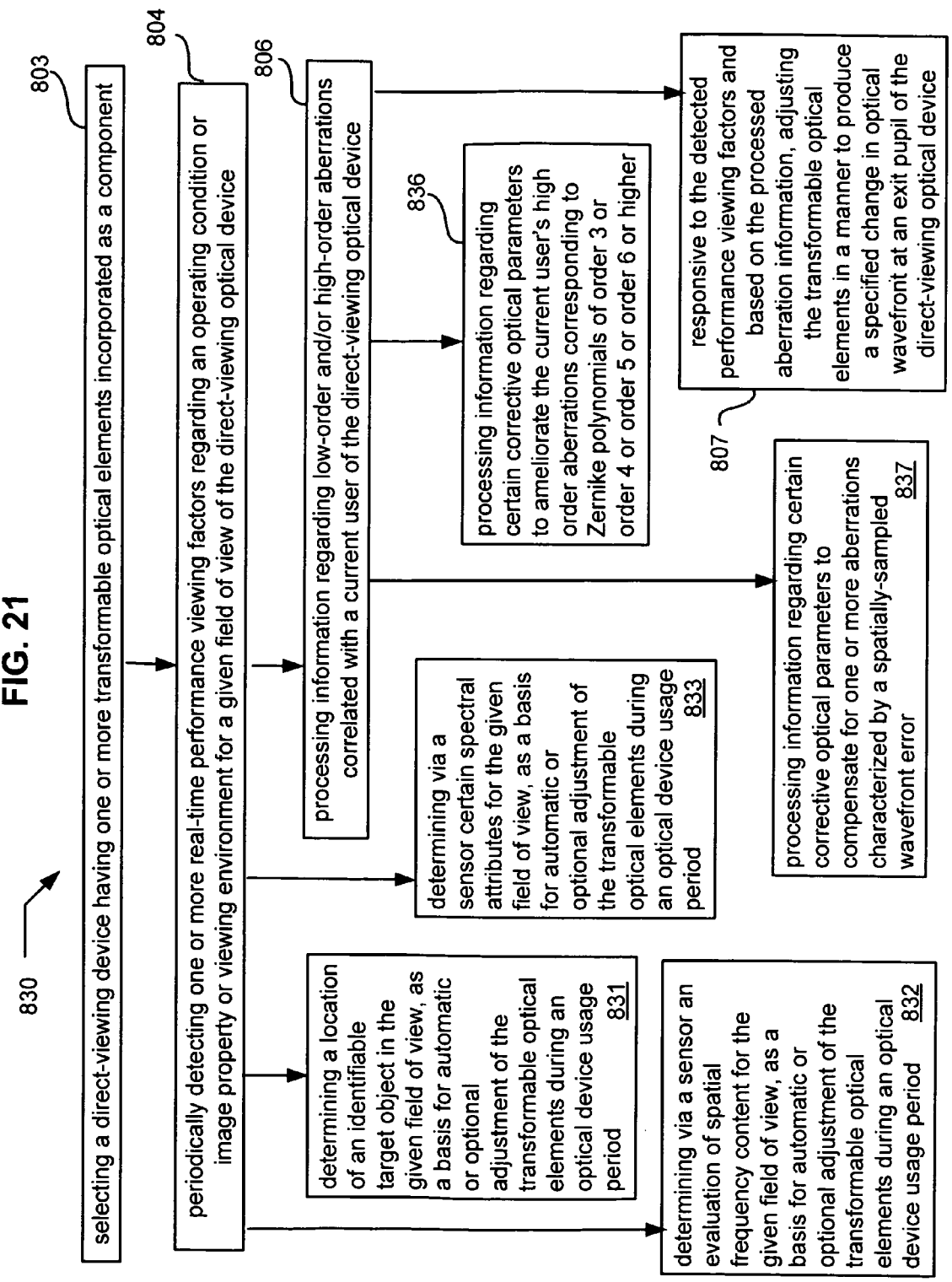

Referring to the detailed flow chart of FIG. 21, various illustrated embodiment features 830 include previously described aspects 803, 804, 806, 807 as well as additional examples such as determining a location of an identifiable target object in the given field of view, as a basis for automatic or optional adjustment of the transformable optical elements during an optical device usage period (block 831). Another example includes determining via a sensor an evaluation of spatial frequency content for the given field of view, as a basis for automatic or optional adjustment of the transformable optical elements during an optical device usage period (block 832).

In some instances an exemplary process includes determining via a sensor certain spectral attributes for the given field of view, as a basis for automatic or optional adjustment of the transformable optical elements during an optical device usage period (block 833). Another possibility includes processing information regarding certain corrective optical parameters to ameliorate the current user's high order aberrations corresponding to Zernike polynomials of order 3 or order 4 or order 5 or order 6 or higher (block 836). A further possible aspect includes processing information regarding certain corrective optical parameters to compensate for one or more aberrations characterized by a spatially-sampled wavefront error (block 837).

Figure 22:
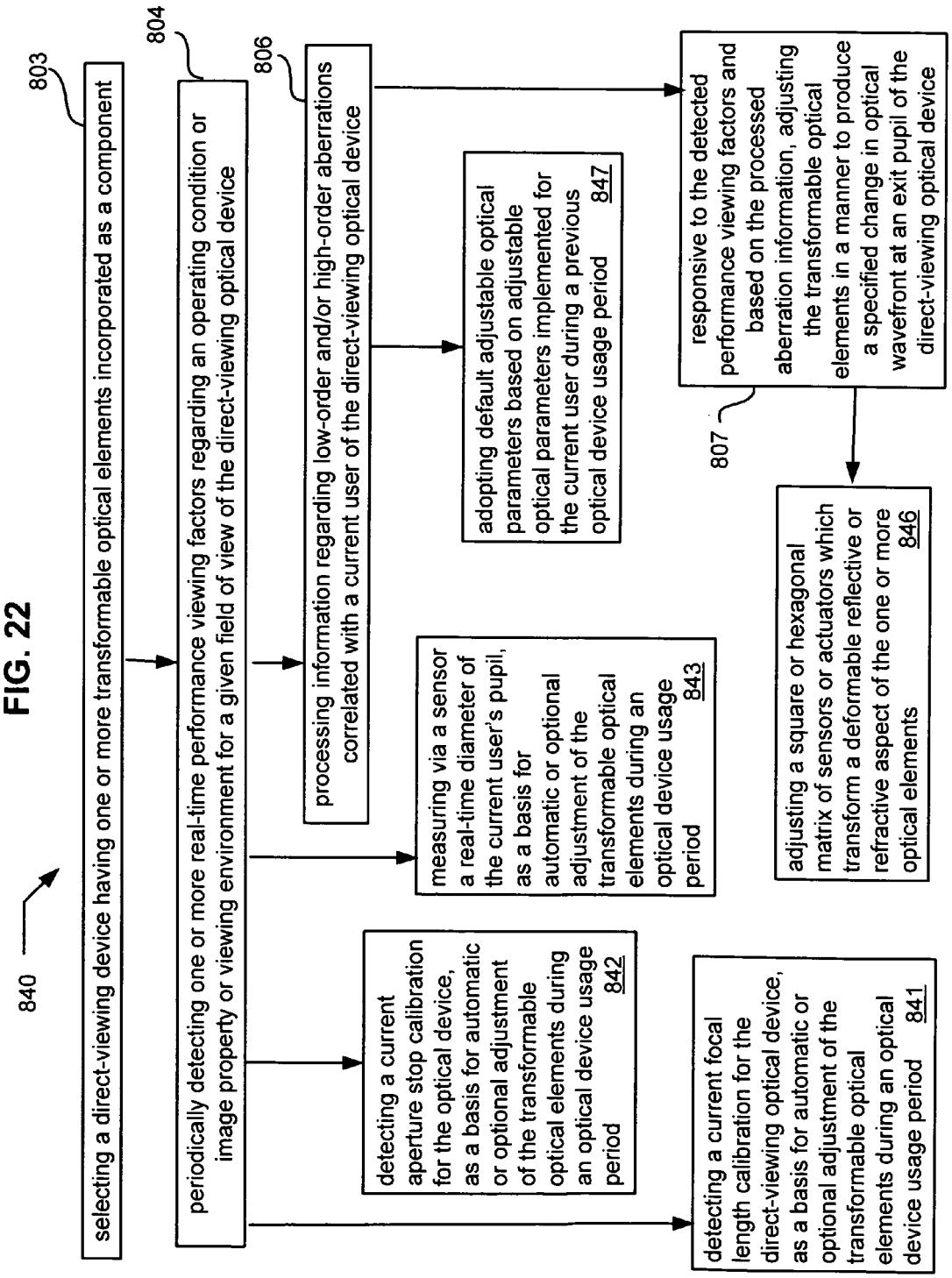

The exemplary process aspects 840 illustrated in FIG. 22 include previously described operations 803, 804, 806, 807 in combination with detecting a current focal length calibration for the direct-viewing optical device, as a basis for automatic or optional adjustment of the transformable optical elements during an optical device usage period (block 841). Another process feature may include detecting a current aperture stop calibration for the optical device, as a basis for automatic or optional adjustment of the transformable optical elements during an optical device usage period (block 842).

Another illustrated example includes measuring via a sensor a real-time diameter of the current user's pupil, as a basis for automatic or optional adjustment of the transformable optical elements during an optical device usage period (block 843). Further possibilities may include adjusting a square or hexagonal matrix of sensors or actuators which transform a deformable reflective or refractive aspect of the one or more optical elements (block 846). In some instances an example may include adopting the default adjustable optical parameters based on adjustable optical parameters implemented for the current user during a previous optical device usage period (block 847).

Figure 23:
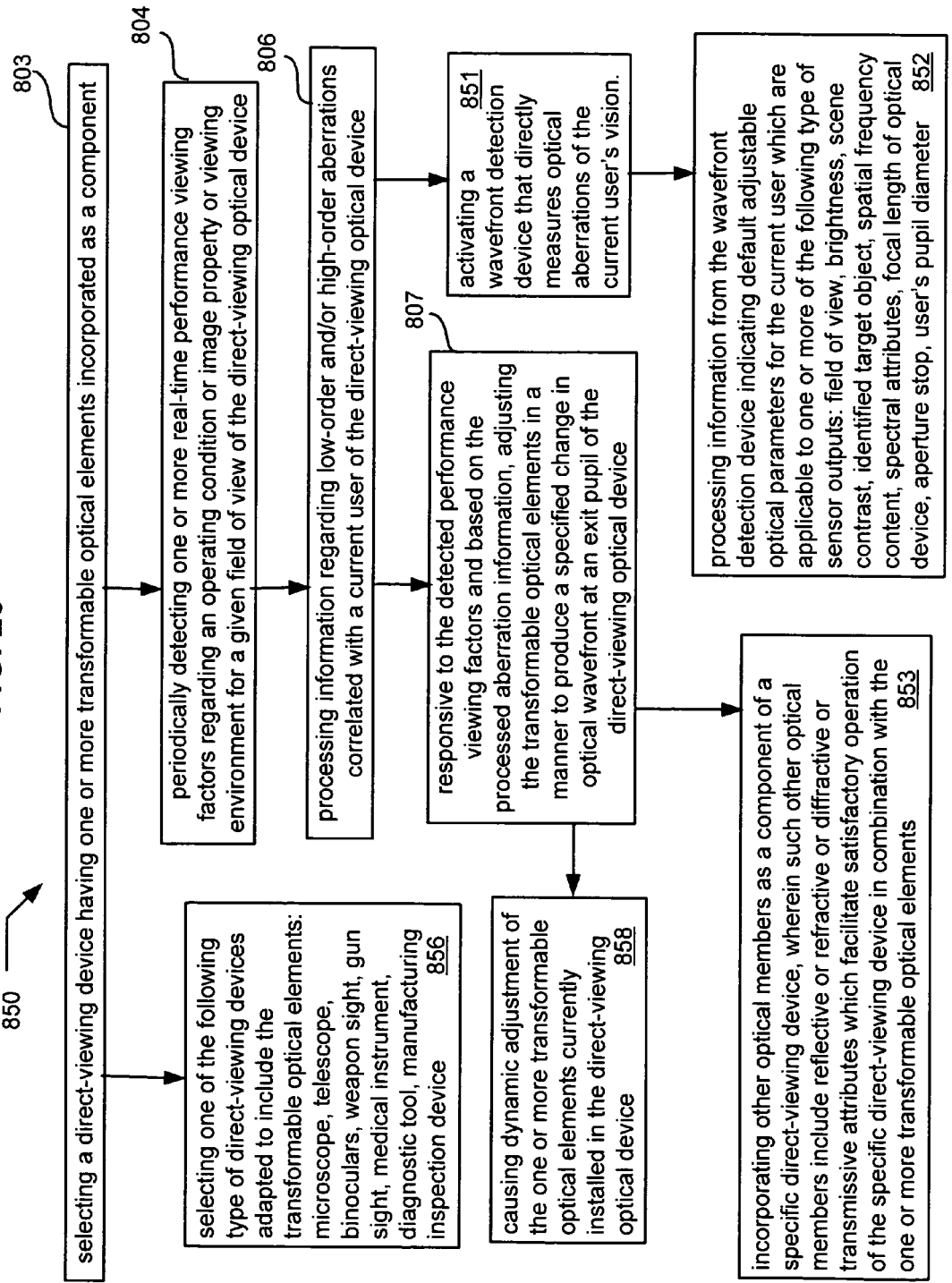

The detailed flow chart of FIG. 23 illustrates exemplary embodiment features 850 that include previously described aspects 803, 804, 806, 807 as well as activating a wavefront detection device that directly measures optical aberrations of the current user's vision (block 851). Related illustrated aspects include processing information from the wavefront detection device indicating default adjustable optical parameters for the current user which are applicable to one or more of the following type of sensor outputs: field of view, brightness, scene contrast, identified target object, spatial frequency content, spectral attributes, focal length of optical device, aperture stop, user's pupil diameter (block 852).

In some instances an enhancement may include incorporating other optical members as a component of a specific direct-viewing device, wherein such other optical members include reflective or refractive or diffractive or transmissive attributes which facilitate satisfactory operation of the specific direct-viewing device in combination with the one or more transformable optical elements (block 853). Other enhancements may include causing dynamic adjustment of the one or more transformable optical elements currently installed in the direct-viewing optical device (block 858).

Figure 24:
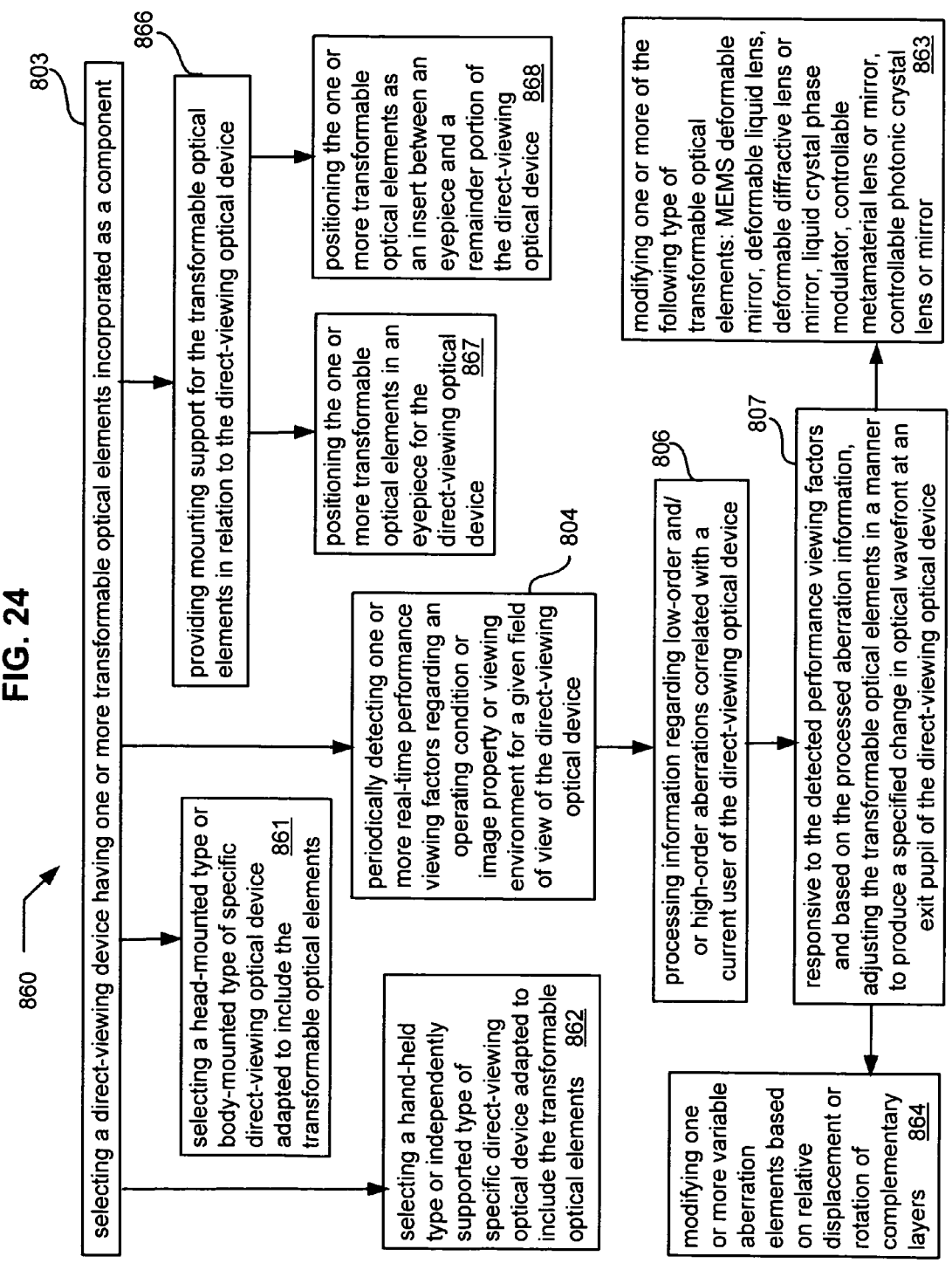

The detailed flow chart of FIG. 24 shows exemplary process aspects 860 that include previously described features 803, 804, 806, 807 in combination with selecting a head-mounted type or body-mounted type of specific direct-viewing optical device adapted to include the transformable optical elements (block 861), or in some instances in combination with selecting a hand-held type or independently supported type of specific direct-viewing optical device adapted to include the transformable optical elements (block 862).

Further process examples include modifying one or more of the following type of transformable optical elements: MEMS deformable mirror, deformable liquid lens, deformable diffractive lens or mirror, liquid crystal phase modulator, controllable metamaterial lens or mirror, controllable photonic crystal lens or mirror (block 863). Another process example includes modifying one or more variable aberration elements based on relative displacement or rotation of complementary layers (block 864).

As further illustrated in FIG. 24, other process examples include providing mounting support for the transformable optical elements in relation to the direct-viewing optical device (block 866), and in some instances positioning the one or more transformable optical elements in an eyepiece for the direct-viewing optical device (block 867). Another example includes positioning the one or more transformable optical elements as an insert between an eyepiece and a remainder portion of the direct-viewing optical device (block 868).

Figure 25:
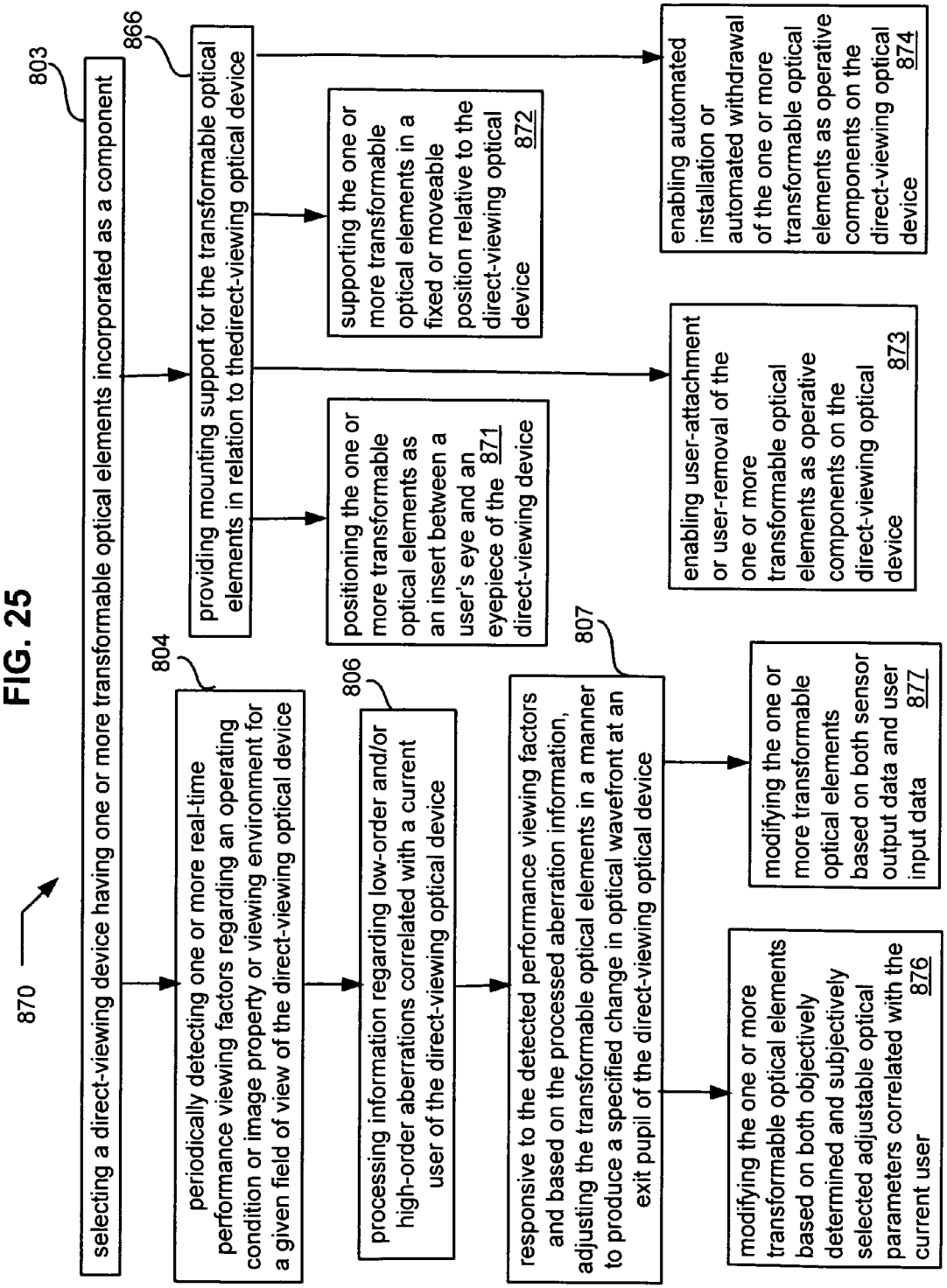

With regard to the exemplary process aspects 870 shown in FIG. 25, a possible embodiment may include previously described features 803, 804, 806; 807, 866 along with positioning the one or more transformable optical elements as an insert between a user's eye and an eyepiece of the direct-viewing device (block 871). Another possibility includes supporting the one or more transformable optical elements in a fixed or moveable position relative to the direct-viewing optical device (block 872).

A further possible aspect includes enabling user-attachment or user-removal of the one or more transformable optical elements as operative components on the direct-viewing optical device (block 873). Some enhancements may include enabling automated installation or automated withdrawal of the one or more transformable optical elements as operative components on the direct-viewing optical device (block 874).

Another possible aspect includes modifying the one or more transformable optical elements based on both objectively determined and subjectively selected adjustable optical parameters correlated with the current user (block 876). A further possibility includes modifying the one or more transformable optical elements based on both sensor output data and user input data (block 877).

Figure 26:
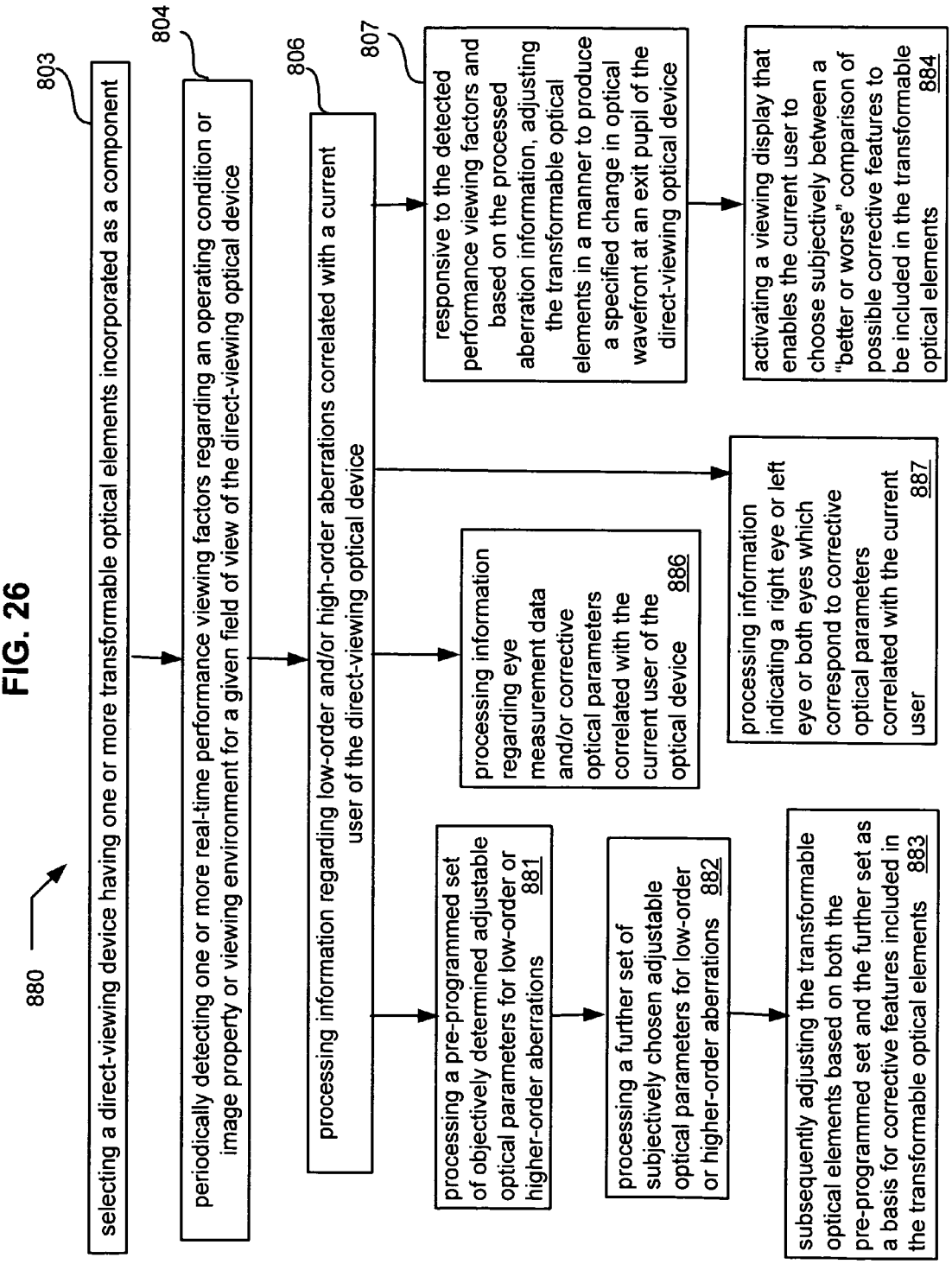

The flow chart of FIG. 26 relates to additional exemplary process features 880 that include previously described aspects 803, 804, 806, 807 along with activating a viewing display that enables the current user to choose subjectively between a "better or worse" comparison of possible corrective features to be included in the transformable optical elements.

Other illustrated process features 950 may include processing a pre-programmed set of objectively determined adjustable optical parameters for low-order or higher-order aberrations (block 881), and also processing a further set of subjectively chosen adjustable optical parameters for low-order or higher-order aberrations (block 882), and subsequently adjusting the transformable optical elements based on both the pre-programmed set and the further set as a basis for corrective features included in the transformable optical elements (block 883).

Additional aspects illustrated in FIG. 26 include processing information regarding eye measurement data and/or corrective optical parameters correlated with the current user of the optical device (block 886). Further possibilities include processing information indicating a right eye or left eye or both eyes which correspond to corrective optical parameters correlated with the current user (block 887).

Figure 27:
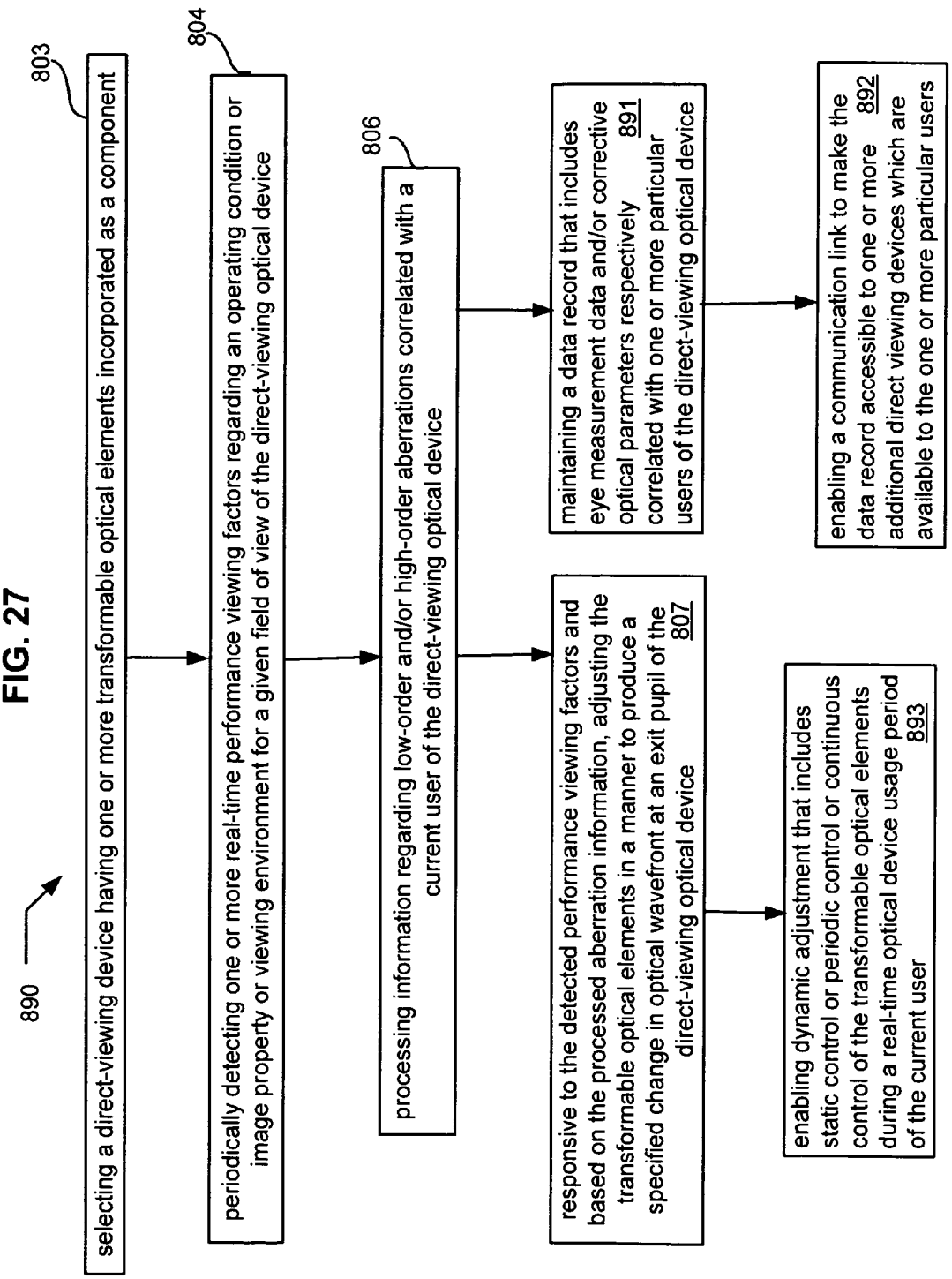

Referring to the detailed flow chart of FIG. 27, various exemplary process embodiment features 890 include previously described aspects 803, 80, 806, 807 in combination with maintaining a data record that includes eye measurement data and/or corrective optical parameters respectively correlated with one or more particular users of the direct-viewing optical device (block 891). A related process example includes enabling a communication link to make the data record accessible to one or more additional direct viewing devices which are available to the one or more particular users (block 892).

Another example includes enabling dynamic adjustment that includes static control or periodic control or continuous control of the transformable optical elements during a real-time optical device usage period of the current user (block 893).

Figure 28:
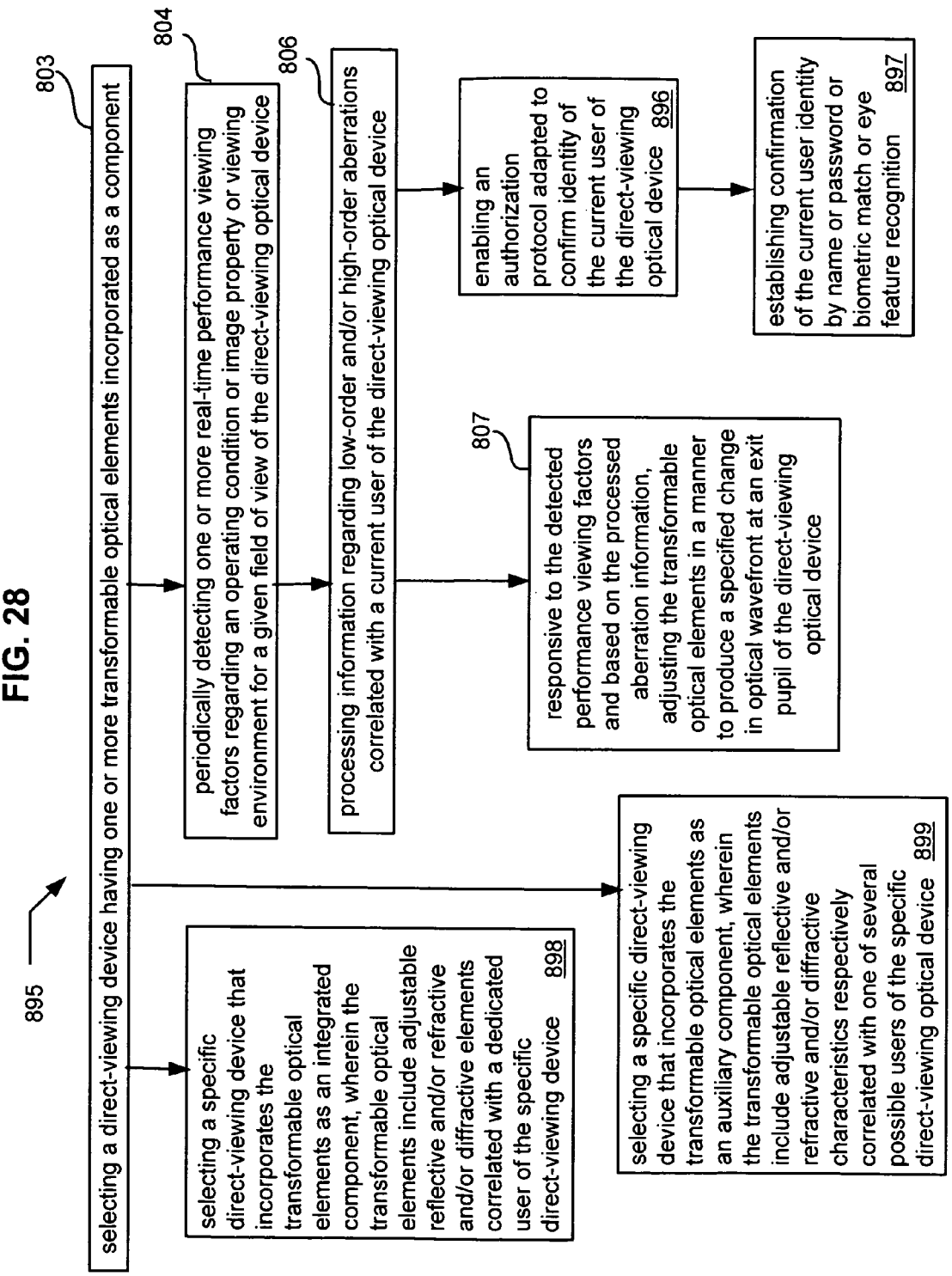

The detailed flow chart of FIG. 28 illustrates various exemplary process aspects 895 including previously described operations 803, 804, 806, 807 as well as enabling an authorization protocol adapted to confirm identity of the current user of the direct-viewing optical device (block 896). A related process aspect may include establishing confirmation of the current user identity by name or password or biometric match or eye feature recognition (block 897).

Some embodiments may further include selecting a specific direct-viewing device that incorporates the transformable optical elements as an integrated component, wherein the transformable optical elements include adjustable reflective and/or refractive and/or diffractive elements correlated with a dedicated user of the specific direct-viewing device (block 898). Another possible embodiment may include selecting a specific direct-viewing device that incorporates the transformable optical elements as an auxiliary component, wherein the transformable optical elements include adjustable reflective and/or refractive and/or diffractive characteristics respectively correlated with one of several possible users of the specific direct-viewing optical device (block 899).

It will be understood from the exemplary embodiments disclosed herein that numerous individual method operations depicted in the flow charts of FIGS. 19-28 can be incorporated as encoded instructions in computer readable media in order to obtain enhanced benefits and advantages.

Figure 29:
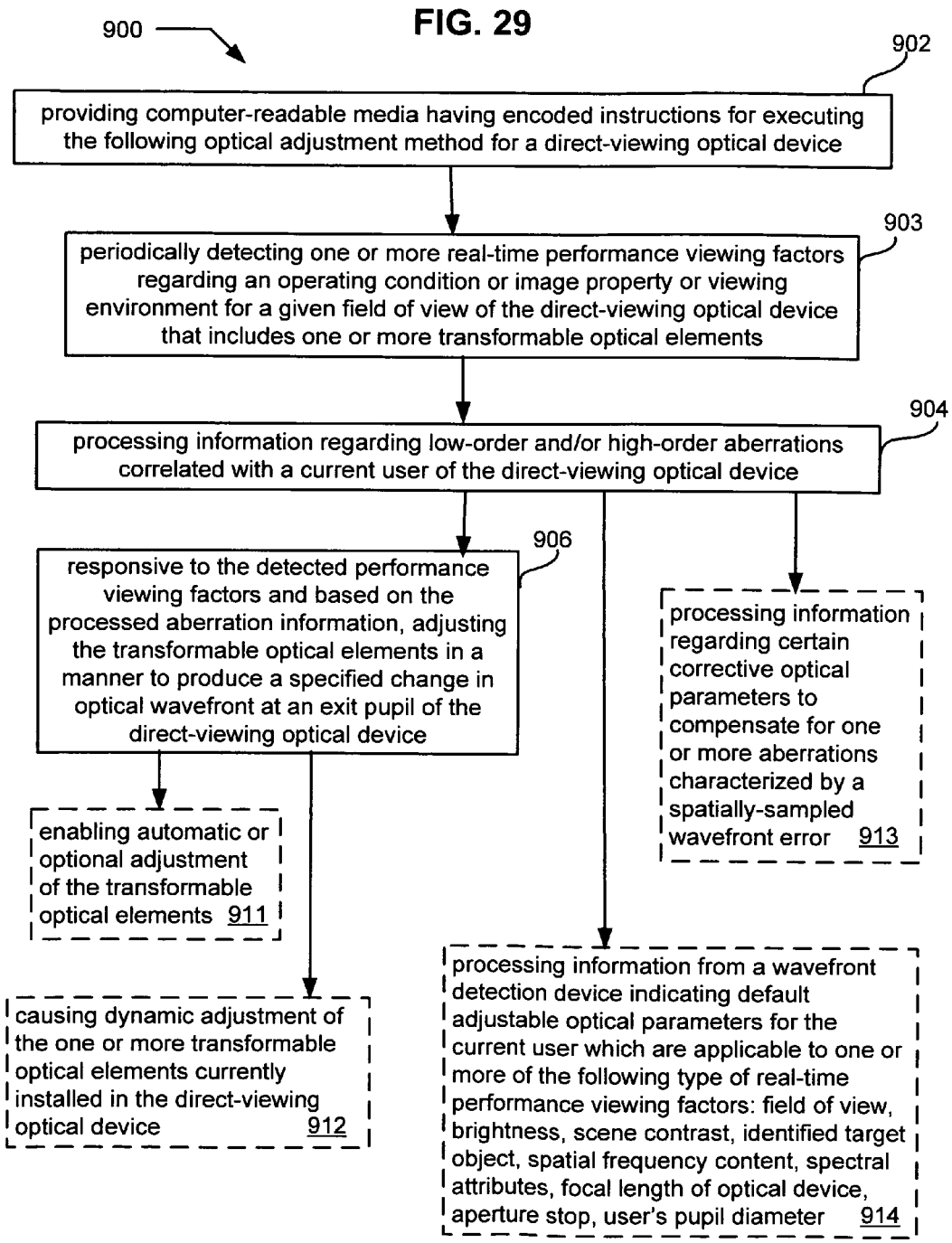
FIG. 29 is a diagrammatic flow chart for further exemplary computer-readable media embodiment features.

As another embodiment example, FIG. 29 shows a diagrammatic flow chart depicting an article of manufacture which provides computer-readable media having encoded instructions for executing an optical adjustment method for a direct-viewing optical device (block 902), wherein the method includes periodically detecting one or more real-time performance viewing factors regarding an operating condition or image property or viewing environment for a given field of view of the direct-viewing optical device that includes one or more transformable optical elements (block 903); processing information regarding low-order and/or high-order aberrations correlated with a current user of the direct-viewing optical device (block 904); and responsive to the detected performance viewing factors and based on the processed aberration information, adjusting the transformable optical elements in a manner to produce a specified change in optical wavefront at an exit pupil of the direct-viewing optical device (block 906).

Other possible programmed aspects include enabling automatic or optional adjustment of the transformable optical elements (block 911), and in some instances causing dynamic adjustment of one or more transformable optical elements currently installed in the direct-viewing optical device (block 912). Another example of a programmed aspect includes processing information regarding certain corrective optical parameters to compensate for one or more aberrations characterized by a spatially-sampled wavefront error (block 913). Further programmed method aspects may include processing information from the wavefront detection device indicating default adjustable optical parameters for the current user which are applicable to one or more of the following type of real-time performance viewing factors: field of view, brightness, scene contrast, identified target object, spatial frequency content, spectral attributes, focal length of optical device, aperture stop, user's pupil diameter (block 914).

Figure 30:
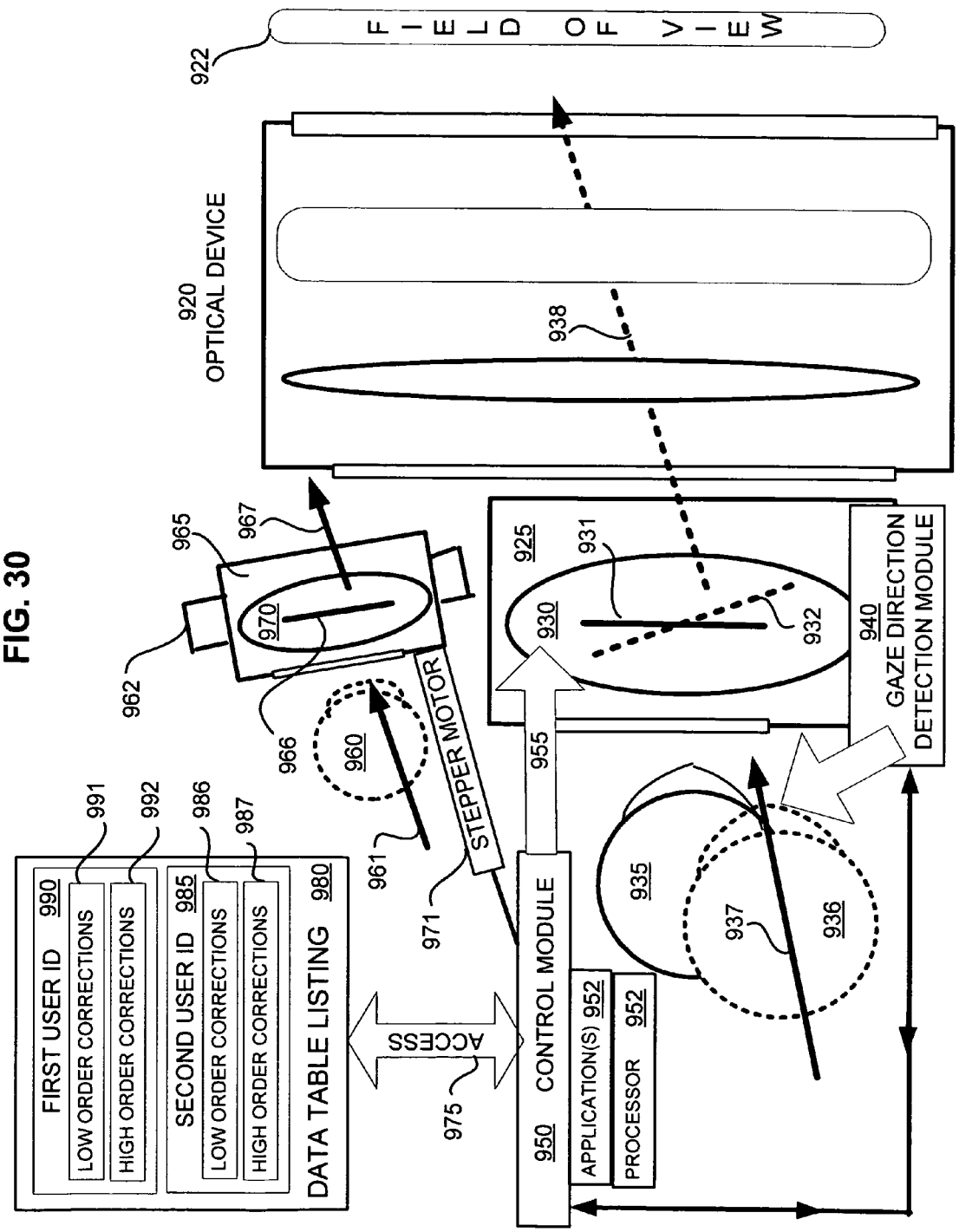
FIG. 30 is a schematic block diagram illustrating adjustable optical enhancements based on tracked gaze directions of a current user of a direct-viewing optical device.

The schematic block diagram of FIG. 30 illustrates an exemplary embodiment for an alignment optical correction system for a direct-viewing optical device 920 having a field of view 922. A customizable eyepiece 925 having a one or more transformable optical elements 930 is optically coupled with the optical device 920 for conventional viewing by a current user's eye 935. A solid line 931 indicates a reference that is perpendicular to an initial gaze direction of the eye 935. Sometimes a current user's gaze direction shifts (e.g., see eye 936) in a way that results in a changed optical path through the direct-viewing optical device 920 toward the field of view 922. A gaze direction detection module 940 is operatively coupled to control module 950 in order to transmit a monitored changed of the gaze direction of eye 936. This shifted gaze direction may adversely affect the acuity for visual objects in the field of view 922.

In response to the shifted gaze direction, an example of a first corrective operational response mode enables a control module 950 to send a control signal via communication channel 955 to the transformable optical elements 930 in order to cause an optical realignment of a central viewing axis of correction parameters relative to the shifted gaze direction 967 of eye 936. Such optical realignment is shown symbolically on FIG. 30 by revised dotted reference line 932 perpendicular to a new central viewing axis (see dotted arrow 938) of transformable optical elements 930.

It will be noted that control module 950 includes a processor 952 and one or more applications 952 for appropriate data processing to establish both an original adjustment of the transformable optical elements (i.e., based on wavefront aberrations associated with a current user), as well as an optical realignment of the transformable optical elements (i.e., based on the detected shift of the gaze direction). This first corrective operational response mode allows the customizable eyepiece 925 and its attached optical elements (e.g., 930) to remain in their usual fixed position attached to the optical device 920.

In response to the shifted gaze direction, an example of a second corrective operational response mode enables the control module 950 to send a control signal via another communication channel to stepper motor 971. As shown in an alternate view of a customizable eyepiece 965, the stepper motor 971 (or other motorized component) causes an automatic physical translation and/or rotation of the customizable eyepiece 965 and its attached optical elements (e.g., 970) on a pivotal base 962 to achieve a new physical realignment of the eyepiece 925 relative to the shifted gaze direction 961 of eye 960. Such physical realignment is shown symbolically on FIG. 30 by reference line 966 perpendicular to new central viewing axis (see arrow 967).

In some embodiments one or more of the attached optical elements (e.g., 970) may be separately configured to be physically repositioned via an adjustable mounting base (not shown) in response to the shifted gaze direction, while a supportive eyepiece body portion remains attached in a fixed position relative to the optical device 920. Optional manual repositioning may be another alternative in some embodiments, although calibrated precision control of such manual repositioning may be more difficult to achieve.

The control module 950 is operably coupled via access channel 975 to a data table listing 980 that includes information regarding optical aberrations of one or more prospective users of direct-viewing device 920. For example, data associated with a first user ID 990 may include low-order corrections 991 as well as high-order corrections 992. As another example, data associated with a second user ID 985 may include low-order corrections 986 as well as high-order corrections 987.

In some embodiments it may be desirable in implement both the first corrective operational response mode (i.e., optical transformation of the installed transformable optical elements) and also the second corrective operational response mode (i.e., physical realignment of the installed transformable optical elements) in order to minimize adverse optical deficiencies resulting from the shifted gaze direction of the current user. With respect to a direct-viewing optical device that does not include installed transformable optical elements, the customized non-transformable optical elements can be configured (e.g., supported on a pivotal base) to achieve physical realignment of such customized non-transformable optical elements to enhance acuity in response to a detected shift in gaze direction of the current user.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

Figure 31:
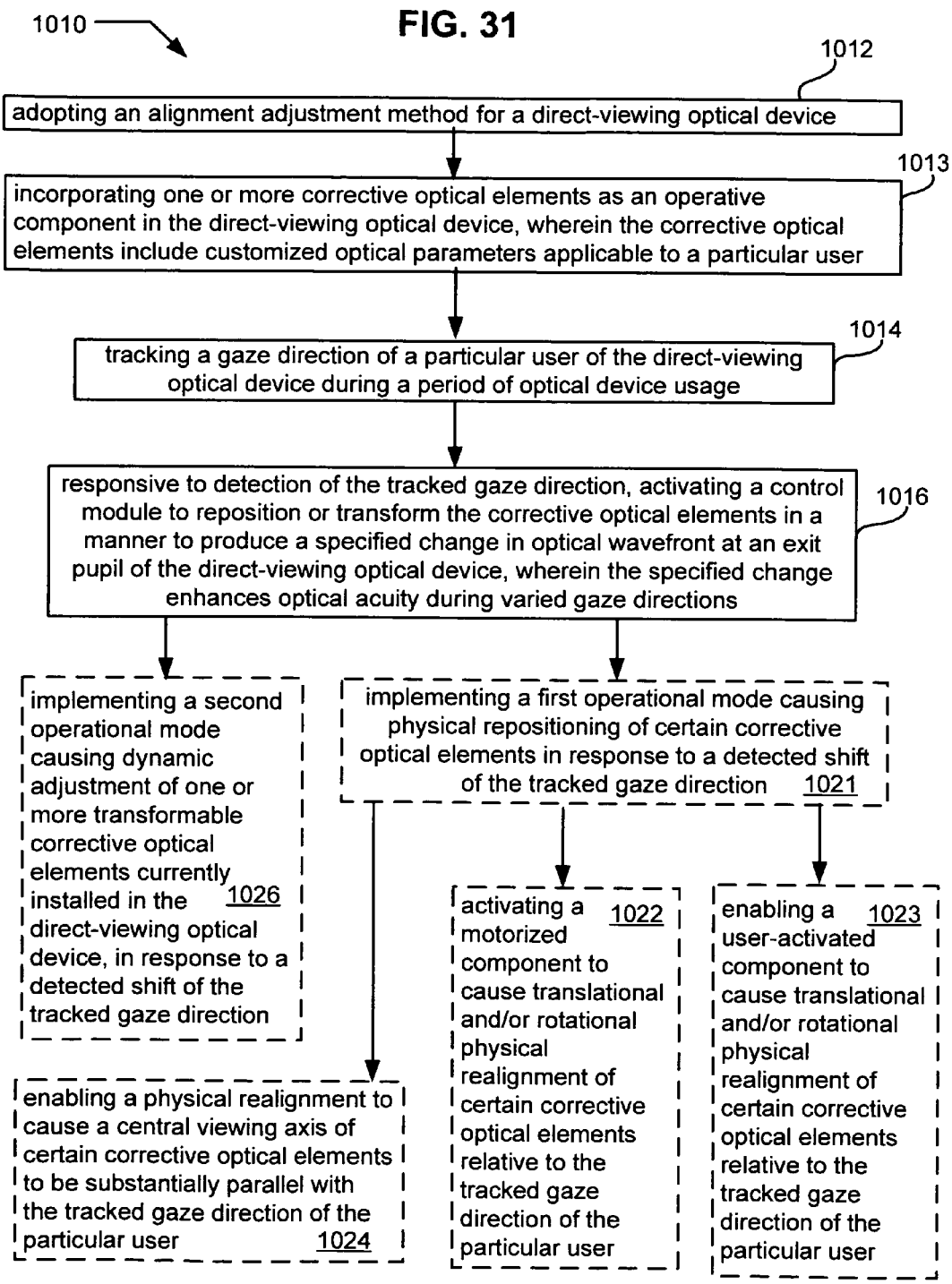
FIG. 31 is a high level flow chart showing exemplary method aspects regarding optical alignment corrections for a direct-viewing device.

Referring to the high-level flow chart of FIG. 31, various exemplary process features 1010 are illustrated with regard to adopting an alignment adjustment method for a direct-viewing optical device (see block 1012) which may include incorporating one or more corrective optical elements as an operative component in the direct-viewing optical device (block 1013), and may further include tracking a gaze direction of a particular user of the direct-viewing optical device during a period of optical device usage (block 1014). Another example includes responsive to detection of the tracked gaze direction, activating a control module to reposition or transform the corrective optical elements in a manner to produce a specified change in optical wavefront at an exit pupil of the direct-viewing optical device, wherein the specified change enhances optical acuity during varied gaze directions (block 1016).

Additional possible process features include implementing a first operational mode causing physical repositioning of certain corrective optical elements in response to a detected shift of the tracked gaze direction (block 1021). A related aspect may include activating a motorized component to cause translational and/or rotational physical realignment of certain corrective optical elements relative to the tracked gaze direction of the particular user (block 1022).

Also depicted in FIG. 31 is another exemplary process aspect that includes enabling a user-activated component to cause translational and/or rotational physical realignment of certain corrective optical elements relative to the tracked gaze direction of the particular user (block 1023). A further possibility includes enabling a physical realignment to cause a central viewing axis of certain corrective optical elements to be substantially parallel with the tracked gaze direction of the particular user (block 1024).

Some exemplary process embodiments include implementing a second operational mode causing dynamic adjustment of one or more transformable corrective optical elements currently installed in the direct-viewing optical device, in response to a detected shift of the tracked gaze direction (block 1026).

Figure 32:
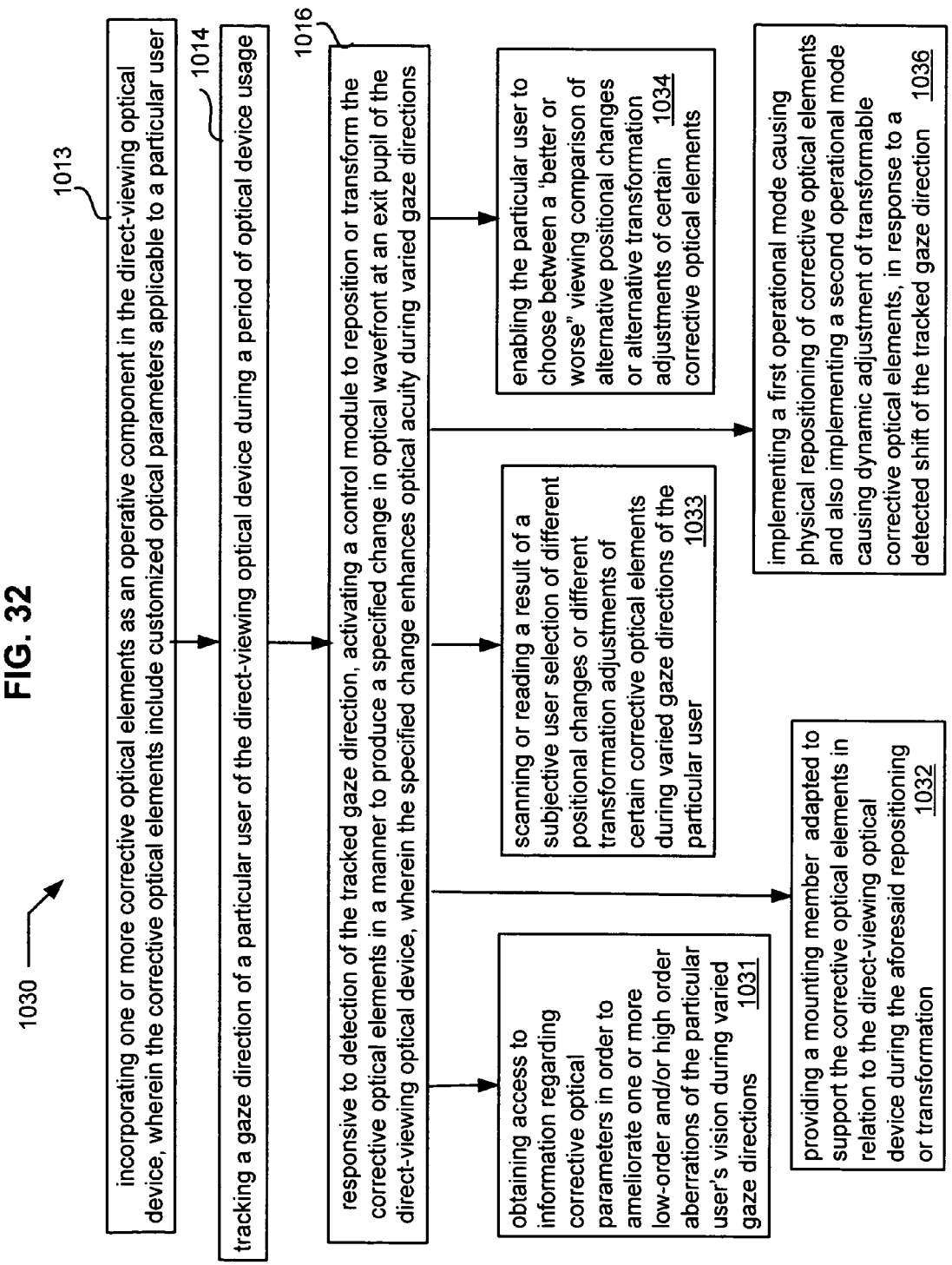
FIGS. 32-37 are detailed flow charts illustrating additional exemplary method aspects for adjustable optical alignment corrections.

The detailed flow chart of FIG. 32 illustrates various exemplary process operations 1030 including previously described aspects 1013, 1014, 1016 in combination with obtaining access to information regarding corrective optical parameters in order to ameliorate one or more low-order and/or high order aberrations of the particular user's vision during varied gaze directions (block 1031). Another aspect may include providing a mounting member adapted to support the corrective optical elements in relation to the direct-viewing optical device during the aforesaid repositioning or transformation (block 1032).

In some instances an example includes scanning or reading a result of a subjective user selection of different positional changes or different transformation adjustments of certain corrective optical elements during varied gaze directions of the particular user (block 1033). Another example may include enabling the particular user to choose between a 'better or worse" viewing comparison of alternative positional changes or alternative transformation adjustments of certain corrective optical elements (block 1034).

Further aspects may include implementing a first operational mode causing physical repositioning of corrective optical elements and also implementing a second operational mode causing dynamic adjustment of transformable corrective optical elements, in response to a detected shift of the tracked gaze direction (block 1036).

Figure 33:
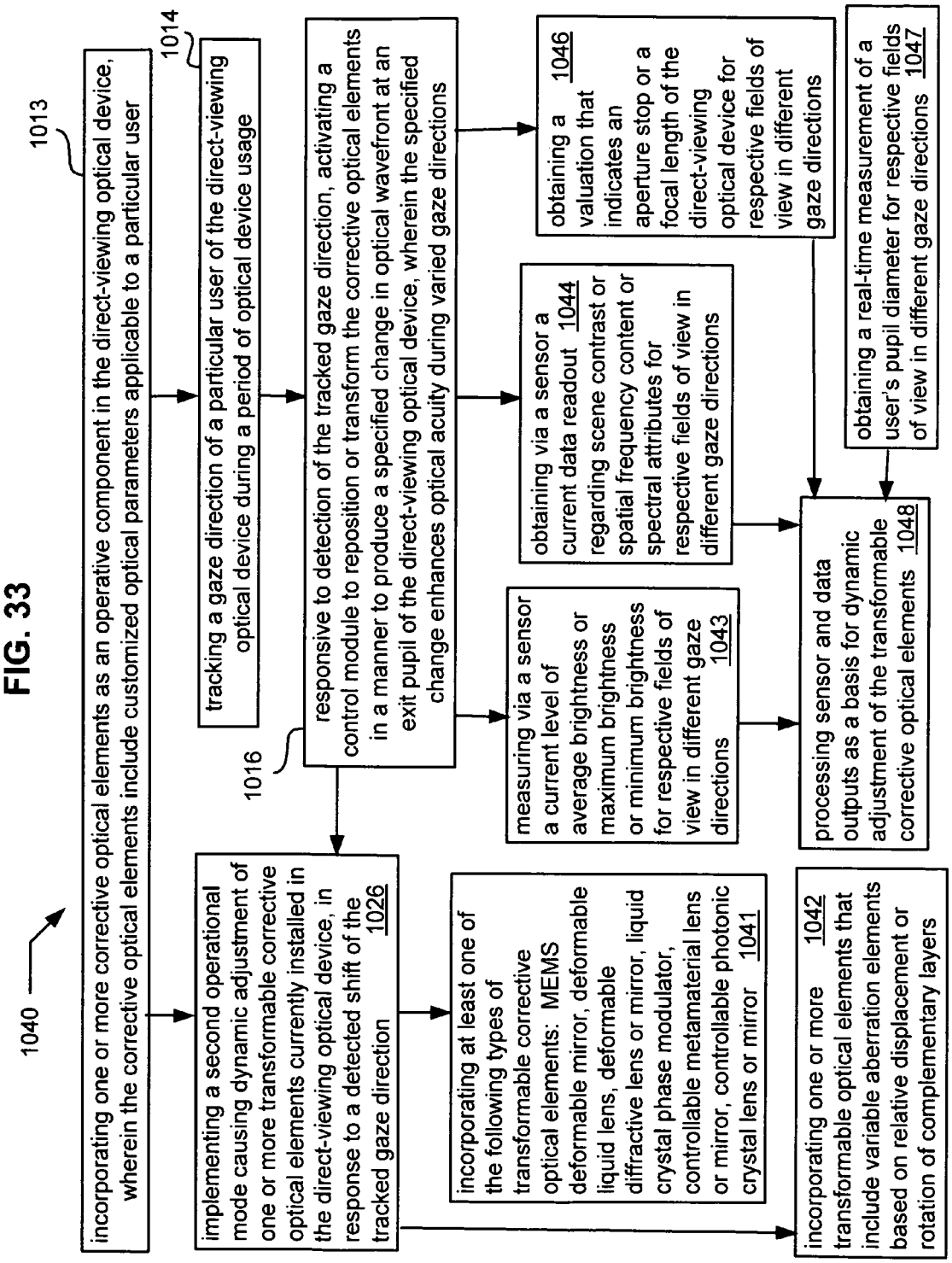

The illustrated process features 1040 of FIG. 33 include previously described aspects 1013, 1014, 1016, 1026 as well other possible aspects including incorporating at least one of the following types of transformable corrective optical elements: MEMS deformable mirror, deformable liquid lens, deformable diffractive lens or mirror, liquid crystal phase modulator, controllable metamaterial lens or mirror, controllable photonic crystal lens or mirror (block 1041). Another possibility includes incorporating one or more transformable optical elements that include variable aberration elements based on relative displacement or rotation of complementary layers (block 1042).

Additional aspects may include processing sensor and data outputs as a basis for dynamic adjustment of the transformable corrective optical elements (block 1048). A possible monitoring technique includes measuring via a sensor a current level of average brightness or maximum brightness or minimum brightness for respective fields of view in different gaze directions (block 1043). Other possibilities include obtaining via a sensor a current data readout regarding scene contrast or spatial frequency content or spectral attributes for respective fields of view in different gaze directions (block 1044).

Further techniques regarding sensor and data outputs may include obtaining a valuation that indicates an aperture stop or a focal length of the direct-viewing optical device for respective fields of view in different gaze directions (block 1046), and in some instances may include obtaining a real-time measurement of a user's pupil diameter for respective fields of view in different gaze directions (block 1047).

Figure 34:
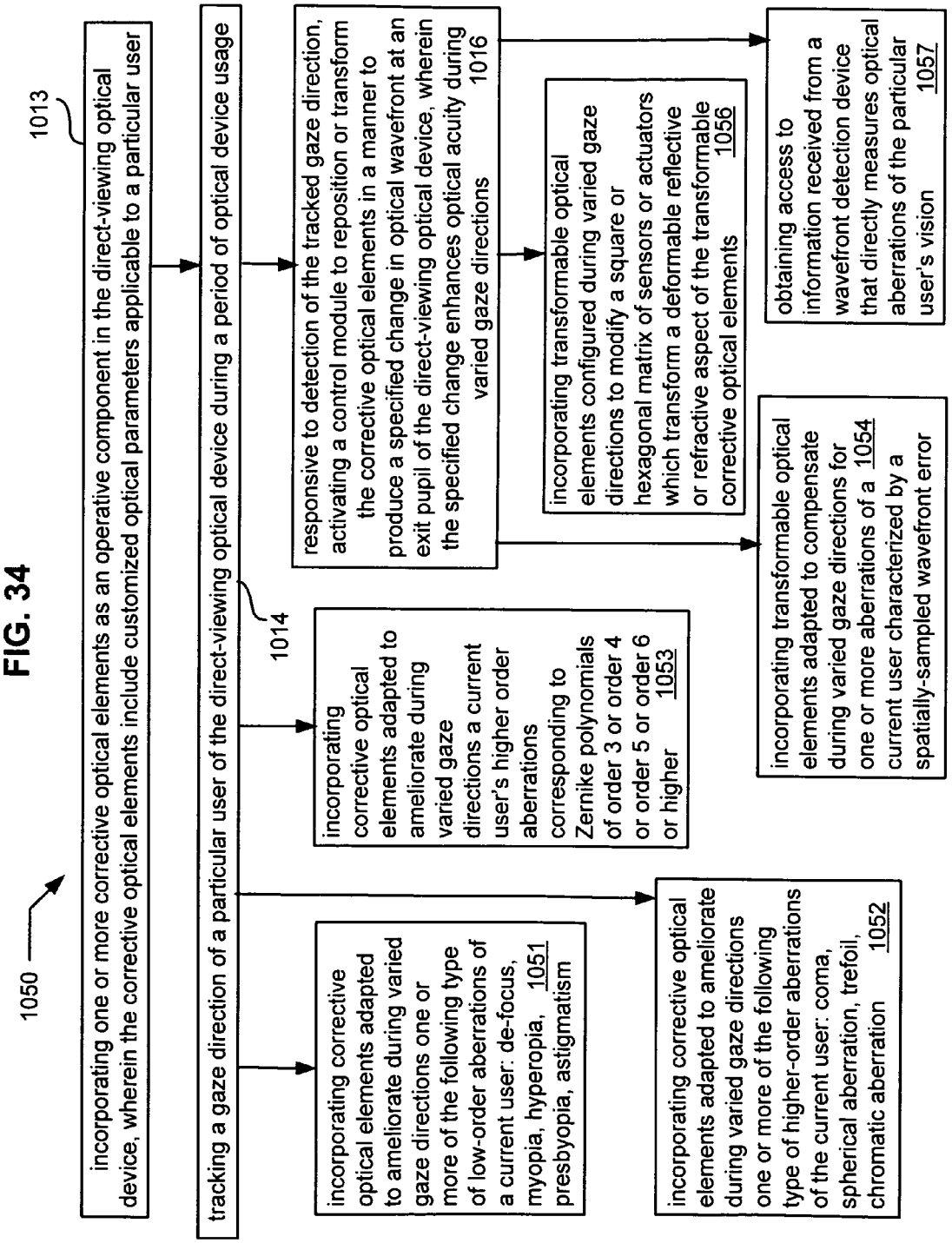

The detailed flow chart of FIG. 34 illustrates exemplary process enhancements 1050 that include previously described aspects 1013, 1014, 1016 in combination with incorporating corrective optical elements adapted to ameliorate during varied gaze directions one or more of the following type of low-order aberrations of a current user: de-focus, myopia, hyperopia, presbyopia, astigmatism (block 1041). Other exemplary process features include incorporating corrective optical elements adapted to ameliorate during varied gaze directions one or more of the following type of high-order aberrations of a current user: coma, spherical aberration, trefoil, chromatic aberration (block 1052).

Other process examples include incorporating corrective optical elements adapted to ameliorate during varied gaze directions a current user's high order aberrations corresponding to Zernike polynomials of order 3 or order 4 or order 5 or order 6 or higher (block 1053). Another example includes incorporating transformable optical elements adapted to compensate during varied gaze directions for one or more aberrations of a current user characterized by a spatially-sampled wavefront error (block 1054).

Some embodiments may include incorporating transformable optical elements configured during varied gaze directions to modify a square or hexagonal matrix of sensors or actuators which transform a deformable reflective or refractive aspect of the transformable corrective optical elements (block 1056). A further aspect may include obtaining access to information received from a wavefront detection device that directly measures optical aberrations of the particular user's vision (block 1057).

Figure 35:
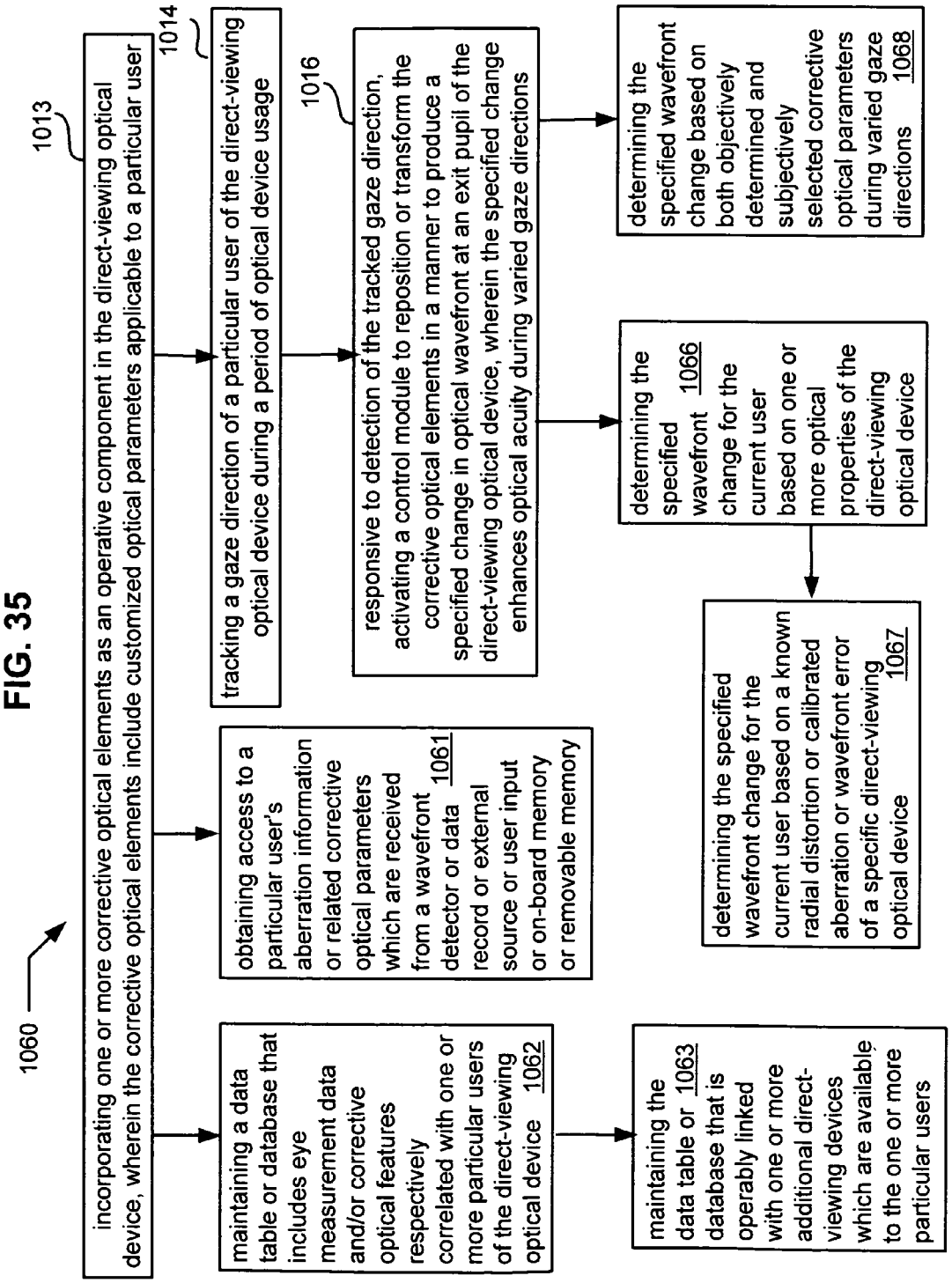

Referring to FIG. 35, exemplary embodiments may include various process operations 1060 including previously described aspects 1013, 1014, 1016 as well as obtaining access to a particular user's aberration information or related corrective optical parameters which are received from a wavefront detector or data record or external source or user input or on-board memory or removable memory (block 1061). In some instances a further aspect includes maintaining a data table or database that includes eye measurement data and/or corrective optical features respectively correlated with one or more particular users of the direct-viewing optical device (block 1062). A related aspect may include maintaining the data table or database that is operably linked with one or more additional direct-viewing devices which are available to the one or more particular users (block 1063).

Further possibilities include determining the specified wavefront change for the current user based on one or more optical properties of the direct-viewing optical device (block 1066). Related examples include determining the specified wavefront change for the current user based on a known radial distortion or calibrated aberration or wavefront error of a specific direct-viewing optical device (block 1067). An additional example includes determining the specified wavefront change based on both objectively determined and subjectively selected corrective optical parameters during varied gaze directions (block 1068).

Figure 36:
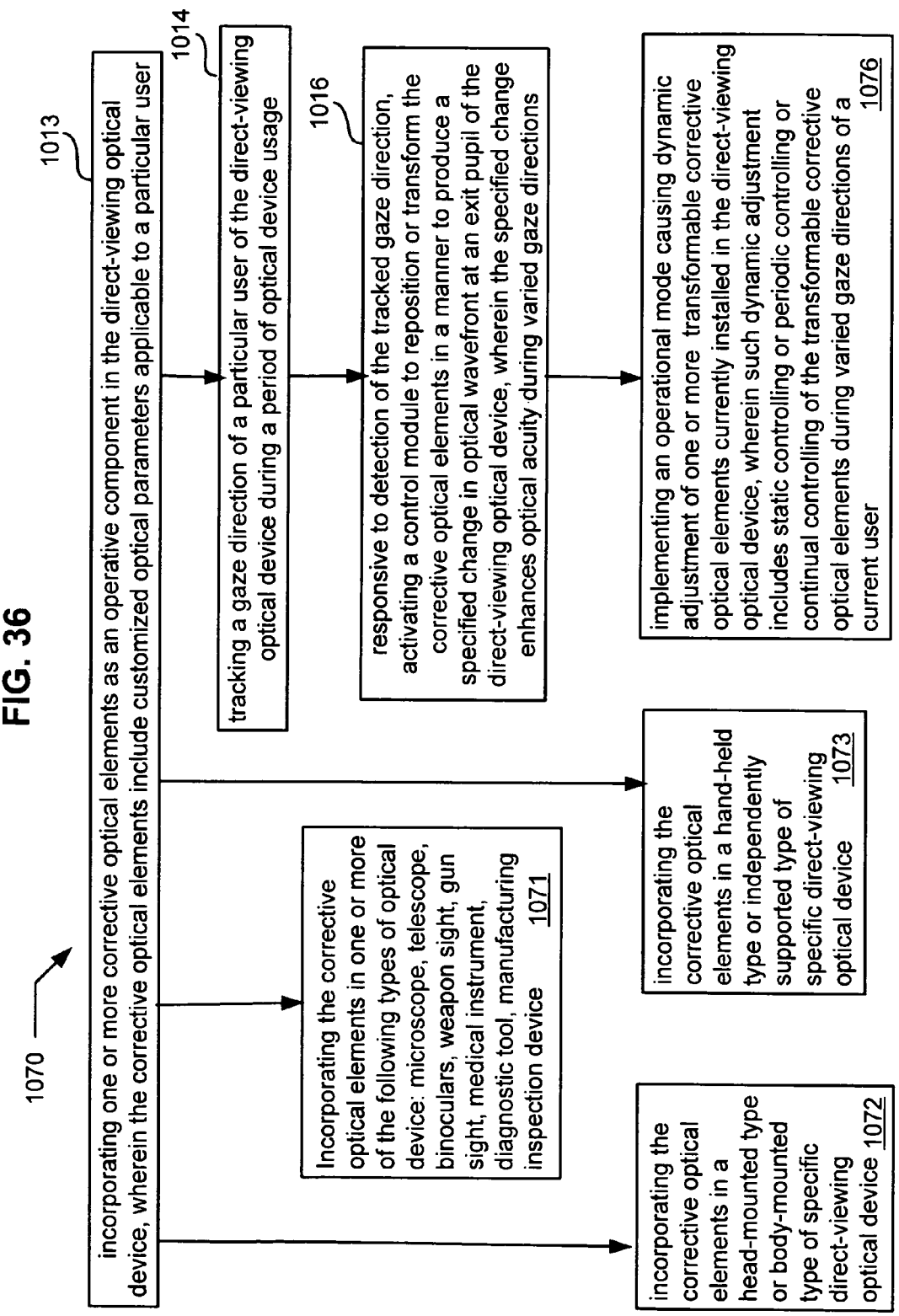

Referring to FIG. 36, various illustrated process features 1070 may be adopted including previously described aspects 1013, 1014, 1016 in combination with incorporating the corrective optical elements in one of the following types of direct-viewing optical device: microscope, telescope, binoculars, weapon sight, gun sight, medical instrument, diagnostic tool, manufacturing inspection device (block 1071). Some embodiments may include incorporating the corrective optical elements in a head-mounted type or body-mounted type of specific direct-viewing optical device (block 1072). Other examples include incorporating the corrective optical elements in a hand-held type or independently supported type of specific direct-viewing optical device (block 1073).

Further possibilities include implementing an operational mode causing dynamic adjustment of one or more transformable corrective optical elements currently installed in the direct-viewing optical device, wherein such dynamic adjustment includes static controlling or periodic controlling or continual controlling of the transformable corrective optical elements during varied gaze directions of a current user (block 1076).

Figure 37:
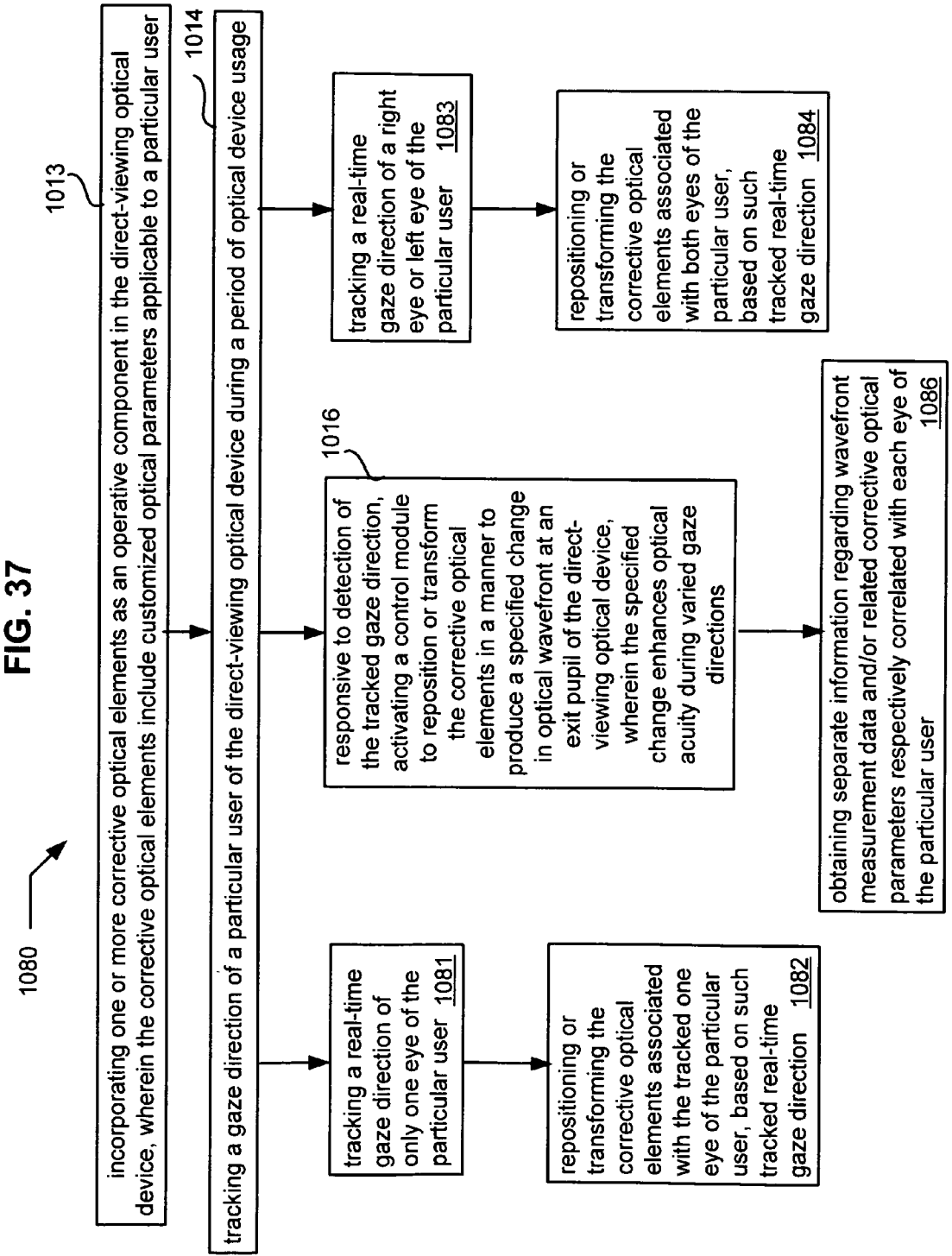

The detailed flow chart in FIG. 37 shows possible process aspects 1080 that include previously described components 1013, 1014, 1016 and also include tracking a real-time gaze direction of only one eye of the particular user (block 1081). A related aspect may include repositioning or transforming the corrective optical elements associated with the tracked one eye of the particular user, based on such tracked real-time gaze direction (block 1082).

Other possibilities include tracking a real-time gaze direction of a right eye or left eye of the particular user (block 1083), and repositioning or transforming the corrective optical elements associated with both eyes of the particular user, based on such tracked real-time gaze direction (block 1084). In some instances a further aspect may include obtaining separate information regarding wavefront measurement data and/or related corrective optical parameters respectively correlated with each eye of the particular user (block 1086).

It will be understood from the exemplary embodiments disclosed herein that numerous individual method operations depicted in the flow charts of FIGS. 31-37 can be incorporated as encoded instructions in computer readable media in order to obtain enhanced benefits and advantages.

Figure 38:
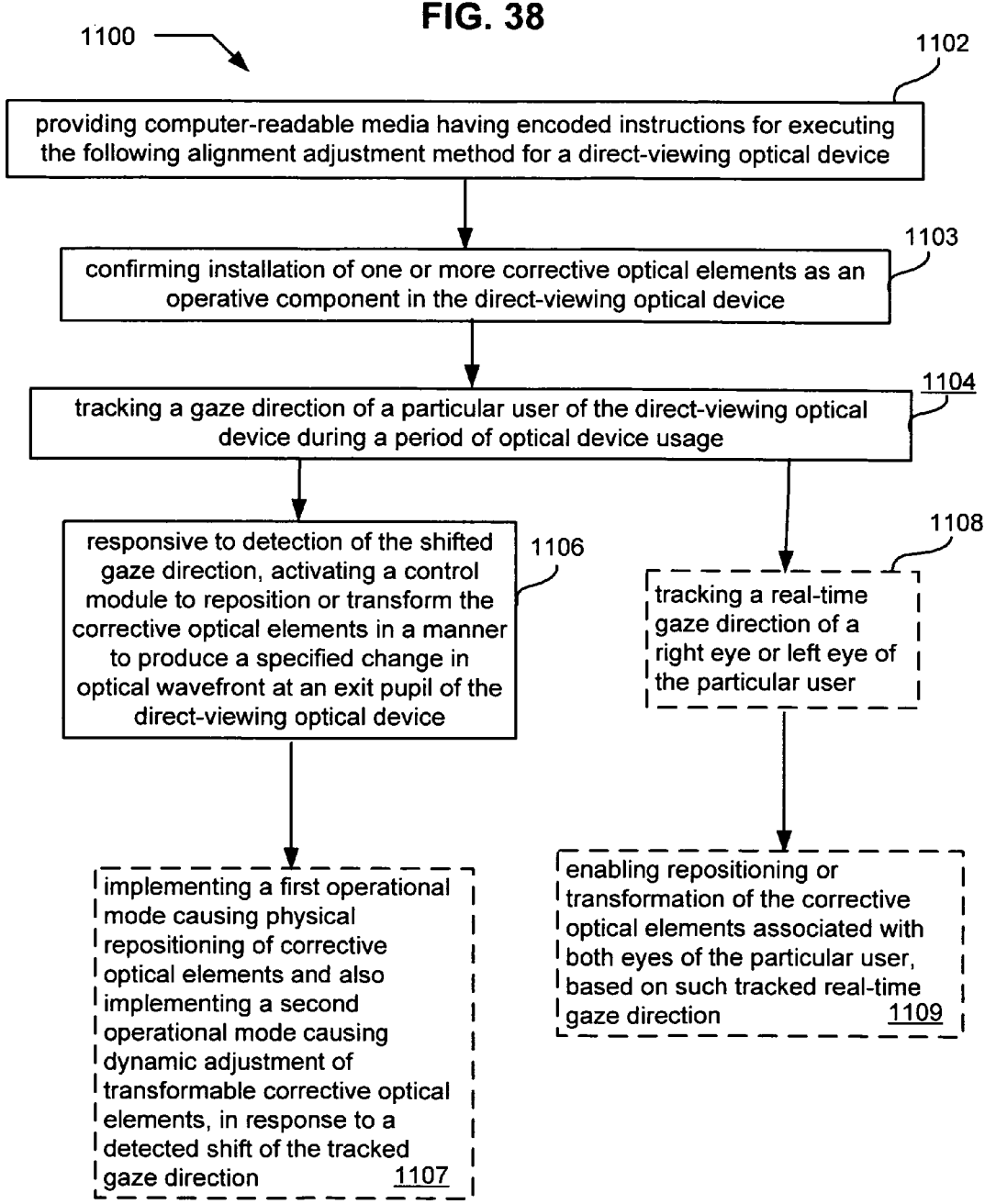
FIG. 38 is a diagrammatic flow chart for further exemplary computer-readable media embodiment features.

As another embodiment example, FIG. 38 shows a diagrammatic flow chart depicting an article of manufacture which provides computer-readable media having encoded instructions for executing an alignment adjustment method for a direct-viewing optical device (block 1100), wherein the method includes confirming installation of one or more corrective optical elements as an operative component in the direct-viewing optical device (block 1102); tracking a gaze direction of a particular user of the direct-viewing optical device during a period of optical device usage (block 1103); and responsive to detection of the shifted gaze direction, activating a control module to reposition or transform the corrective optical elements in a manner to produce a specified change in optical wavefront at an exit pupil of the direct-viewing optical device (block 1104).

Additional programmed aspects may include implementing a first operational mode causing physical repositioning of corrective optical elements and also implementing a second operational mode causing dynamic adjustment of transformable corrective optical elements, in response to a detected shift of the tracked gaze direction (block 1107). Other programmed method examples include tracking a real-time gaze direction of a right eye or left eye of the particular user (block 1008); and enabling repositioning or transformation of the corrective optical elements associated with both eyes of the particular user, based on such tracked real-time gaze direction (block 1109).

It will be understood by those skilled in the art that the various components and elements disclosed in the system and schematic diagrams herein as well as the various steps and sub-steps disclosed in the flow charts herein may be incorporated together in different claimed combinations in order to enhance possible benefits and advantages.

The exemplary system, apparatus, and computer program product embodiments disclosed herein including FIGS. 1-5, FIGS. 15-18, FIGS. 29-30 and FIG. 38, along with other components, devices, know-how, skill and techniques known in the art have the capability of implementing and practicing the methods and processes that are depicted in FIGS. 6-14, FIGS. 19-28 and FIGS. 31-37. However it is to be further understood by those skilled in the art that other systems, apparatus and technology may be used to implement and practice such methods and processes.

As shown and described herein, exemplary methods, systems and components enable an enhanced direct-viewing optical device to make customized adjustments that accommodate various optical aberrations of a current user. In some instances a real-time adjustment of the transformable optical elements is based on known corrective optical parameters associated with a current user. In some implementations a control module may process currently updated wavefront measurements as a basis for determining appropriate real-time adjustment of the transformable optical elements to produce a specified change in optical wavefront at an exit pupil of the direct-viewing device. Possible transformable optical elements may have refractive and/or reflective and/or diffractive and/or transmissive characteristics that are adjusted based on current performance viewing factors for a given field of view of the direct-viewing device. Some embodiments enable dynamic repositioning and/or transformation of corrective optical elements based on a detected shift of a tracked gaze direction of a current user of the direct-viewing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An adjustable system for a direct-viewing optical device, comprising:
    one or more optical elements adapted for mounting on the direct-viewing optical device, wherein the optical elements are capable of transformation to achieve enhanced acuity during a period of usage by a current user;
    a control module operably coupled to the one or more transformable optical elements, the control module configured to activate or modify or bypass certain optical features of the one or more optical elements based on performance viewing factors to produce a specified change in optical wavefront at an exit pupil of the direct-viewing optical device, wherein the specified change includes at least one higher-order corrective feature respectively correlated with an aberrational characteristic of the current user; and
    at least one sensor component operatively coupled to the control module and configured to monitor or measure one or more real-time performance viewing factors regarding an operating condition or image property or viewing environment for a given field of view of the direct-viewing optical device,
    wherein the control module is configured to
        determine spatial frequency content for the given field of view based on output from the at least one sensor component,
        determine, based on stored performance viewing factors for the current user, adjustable optical parameters corresponding to the spatial frequency content, and
        automatically adjust the transformable optical element during an optical device usage period based on the determined optical parameters.

2. The system of claim 1 wherein the control module is configured to measure a level of average brightness in the given field of view using an illumination sensor and to automatically adjust the transformable optical element during an optical device usage period based on the level of average brightness.

3. The system of claim 1 wherein the control module is configured to measure a level of scene contrast in the given field of view based on output from the at least one sensor component and to automatically adjust the transformable optical element during an optical device usage period based on the level of scene contrast.

4. The system of claim 1 wherein the control module is configured to determine a location of an identifiable target object in the given field of view and to automatically adjust the transformable optical element during an optical device usage period based on the location.

5. The system of claim 1 wherein said sensor component includes an illumination sensor, wherein the control module is configured to measure a level of maximum or minimum brightness in the given field of view using the illumination sensor and to automatically adjust the transformable optical element during an optical device usage period based on the maximum or minimum brightness.

6. The system of claim 1 wherein the control module is configured to determine spectral attributes for the given field of view and to automatically adjust the transformable optical element during an optical device usage period based on the spectral attributes.

7. The system of claim 1 wherein the control module is configured to determine a current focal length calibration for the direct-viewing optical device and to automatically adjust the transformable optical element during an optical device usage period based on the current focal length calibration.

8. The system of claim 1 wherein the control module is configured to determine a current aperture stop calibration for the optical device and to automatically adjust the transformable optical elements during an optical device usage period based on the current aperture stop calibration.

9. The system of claim 1 wherein the control module is configured to measure, via the at least one sensor component, a real time diameter of the current user's pupil and to automatically adjust the transformable optical elements during an optical device usage period based on the real-time diameter.

10. The system of claim 1 wherein the one or more transformable optical elements also include additional corrective features to ameliorate one or more of the following low-order aberrations of the current user: myopia, hyperopia, presbyopia, astigmatism.

11. The system of claim 1 wherein the one or more transformable optical elements include certain corrective features to ameliorate one or more of the following type of higher-order aberrations of the current user: coma, spherical aberration, trefoil, chromatic aberration.

12. The system of claim 1 wherein the one or more transformable optical elements include certain corrective features to ameliorate the current user's high order aberrations corresponding to Zernike polynomials of order 3 or order 4 or order 5 or order 6 or higher.

13. The system of claim 1 wherein the one or more transformable optical elements include certain corrective features to compensate for one or more aberrations characterized by a spatially-sampled wavefront error.

14. The system of claim 1 wherein said control module is configured to modify a square or hexagonal matrix of sensors or actuators which transform a deformable reflective or refractive aspect of the one or more optical elements.

15. The system of claim 1 further comprising:
a specific direct-viewing optical device adapted to incorporate the one or more transformable optical elements.

16. The system of claim 15 wherein the specific direct-viewing optical device includes one of the following: microscope, telescope, binoculars, weapon sight, gun sight, medical instrument, diagnostic tool, manufacturing inspection device.

17. The system of claim 15 wherein the specific direct-viewing optical device includes:
a head-mounted type or body-mounted type of specific direct-viewing optical device adapted to incorporate the one or more transformable optical elements.

18. The system of claim 15 wherein the specific direct-viewing optical device includes:
a hand-held type or independently supported type of specific direct-viewing optical device adapted to incorporate the one or more transformable optical elements.

19. The system of claim 1 further comprising:
one or more mounting features adapted to support the one or more transformable optical elements in relation to the direct-viewing optical device.

20. The system of claim 19 wherein the mounting features are configured to incorporate the one or more transformable optical elements in an eyepiece for the direct-viewing optical device.

21. The system of claim 19 wherein the mounting features are configured to position the one or more transformable optical elements as an insert between an eyepiece and a remainder portion of the direct-viewing optical device.

22. The system of claim 19 wherein the mounting features are configured to position the one or more transformable optical elements as an insert between a user's eye and an eyepiece of the direct-viewing device.

23. The system of claim 1 wherein said control module is configured for causing dynamic adjustment of the one or more transformable optical elements currently installed in the direct-viewing optical device.

24. The system of claim 23 wherein the one or more transformable optical elements include one or more of the following: MEMS deformable mirror, deformable liquid lens, deformable diffractive lens or mirror, liquid crystal phase modulator, controllable metamaterial lens or mirror, controllable photonic crystal lens or mirror.

25. The system of claim 23 wherein the one or more transformable optical elements include one or more variable aberration elements based on relative displacement or rotation of complementary layers.

26. The system of claim 1 wherein the one or more transformable optical elements are configured to include both objectively determined and subjectively selected adjustable optical parameters.

27. A computer program product comprising computer-readable media having encoded instructions for executing an optical adjustment method for a direct-viewing optical device, wherein the method includes:
periodically detecting one or more real-time performance viewing factors regarding an operating condition or image property or viewing environment for a given field of view of the direct-viewing optical device that includes one or more transformable optical elements wherein detecting the one or more real-time performance viewing factors comprises determining a spatial frequency content for the given field of view;
processing information regarding low-order and/or high-order aberrations correlated with a current user of the direct-viewing optical device to determine adjustable optical parameters for the current user corresponding to the spatial frequency content; and
responsive to the detected performance viewing factors and based on the processed aberration information, adjusting the transformable optical elements in a manner to produce a specified change in optical wavefront at an exit pupil of the direct-viewing optical device, wherein adjusting comprises automatically adjusting the transformable optical element during an optical device usage period based on the determined optical parameters.

28. The computer program product of claim 27 wherein said processing information includes:
processing information regarding corrective optical parameters to ameliorate one or more of the following type of low-order aberrations of the current user: myopia, hyperopia, presbyopia, astigmatism.

29. The computer program product of claim 27 wherein said processing information includes:
processing information regarding corrective optical parameters to ameliorate one or more of the following type of higher-order aberrations of the current user: coma, spherical aberration, trefoil, chromatic aberration.

30. The computer program product of claim 27 wherein said processing information includes:
processing information regarding certain corrective optical parameters to ameliorate the current user's high order aberrations corresponding to Zernike polynomials of order 3 or order 4 or order 5 or order 6 or higher.

31. The computer program product of claim 27 wherein said processing information includes:
processing information regarding certain corrective optical parameters to compensate for one or more aberrations characterized by a spatially-sampled wavefront error.

32. The computer program product of claim 27 wherein said adjusting the transformable optical elements includes:
adjusting a square or hexagonal matrix of sensors or actuators which transform a deformable reflective or refractive aspect of the one or more optical elements.

33. The computer program product of claim 27 wherein said processing information includes:

processing information from a data table or database or external source or user input or on-board memory or removable memory indicating default adjustable optical parameters for the current user applicable to one or more of the following type of real-time performance viewing factors: field of view, brightness, scene contrast, identified target object, spatial frequency content, spectral attributes, focal length of optical device, aperture stop, user's pupil diameter.

34. The computer program product of claim 33 wherein the method operations include:
adopting the default adjustable optical parameters based on adjustable optical parameters implemented for the current user during a previous optical device usage period.

35. The computer program product of claim 27 wherein the method operations include:
determining the specified wavefront change for the current user based on one or more optical properties of a specific direct-viewing optical device.

36. The computer program product of claim 35 wherein said determining the specified wavefront change includes:
determining the specified wavefront change for the current user based on a known radial distortion or calibrated aberration or wavefront error of the specific direct-viewing optical device.

37. The computer program product of claim 27 wherein the method operations include:
confirming identification of one of the following type of direct-viewing devices that includes the transformable optical elements: microscope, telescope, binoculars, weapon sight, gun sight, medical instrument, diagnostic tool, manufacturing inspection device.

38. The computer program product of claim 27 wherein said adjusting the transformable optical elements includes:
modifying the one or more transformable optical elements based on both sensor output data and user input data.

39. The computer program product of claim 27 wherein said processing information includes:
processing a pre-programmed set of objectively determined adjustable optical parameters for low-order or higher-order aberrations; and
processing a further set of subjectively chosen adjustable optical parameters for low-order or higher-order aberrations; and
subsequently adjusting the transformable optical elements based on both the pre-programmed set and the further set as a basis for corrective features included in the transformable optical elements.

40. The computer program product of claim 27 wherein the method operations include:
activating a viewing display that enables the current user to choose subjectively between a "better or worse" comparison of possible corrective features to be included in the transformable optical elements.

41. The computer program product of claim 27 wherein said processing information includes:
processing information regarding eye measurement data and/or corrective optical parameters correlated with the current user of the optical device.

42. The computer program product of claim 27 wherein said processing information includes:
processing information indicating a right eye or left eye or both eyes which correspond to corrective optical parameters correlated with the current user.

43. The computer program product of claim 27 wherein the method operations include:
maintaining a data record that includes eye measurement data and/or corrective optical parameters respectively correlated with one or more particular users of the direct-viewing optical device.

44. The computer program product of claim 43 wherein said maintaining the data record includes:
enabling a communication link to make the data record accessible to one or more additional direct viewing devices which are available to the one or more particular users.

45. The computer program product of claim 27 wherein the method operations include:
enabling an authorization protocol to confirm identity of the current user of the direct-viewing optical device.

46. The computer program product of claim 45 wherein said enabling the authorization protocol includes:
establishing confirmation of the current user identity by name or password or biometric match or eye feature recognition.

47. The computer program product of claim 27 wherein said adjusting the transformable optical elements includes:
enabling dynamic adjustment that includes static control or periodic control or continuous control of the transformable optical elements during a real-time optical device usage period of the current user.

* * * * *

UNITED STATES PATENT AND TRADEMARK OFFICE
CERTIFICATE OF CORRECTION

| | | |
|---|---|---|
| PATENT NO. | : 9,046,683 B2 | Page 1 of 1 |
| APPLICATION NO. | : 13/374520 | |
| DATED | : June 2, 2015 | |
| INVENTOR(S) | : Caldeira et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 56 days.

Signed and Sealed this
Twenty-ninth Day of March, 2016

Michelle K. Lee
*Director of the United States Patent and Trademark Office*